(12) United States Patent
Cao et al.

(10) Patent No.: US 9,068,234 B2
(45) Date of Patent: *Jun. 30, 2015

(54) METHODS AND AGENTS FOR SCREENING FOR COMPOUNDS CAPABLE OF MODULATING GENE EXPRESSION

(75) Inventors: Liangxian Cao, Parlin, NJ (US); Anuradha Mehta, Piscataway, NJ (US); Nikolai A. Naryshkin, East Brunswick, NJ (US); Matthew C. Pellegrini, Bedminster, NJ (US); Charles M. Romfo, Easton, PA (US); Panayiota Trifillis, Piscataway, NJ (US); Christopher R. Trotta, Somerset, NJ (US)

(73) Assignee: PTC Therapeutics, Inc., South Plainfield, NJ (US)

( * ) Notice: Subject to any disclaimer, the term of this patent is extended or adjusted under 35 U.S.C. 154(b) by 1036 days.

This patent is subject to a terminal disclaimer.

(21) Appl. No.: 10/895,393

(22) Filed: Jul. 21, 2004

(65) Prior Publication Data

US 2005/0048549 A1   Mar. 3, 2005

Related U.S. Application Data

(63) Continuation-in-part of application No. PCT/US2004/001643, filed on Jan. 21, 2004.

(60) Provisional application No. 60/441,637, filed on Jan. 21, 2003.

(51) Int. Cl.
  *C12Q 1/68*   (2006.01)
  *C07H 21/02*   (2006.01)

(52) U.S. Cl.
  CPC .................................. *C12Q 1/6897* (2013.01)

(58) Field of Classification Search
  None
  See application file for complete search history.

(56) References Cited

U.S. PATENT DOCUMENTS

| | | |
|---|---|---|
| 3,346,381 A | 10/1967 | Grieg |
| 5,439,797 A | 8/1995 | Tsien et al. |
| 5,444,149 A | 8/1995 | Keene et al. |
| 5,518,885 A | 5/1996 | Raziuddin et al. |
| 5,587,300 A | 12/1996 | Malter |
| 5,691,145 A | 11/1997 | Pitner et al. |
| 5,698,427 A | 12/1997 | Keene et al. |
| 5,700,660 A | 12/1997 | Leonard et al. |
| 5,731,343 A | 3/1998 | Feng et al. |
| 5,734,039 A | 3/1998 | Calabretta et al. |
| 5,776,738 A | 7/1998 | Dell'Orco, Sr. et al. |
| 5,843,770 A | 12/1998 | Ill et al. |
| 5,849,520 A | 12/1998 | Leonard et al. |
| 5,859,227 A | 1/1999 | Giordano et al. |
| 5,908,779 A | 6/1999 | Carmichael et al. |
| 5,928,888 A | 7/1999 | Whitney |
| 5,990,298 A | 11/1999 | Carmichael et al. |
| 6,004,749 A | 12/1999 | Giordano et al. |
| 6,010,856 A * | 1/2000 | Ulevitch et al. .............. 435/6.14 |
| 6,057,437 A | 5/2000 | Kamiya et al. |
| 6,107,029 A | 8/2000 | Giordano |
| 6,159,709 A | 12/2000 | Korneluk et al. |
| 6,171,821 B1 | 1/2001 | Korneluk et al. |
| 6,203,976 B1 | 3/2001 | Foulkes et al. |
| 6,203,982 B1 * | 3/2001 | Nunokawa et al. ............... 435/6 |
| 6,214,563 B1 | 4/2001 | Negulescu et al. |
| 6,221,587 B1 | 4/2001 | Ecker et al. |
| 6,221,612 B1 | 4/2001 | Knapp et al. |
| 6,232,070 B1 | 5/2001 | Shuman |
| 6,265,167 B1 | 7/2001 | Carmichael et al. |
| 6,265,546 B1 | 7/2001 | Cohen et al. |
| 6,284,882 B1 | 9/2001 | Wu-Wong et al. |
| 6,303,295 B1 | 10/2001 | Taylor et al. |
| 6,331,170 B1 | 12/2001 | Ordway |
| 6,331,396 B1 | 12/2001 | Silverman et al. |
| 6,399,373 B1 | 6/2002 | Bougueleret |
| 6,448,007 B1 | 9/2002 | Giordano et al. |
| 6,455,280 B1 | 9/2002 | Edwards et al. |
| 6,465,176 B1 | 10/2002 | Giordano et al. |
| 6,476,208 B1 | 11/2002 | Cohen et al. |
| 6,528,060 B1 | 3/2003 | Nicolette |
| 6,617,493 B1 | 9/2003 | Fader |
| 6,627,797 B1 | 9/2003 | Duvick et al. |
| 6,630,589 B1 * | 10/2003 | Giordano et al. ............. 546/139 |
| 6,635,671 B1 | 10/2003 | Kastelic et al. |
| 6,638,522 B1 | 10/2003 | Mulye |
| 6,645,747 B1 | 11/2003 | Hallahan et al. |
| 6,653,132 B1 | 11/2003 | Keshet et al. |
| 6,667,152 B2 | 12/2003 | Miles et al. |
| 6,872,850 B2 | 3/2005 | Giordano et al. |

(Continued)

FOREIGN PATENT DOCUMENTS

| | | |
|---|---|---|
| EP | 1 176 196 | 1/2002 |
| EP | 1 604 011 | 12/2005 |

(Continued)

OTHER PUBLICATIONS

Grens et al. (1990) J. Biol. Chem. 265: 11810-11816.*
Huang et al. (1990) Nucleic Acids Res. 18:937-947.*
Akiri et al., "Regulation of Vascular Endothelial Growth Factor (VEGF) Expression is Mediated by Internal Initiation of Translation and Alternative Initiation of Transcription", *Oncogene*, 17:227-236 (1998).

(Continued)

*Primary Examiner* — Nancy T Vogel
(74) *Attorney, Agent, or Firm* — Jones Day

(57) ABSTRACT

The invention relates to the fields of screening assays, compounds, and methods for altering gene expression and protein levels. In particular, the invention includes assays to screen for agents capable of modulating gene expression in a UTR-dependent manner and agents capable of modulating gene expression.

17 Claims, 5 Drawing Sheets

(56) References Cited

U.S. PATENT DOCUMENTS

| | | | |
|---|---|---|---|
| 7,078,171 B2 | 7/2006 | Giordano et al. | |
| 7,371,726 B2 | 5/2008 | Junker et al. | |
| 7,598,079 B2 | 10/2009 | Kastelic et al. | |
| 7,598,361 B2 | 10/2009 | Cheikh et al. | |
| 7,601,840 B2 | 10/2009 | Moon et al. | |
| 7,767,689 B2 | 8/2010 | Moon et al. | |
| 8,076,352 B2 | 12/2011 | Cao et al. | |
| 8,076,353 B2 | 12/2011 | Cao et al. | |
| 8,283,115 B1 | 10/2012 | Friesen et al. | |
| 8,283,116 B1 | 10/2012 | Bhattacharyya et al. | |
| 8,426,194 B2 | 4/2013 | Cao et al. | |
| 8,460,864 B2 | 6/2013 | Cao et al. | |
| 2002/0006661 A1* | 1/2002 | Green et al. | 435/325 |
| 2002/0132257 A1 | 9/2002 | Giordano et al. | |
| 2003/0135870 A1 | 7/2003 | Cheikh et al. | |
| 2003/0199453 A1 | 10/2003 | Giordano et al. | |
| 2004/0063120 A1 | 4/2004 | Beer et al. | |
| 2004/0091866 A1 | 5/2004 | Giordano et al. | |
| 2004/0138282 A1 | 7/2004 | Greig et al. | |
| 2004/0152117 A1 | 8/2004 | Giordano et al. | |
| 2004/0214223 A1 | 10/2004 | Cao et al. | |
| 2004/0231007 A1 | 11/2004 | Kastelic et al. | |
| 2005/0048549 A1 | 3/2005 | Cao et al. | |
| 2007/0072186 A1 | 3/2007 | Mehta et al. | |
| 2007/0111203 A1 | 5/2007 | Cao et al. | |
| 2007/0254878 A1 | 11/2007 | Cao et al. | |
| 2008/0064683 A1 | 3/2008 | Cao et al. | |
| 2009/0068654 A1 | 3/2009 | Kastelic et al. | |

FOREIGN PATENT DOCUMENTS

| | | |
|---|---|---|
| EP | 1 761 638 | 3/2007 |
| GB | 9828707.1 | 12/1998 |
| GB | 9828709.7 | 12/1998 |
| JP | 2001/46086 | 2/2001 |
| JP | 2008/507271 | 3/2008 |
| WO | WO 95/28485 | 10/1995 |
| WO | WO 95/33831 | 12/1995 |
| WO | WO 97/25860 | 7/1997 |
| WO | WO 97/25860 A | 7/1997 |
| WO | WO 98/39484 | 9/1998 |
| WO | WO 93/20212 | 10/1999 |
| WO | WO 00/04051 | 1/2000 |
| WO | WO 00/05356 | 2/2000 |
| WO | WO 00/05366 | 2/2000 |
| WO | WO 00/39314 | 7/2000 |
| WO | WO 00/46247 | 8/2000 |
| WO | WO 01/84155 | 8/2001 |
| WO | WO 02/48150 | 6/2002 |
| WO | WO 02/077609 | 10/2002 |
| WO | WO 02/083953 | 10/2002 |
| WO | WO 03/087815 A2 | 10/2003 |
| WO | WO 2004/065561 | 8/2004 |
| WO | WO 2005/049868 | 6/2005 |
| WO | WO 2005/095615 | 10/2005 |
| WO | WO 2005/118857 | 12/2005 |
| WO | WO 2006/022712 | 3/2006 |

OTHER PUBLICATIONS

Bornes et al., "Control of the Vascular Endothelial Growth Factor Internal Ribosome Entry Site (IRES) Activity and Translation Initiation by Alternatively Spliced Coding Sequences", *The Journal of Biological Chemistry*, 279(18):18717-18726 (2004).

Claffey et al., "Identification of a Human VPF/VEGF 3' Untranslated Region Mediating Hypoxia-Induced mRNA Stability", *Molecular Biology of the Cell*, 9:469-481 (1998).

Dreyfuss et al., "Messenger-RNA-Binding Proteins and the Messages They Carry", *Nature Reviews Molecular Cell Biology*, 3:195-205 (2002).

Huez et al., "Two Independent Internal Ribosome Entry Sites are Involved in Translation Initiation of Vascular Endothelial Growth Factor mRNA", *Molecular and Cellular Biology*, 18(11):6178-6190 (1998).

Kedersha et al, "Stress Granules: Sites of mRNA Triage that Regulate mRNA Stability and Translatability", *Biochemical Society Transactions*, 30(6):963-969 (2002).

Kozak, M., "Influences of mRNA Secondary Structure on Initiation by Eukaryotic Ribosomes", *Proc. Natl. Acad. Sci. USA*, 83:2850-2854 (1986).

Lai et al., "Evidence that Tristetraprolin Binds to AU-Rich Elements and Promotes the Deadenylation and Destabilization of Tumor Necrosis Factor Alpha mRNA", *Molecular and Cellular Biology*, 19(6):4311-4323 (1999).

Miller et al., "The Vascular Endothelial Growth Factor mRNA Contains an Internal Ribosome Entry Site", *FEBS Letters*, 434:417-420 (1998).

Stein et al., "Translation of Vascular Endothelial Growth Factor mRNA by Internal Ribosome Entry: Implications for Translation under Hypoxia", *Molecular and Cellular Biology*, 18(6):3112-3119 (1998).

Stoecklin et al., "A Constitutive Decay Element Promotes Tumor Necrosis Factor Alpha mRNA Degradation via an AU-Rich Element-Independent Pathway", *Molecular and Cellular Biology*, 23(10):3506-3515 (2003).

Trotta et al., "BCR/ABL Activates mdm2 mRNA Translation via the La Antigen", *Cancer Cell*, 3:145-160 (2003).

DeJong, Eric S., et al., "RNA and RNA-Protein Complexes as Targets for Therapeutic Intervention", *Current Topics in Medicinal Chemistry 2002*, vol. 2, No. 3, pp. 289-302.

Ismail, Said, et al., "Split-Intron Retroviral Vectors: Enhanced Expression with Improved Safety", *J. Virol.*, vol. 74, No. 5, pp. 2365-2371, Mar. 2000.

Ge et al., "Regulation of Promoter Activity of the APP Gene by Cytokines and Growth Factors", *Ann. N.Y. Acad. Sci.* 973:463-467 (2002).

Adams et al., 1991, "Fluorescence ratio imaging of cyclic AMP in single cells" Nature 349:694-697.

Afouda et al., 1999, "Localized XId3 mRNA activation in *Xenopus* embryos by cytoplasmic polyadenylation" Mech Dev 88(1):15-31.

Aharon & Schneider, 1993, "Selective destabilization of short-lived mRNAs with the granulocyte-macrophage colony-stimulating factor AU-rich 3' noncoding region is mediated by a cotranslational mechanism" Mol. Cell. Biol. 13: 197-980.

Akashi et al., 1994, "Number and location of AUUUA motifs: Role in regulating transiently expressed RNAs." Blood 83:3182-3187 Am Soc. of Hemat.

Amara et al., 1999, "TGF-beta(1), regulation of Alzheimer amyloid precursor protein mRNA expression in a normal human astrocyte cell line: mRNA stabilization." Brain Res. Mol. Brain Res. 71(1):42-49.

Asano et al., 1997, "The translation initiation factor eIF3-p48 subunit is encoded by int-6, a site of frequent integration by the mouse mammary tumor virus genome." J Biol. Chem. 272(38):23477-80.

Auwerx, 1991, "The human leukemia cell line, THP-1: A multifaceted model for the study of monocyte-macrophage differentiation." Experientia 47:22-31 Birkhauser Verlag Basel.

Bardoni & Mandel, 2002, "Advances in understanding of fragile X pathogenesis and FMRP function, and in identification of X linked mental retardation genes." Curr. Opin. Genet. Dev. 12(3):284-293.

Barkoff et al., 2000, "Translational control of cyclin B1 mRNA during meiotic maturation: coordinated repression and cytoplasmic polyadenylation" Dev Biol. 220(1):97-109.

Bashaw & Baker, 1995, "The msl-2 dosage compensation gene of *Drosophila* encodes a putative DNA-binding protein whose expression is sex specifically regulated by Sex-lethal." Develop. 121(10):3245-3258.

Beelman & Parker, 1994, "Differential effects of translational inhibition in cis and in trans on the decay of the unstable yeast MFA2 mRNA." J. Biol. Chem, 269:9687-9692.

Benjamin et al., 1997, "Conditional switching of vascular endothelial growth factor (VEGF) expression in tumors: induction of endothelial cell shedding and regression of hemangioblastoma-like vessels by VEGF withdrawal." Proc. Natl. Acad Sci 94:8761-8766.

Bergsten & Gavis, 1999, "Role for mRNA localization in translational activation but not spatial restriction of nanos RNA." Develop. 126(4):659-669.

(56) References Cited

OTHER PUBLICATIONS

Beutler et al., 1988, "Assay of ribonuclease that preferentially hydrolyses mRNAs containing cytokine-derived UA-rich instability sequences." Biochem. Biophys Res. Commun. 152:973-980.
Bock et al., 1992, "Selection of single-stranded DNA molecules that bind and inhibit human thrombin." Nature 355:564-566.
Brenchley, 1998, "Antagonizing the expression of VEGF in pathological angiogenesis," Exp. Opin Ther. Patents 8(12): 1695-1706.
Brennan & Steitz, 2001, "HuR and mRNA stability." Cell. Mol. Life. Sci. 58:266-277.
Cao, "Develop New cancer drugs that control VEGF expression: VEGF is an endothelial cell specific mitogen." Grant Application.
Cao, "Targeting VEGF 5' and 3' UTRS for tumor therapy: generation of stable cell lines for High Throughput screening."
Carballo et al., 1998, "Feedback inhibition of macrophage tumor necrosis factor-alpha production by tristetraprolin." Science 281:1001-1005.
Castagnetti et al., 2000, "Control of oskar mRNA translation by Bruno in a novel cell-free system from *Drosophila* ovaries." Develop. 127(5):1063-1068.
Charlesworth et al., 2000, "The temporal control of Weel mRNA translation during *Xenopus* oocyte maturation is regulated by cytoplasmic polyadenylation elements within the 3'-untranslated region." Dev. Biol. 227(2): 706-719.
Chen et al., 1994, "Interplay of two functionally and structurally distinct domains of the c-fos AU-rich element specifies its mRNA-destabilizing function." Mol. Cell. Biol. 14:416-426.
Chen et al., 1994, "Selective degradation of early-response-gene mRNAs: Functional analyses of sequence features of the AU-rich elements." Mol. Cell. Biol. 14: 8471-8482.
Chen et al., 1995, "AU-rich elements: characterization and importance in mRNA degradation" Trends Biochem. Sci. 20:465-470.
Chen et al., 1995, "mRNA decay mediated by two distinct AU-rich elements from c-fos and granulocyte-macrophage colony-stimulating factor transcripts: different deadenylation kinetics and uncoupling from translation." Mol. Cell. Biol. 15:5777-5788.
Chen et al., 2001, "AU binding proteins recruit the exosome to degrade ARE-containing mRNAs" Cell 107:451-464.
Cho et al., 2002, "Emerging techniques for the discovery and validation of therapeutic targets for skeletal diseases" Expert Opin. Ther. Targets 6(6):679-689.
Claffey et al., 1998, "Identification of a human VPF/VEGF 3' untranslated region mediating hypoxia-induced mRNA stability." Mol. Biol. of Cell. 9:469-481.
Clark et al., 2000, "Synthesis of the posterior determinant Nanos is spatially restricted by a novel cotranslational regulatory mechanism." Curr. Biol. 10(20):1311-1314.
Clark et al., 2002, "A common translational control mechanism functions in axial patterning and neuroendocrine signaling in *Drosophila*." Develop. 129(14): 3325-3334.
Cohen et al., 1996, "CN1-1493 inhibits monocyte/macrophage tumor necrosis factor by suppression of translation efficiency." Proc. Natl. Acad. Sci. USA 93:3967-3971.
Crawford et al., 1997, "The role of 3' poly (A) tail metabolism in tumor necrosis factor-α regulation," J. Biol. Chem. 272:21120-21127. The Am Soc of Biochem. and Molec. Biol.
Crosio et al., 2000, "La protein has a positive effect on the translation of TOP mRNAs in vivo." Nucl. Acids. Res. 28(15):2927-34.
Crucs et al., 2000, "Overlapping but distinct RNA elements control repression and activation of nanos translation." Mol. Cell. 5(3):457-467.
Curatola et al., 1995, "Rapid degradation of AU-rich element (ARE) mRNAs is activated by ribosome transit and blocked by secondary structure at any position 5' to the ARE." Mol. Cell. Biol. 15:6331.
Dahanukar & Wharton, 1996, "The Nanos gradient in *Drosophila* embryos is generated by translational regulation." Genes Dev 20:2610-2620.
Danner et al., 1998, "Agonist regulation of human beta$_2$-adrenergic receptor mRNA stability occurs via a specific AU-rich element," J. Biol. Chem. 273(6):3223-3229.

Database WPI Week, 2002, "Screening drug improving insulin resistance without exacerbating diabetic retinopathy, by detecting expression of reporter gene fused to promoter region of human vascular endothelial growth factor gene in mammal cell." JP 2001 340080 A.
Dias et al., 1994, "Chemical probe for glycosidic conformation in telomeric DNAs" J. Am. Chem. Soc. 116:4479-4480.
Diener & Moore, 1998, "Solution structure of a substrate for the archael pre-tRNA splicing endonucleases: The bulge-helix-bulge motif." Mol. Cell. 1:883-894.
Dominski & Marzluff, 1999, "Formation of the 3' end of histone mRNA." Gene 239(1):1-14.
Eibl et al., 1999, "In vivo analysis of plastid psbA, rbcL and rpl32 UTR elements by chloroplast transformation: tobacco plastid gene expression is controlled by modulation of transcript levels and translation efficiency", Plant J. 19:333-345.
Fan et al., 1998, "Overepxression of HuR, a nuclear-cytoplasmic shuttling protein, increases the in vivo stability of ARE-containing mRNAS." EMBO J 17:3448-3460.
Fruscoloni et al., 2001, "Cleavage of non-tRNA substrates by eukaryal tRNA splicing endonucleases." EMBO Rep 2(3):217-221.
Gan et al., 1998, "Functional characterization of the internal ribosome entry site of eIF4G mRNA" J. Biol. Chem. 273:5006-5012.
Gavis et al., 1996, "A conserved 90 nucleotide element mediates translational repression of nanos RNA. Development. Sep. 1996;122(9):2791-800." Develop. 122(9):2791-2800.
Gebauer et al., 1998, "The *Drosophila* splicing regulator sex-lethal directly inhibits translation of male-specific-lethal 2 mRNA" RNA 4(2):142-150.
GenBank Accession No. AF022375, dated Oct. 7, 1998.
GenBank Accession No. AJ131730, dated Apr. 15, 2005.
GenBank Accession No. M11567, dated Oct. 30, 1994.
GenBank Accession No. M14745, dated Apr. 27, 1993.
GenBank Accession No. M14758, dated Dec. 3, 1999.
GenBank Accession No. M33680, dated Aug. 3, 1993.
GenBank Accession No. M54968, dated Feb. 4, 1997.
GenBank Accession No. M90100, dated Dec. 31, 1994.
GenBank Accession No. NM_0002 30, dated Mar. 5, 2006.
GenBank Accession No. NM_0001 62, dated Jan. 15, 2006.
GenBank Accession No. NM_000134, dated Oct. 15, 2006.
GenBank Accession No. NM_0002 08, dated Feb. 24, 2006.
GenBank Accession No. NM_0002 47, dated Feb. 27, 2006.
GenBank Accession No. NM_0003 21, dated Mar. 5, 2006.
GenBank Accession No. NM_0004 18, dated Feb. 12, 2006.
GenBank Accession No. NM_0005 27, dated Jan. 15, 2006.
GenBank Accession No. NM_0005 72, dated Mar. 5, 2006.
GenBank Accession No. NM_0005 89, dated Mar. 5, 2006.
GenBank Accession No. NM_0006 65, dated Feb. 28, 2006.
GenBank Accession No. NM_000600, dated Mar. 5, 2006.
GenBank Accession No. NM_0007 58, dated Feb. 12, 2006.
GenBank Accession No. NM_0007 84, dated Nov. 27, 2005.
GenBank Accession No. NM_0007 91, dated Nov. 6, 2005.
GenBank Accession No. NM_0007 99, dated Jan. 29, 2006.
GenBank Accession No. NM_000794, dated Sep. 17, 2006.
GenBank Accession No. NM_0008 99, dated Nov. 27, 2005.
GenBank Accession No. NM_0008 ev 75, dated Apr. 10, 2009.
GenBank Accession No. NM_0009 48, dated Feb. 26, 2006.
GenBank Accession No. NM_0011 45, dated Mar. 5, 2006.
GenBank Accession No. NM_001168, dated Mar. 5, 2006.
GenBank Accession No. NM_0012 40, dated Feb. 26, 2006.
GenBank Accession No. NM_0015 65, dated Jan. 29, 2006.
GenBank Accession No. NM_0015 67, dated Jan. 29, 2006.
GenBank Accession No. NM_0017 28, dated Feb. 26, 2006.
GenBank Accession No. NM_0017 ev 25, dated Oct. 22, 2006.
GenBank Accession No. NM_001917, dated Jan. 29, 2006.
GenBank Accession No. NM_002006, dated Oct. 1, 2006.
GenBank Accession No. NM_002087, dated Oct. 18, 2005.
GenBank Accession No. NM_0021 11, dated Feb. 19, 2006.
GenBank Accession No. NM_0021 51, dated Jan. 8, 2006.
GenBank Accession No. NM_002231, dated Nov. 27, 2005.
GenBank Accession No. NM_002392, dated Mar. 5, 2006.
GenBank Accession No. NM_0026 ev 32, dated Aug. 20, 2006.
GenBank Accession No. NM_0027 74, dated Feb. 12, 2006.

(56) References Cited

OTHER PUBLICATIONS

GenBank Accession No. NM_0029 63, dated Feb. 26, 2006.
GenBank Accession No. NM_0029 86, dated Nov. 6, 2005.
GenBank Accession No. NM_0029 ev 25, dated Aug. 20, 2006.
GenBank Accession No. NM_0029 ev 64, dated Oct. 22, 2006.
GenBank Accession No. NM_0032 55, dated Mar. 4, 2006.
GenBank Accession No. NM_0032 56, dated Mar. 4, 2006.
GenBank Accession No. NM_0033 55, dated Jan. 29, 2006.
GenBank Accession No. NM_0036 42, dated Sep. 24, 2005.
GenBank Accession No. NM_0038 ev 83, dated Oct. 29, 2006.
GenBank Accession No. NM_004364, dated Jan. 29, 2006.
GenBank Accession No. NM_004395, dated Oct. 16, 2005.
GenBank Accession No. NM_0047 95, dated Feb. 26, 2006.
GenBank Accession No. NM_0047 97, dated Mar. 5, 2006.
GenBank Accession No. NM_0052 51, dated Feb. 12, 2006.
GenBank Accession No. NM_0052 52, dated Jan. 29, 2006.
GenBank Accession No. NM_0054 ev 17, dated Apr. 19, 2009.
GenBank Accession No. NM_0059 31, dated Oct. 16, 2005.
GenBank Accession No. NM_006536, dated Sep. 17, 2006.
GenBank Accession No. NM_007310, dated Jan. 29, 2006.
GenBank Accession No. NM_0187 ev 27, dated Mar. 1, 2009.
GenBank Accession No. NM_0204 15, dated Jan. 29, 2006.
GenBank Accession No. NM_0326 11, dated Mar. 4, 2006.
GenBank Accession No. NM_053056, dated Feb. 26, 2006.
GenBank Accession No. NM_0784 67, dated Mar. 5, 2006.
GenBank Accession No. NM_0807 04, dated Mar. 2, 2006.
GenBank Accession No. NM_0807 05, dated Mar. 2, 2006.
GenBank Accession No. NM_0807 06, dated Mar. 2, 2006.
GenBank Accession No. NM_080881, dated Oct. 17, 2005.
GenBank Accession No. NM_138712, dated Mar. 5, 2006.
GenBank Accession No. NM_1389 92, dated Feb. 12, 2006.
GenBank Accession No. NM_1393 ev 17, dated Oct. 29, 2006.
GenBank Accession No. S48568, dated Apr. 17, 2002.
GenBank Accession No. U22431, dated Jun. 28, 1995.
GenBank Accession No. U25676, dated Jul. 20, 1995.
GenBank Accession No. X00588.1, dated Mar. 30, 1995.
GenBank Accession No. X01394, dated Mar. 21, 1995.
GenBank Accession No. X16302, dated Apr. 18, 2005.
GenBank Accession No. XM_001831, dated May 8, 2002.
GenBank Accession No. XM_003061, dated May 8, 2002.
GenBank Accession No. XM_003751, dated Oct. 16, 2001.
GenBank Accession No. XM 015547, dated Aug. 1, 2002.
GenBank Accession No. XM 589987, dated Sep. 30, 2005.
Gil et al., 1996, "Multiple regions of the *Arabidopsis* SAUR-AC1 gene control transcript abundance: the 3' untranslated region functions as an mRNA instability determinant." EMBO J 15:1678-1686.
Goodwin et al., 1993, "Translational regulation of tra-2 by its 3' untranslated region controls sexual identity in *C. elegans*." Cell 75:329-339.
Goodwin et al., 1997, "A genetic pathway for regulation of tra-2 translation" Develop. 124:749-758.
Green et al., 2002, "Crystallization and characterization of Smaug: a novel RNA-binding motif." Biochem. Biophys. Res. Commun. 297(5):1085-1088.
Guhaniyogi & Brewer, 2001, "Regulation of mRNA stability in mammalian cells." Gene 265(1-2):11-23.
Haag & Kimble, 2000, "Regulatory elements required for development of *Caenorhabditis elegans* hermaphrodites are conserved in the tra-2 homologue of *C. remanei*, a male/female sister species" Genetics 155(1):105-116.
Heaton et al., 1998, "Cyclic nucleotide regulation of type-1 plasminogen activator-inhibitor mRNA stability in rat hepatoma cells. Identification of cis-acting sequences." J Biol. Chem. 273:14261-14268.
Hubert et al., 1996, "RNAs mediating cotranslational insertion of selenocysteine in eukaryotic selenoproteins" Biochimie 78(7):590-596.
Hyder et al., 2000, "Identification of functional estrogen response elements in the gene coding for the potent angiogenic factor vascular endothelial growth factor," Cancer Res 60:3183-3190.

Iida et al., 2002, "Vascular endothelial growth factor gene expression in a retinal pigmented cell up-regulated by glucose deprivation through 3' UTR." Life Sciences 71:1607-1614.
Ikemura and Okeki, 1983, "Codon usage and transfer RNA contents: organism-specific codon-choice patterns in reference to the isoacceptor contents." Cold Spring Harbor Symp. Quant. Biol. 47:1087-1097.
Ikemura, 1985, "Codon usage and tRNA content in unicellular and multicellular organisms." Mol. Biol. Evol., 2(1):13-34.
Jan et al., 1997, "Conservation of the *C. elegans* tra-2 3'UTR translational control." EMBO J 16(20):6301-6313.
Jan et al., 1999, "The STAR protein, GLD-1, is a translational regulator of sexual identity in *Caenorhabditis elegans*." EMBO J. 18:258-269.
Kakegawa et al., 2002, "Rapamycin induces binding activity to the terminal oligopyrimidine tract of ribosomal protein mRNA in rats." Arch Biochem Biophys 402(1):77-83.
Kastelic et al., 1996, "Induction of rapid IL-1 beta mRNA degradation in THP-1 cells mediated through the AU-rich region in the 3'UTR by a radicicol analogue." Cytokine 8: 751-761.
Keene & Tenenbaum, 2002, "Eukaryotic mRNPs may represent post-transcriptional operons" Mol. Cell. 9:1161-1167.
Kelly et al., 1996, "Reconciliation of the X-ray and NMR structures of the thrombin-binding aptamer d(GGTTGGTGTGGTTGG)." J. Mol. Biol. 256:417-422.
Kemeny et al., 1998, "The tetravalent guanylhydrazone CN1-1493 blocks the toxic effects of interleukin-2 without diminishing antitumor efficacy." Proc. Natl. Acad. Sci. USA 95: 4561-4566.
Kim et al., 2002, "The human elongation factor 1 alpha (EF-1 alpha) first intron highly enhances expression of foreign genes from the murine cytomegalovirus promoter." J. Biotechnol. 93(2):183-187.
Kimble, 1988, "fog-2, a germ-line-specific sex determination gene required for hermaphrodite spermatogenesis in *Caenorhabditis elegans*." Genetics, 119:43-61.
Klausner et al., 1993, "Regulating the fate of RNA: The control of cellular iron metabolism" Cell 72:19-28.
Kleman-Leyer et al., 1997, "Properties of *H. volcanii* tRNA intron endonuclease reveal a relationship between the archaeal and eucaryal tRNA intron processing systems." Cell., 89:839-847.
Kobayashi et al., 1998, "Characterization of the 3' untranslated region of mouse DNA topoisomerase 11α mRNA," Gene 215:329-337.
Koeller et al., 1991, "Translation and the stability of mRNAs encoding the transferrin receptor and c-fos." Proc. Natl. Acad. Sci. 88:7778.
Lagnado et al., 1994, "AUUUA is not sufficient to promote Poly(A) shortening and degradation of an mRNA: the functional sequence within the AU-rich elements may be UUAUUUA(U/A) (U/A)" Mol. Cell. Biol. 14: 7984-7995.
Le & Maizel, 1989, "A method for assessing the statistical significance of RNA folding" J. Theor Biol. 138:495-510.
Levy et al., 1995, "Sequence and functional characterization of the terminal exon of the human insulin receptor gene." Biochem Biophys Acta 1263:253-257.
Levy et al., 1996, "Post-transcriptional regulation of vascular endothelial growth factor by hypoxia." J. Biol. Chem. 271:2746-2753.
Levy et al., 1998, "Hypoxic stabilization of vascular endothelial growth factor mRNA by the RNA-binding protein HuR." J Biol. Chem. 273(11):6417-6423.
Lewis et al., 1998, "Mapping of a minimal AU-rich sequence required for lipopolysaccharide-induced binding of a 55-kDa protein on tumor necrosis factor-α mRNA." J Biol. Chem. 273:13781-13786.
Li & Abelson, 2000, "Crystal structure of a dimeric archaeal splicing endonuclease." J. Mol. Biol. 302:639-648.
Li et al., 1998, "Crystal structure and evolution of a transfer RNA splicing enzyme" Science 280(5361):279-284.
Li et al., 2001, "Targeting HER-2/neu-overexpressing breast cancer cells by an antisense iron responsive element-directed gene expression." Cancer Letters 174(2):151-58.
Lykke-Andersen, J. & Garrett, R.A.., 1997, "RNA-protein interactions of an archaeal homotetrameric splicing endoribonuclease with an exceptional evolutionary history." EMBO J 16(20):6290-6300.
Macaya et al., 1993, "Thrombin-binding DNA aptamer forms a unimolecular quadruplex structure in solution." Proc. Natl. Acad. Sci. 90:3745-3749.

(56) References Cited

OTHER PUBLICATIONS

Muhlrad et al., 1995, "Turnover mechanisms of the stable yeast PGK1 mRNA." Mol. Cell. Biol. 15(4):2145-2156.
Mukherjee et al., 2002, "The mammalian exosome mediates the efficient degradation of mRNAs that contain AU-rich elements." EMBO J. 21:165-174.
Nanbru et al., 1995, "Alternative translation of the proto-oncogenc c-myc by an internal ribosome entry site." J. Biol. Chem. 272:32061-32066.
Nanbu et al., 1994, "Multiple instability-regulating sites in the 3' untranslated region of the urokinase-type plasminogen activator mRNA." Mol. Cell. Biol. 14:4920-4928.
Oh et al., 1992, "Homeotic gene Antennapedia mRNA contains 5'-noncoding sequences that confer translational initiation by internal ribosome binding." Genes Dev 6:1643-1653.
Ostareck-Lederer et al., 2002, "c-Src-mediated phosphorylation of hnRNP K drives translational activation of specifically silenced mRNAs" Mol. Cell. Biol. 22(13):4535-4543.
Paynton & Bachvarova, 1994, "Polyadenylation and deadenylation of maternal mRNAs during oocyte growth and maturation in the mouse" Mol. Reprod. Dev 37(2): 172-180.
Pelletier & Soneberg, 1988, "Internal initiation of translation of eukaryotic mRNA directed by a sequence derived from poliovirus RNA" Nature 334:320-325.
Peterlin et al., 1993, "Tat Trans-Activator." In: Human Retroviruses; Cullen, Ed.; Oxford University Press: New York, pp. 75-100.
Piecyk et al., 2000, "TIA-1 is a translationa silencer that selectively regulates the expression of TNF-alpha" EMBO J. 19:4154.
Qin & Pyle, 1999, "Site-specific labeling of RNA with fluorophores and other structural probes." Methods 18 (1):60-70.
Rajagopalan & Malter, 2000, "Growth factor-mediated stabilization of amyloid precursor protein mRNA is mediated by a conserved 29-nucleotide sequence in the 3'-untranslated region." J. Neurochem. 74(1):52-59.
Rapella et al., 2002, "Flavopiridol inhibits vascular endothelial growth factor production induced by hypoxia or picolinic acid in human neuroblastoma." Int. J. Cancer 99:658-664.
Raught et al. 2000, "Regulation of ribosomal recruitment in eukaryotes" in: "Translational Control of Gene Expression." Sonenberg, Hershey and Mathews, eds. Cold Spring Harbor Laboratory Press, Ch. 6. pp. 245-293.
Reinmann et al., 2002, "Suppression of 15-lipoxygenase synthesis by hnRNP E1 is dependent on repetitive nature of LOX mRNA 3'-UTR control element DICE." J. Mol. Biol 315(5):965-974.
Reyes & Abelson 1988, "Substrate recognition and splice site determination in yeast tRNA splicing." Cell 55:719-730.
Rogers et al., 2002, "An iron-responsive element typeII in the 5'-untranslated region of the Alzheimer's amyloid precursor protein transcript." J. Biol. Chem. 277(47):45518-45528.
Sachs, 1993, "Messenger RNA degradation in eukaryotes." Cell 74:413-421.
Sambrook et al., 1989, "Standard protocol for calcium phosphate-mediated transfection of adherent cells," Molec. Cloning 16.33-16.37.
Sarkar & Hopper, 1998, "tRNA nuclear export in *Saccharomyces cerevisiae*: In situ hybridization analysis." Mol. Biol. Cell 9:3041-3055.
Savant-Bhonsale et al., 1992, "Evidence for instability of mRNAs containing AUUUA motifs mediated through translation-dependent assembly of a > 20S degradation complex" Genes Dev. 6:1927-1939.
Saxena et al., 1992, "Angiogenin is a cytotoxic, tRNA-specific ribonuclease in the RNase A superfamily." J. Biol. Chem. 267(30):21982-21986.
Schlatter & Fussenegger, 2003. "Novel CNBP- and La-based translation control systems for mammalian cells." Biotechnol Bioeng. 81(1):1-12.
Schultze et al., 1994, "Three-dimensional solution structure of the thrombin-binding DNA aptamer d(GGTTGGTGTGGTTGG)." J. Mol. Biol. 235:1532-1547.

Shaw & Kamen, 1986, "A conserved AU sequence from the 3' untranslated region of GM-CSF mRNA mediates selective mRNA degradation." Cell 46:659-667.
Shyu et al., 1991, "Two distinct destabilizing elements in the c-fos message trigger deadenylation as a first step in rapid mRNA decay." Genes Dev 5:221-231.
Stebbins-Boaz et al., 1996, "CPEB controls the cytoplasmic polyadenylation of cyclin, Cdk2 and c-mos mRNAs and is necessary for oocyte maturation in *Xenopus*." EMBO J. 15(10):2582-2592.
Stein et al., 1998, "Translation of vascular endothelial growth factor mRNA by internal ribosome entry: implications for translation under hypoxia" Mol. Cell. Biol. 18:3112-3119.
Stoecklin et al., 1994, "Functional Hierarchy of AUUUA Motifs in Mediating Rapid Interleukin-3 mRNA decay." J Biol. Chem. 269:28591-28597.
Stolle et al., 1988, "Cellular Factor affecting the stability of β-globin mRNA." Gene 62:65-74.
Stoneley, 1998, "C-Myc 5' untranslated region contains an internal ribosome entry segment" Oncogene 16:423-428.
Sullivan et al., 1996, "Mutational analysis of the DST element in tobacco cells and transgenic plants: Identification of residues critical for mRNA instability," RNA 2:308-315.
Tay et al., 2000,, "The control of cyclin B1 mRNA translation during mouse oocyte maturation." Dev. Biol. 221(I):1-9.
Thiele et al., 1999, "Express on of leukocyte-type 12-lipoxygenase and reticulocyte-type 15-lipoxygenase in rabbits" Adv Exp Med Biol. 447:45-61.
Tholanikunnel & Malborn, 1997, "A 20-nucleotide (A + U)-rich element of beta2-adrenergic receptor (beta2AR) mRNA mediates binding to beta2AR-binding protein and is obligate for agonist-induced destabilization of receptor mRNA." J. Biol. Chem. 272:11471.
Thompson et al., 2000, "Rapid deadenylation and Poly(A)-dependent translational repression mediated by the *Caenorhabditis elegans* tra-2 3' untranslated region in *Xenopus* embryos." Mol. Cell. Biol. 20(6):2129-2137.
Trifillis et al., 1999, "Finding the right RNA: identification of cellular mRNA substrates for RNA-binding proteins." RNA 5:1071-1082.
Trotta et al., 1997, "The yeast tRNA splicing endonuclease: a tetrameric enzyme with two active subunits homologous to the archaeal tRNA endonucleases," Cell 89:849-858.
Trotta, "Gene Expression" Revised Background Draft.
Trotta., 1999, "The Composition, Function and Evolution of tRNA Splicing Endonuclease." Thesis, California Institute of Technology, pp. 1-147.
Vagner et al., 1995, "Alternative translation of human fibroblast growth factor 2 mRNA occurs by internal entry of ribosomes." Mol. Cell. Biol. 15:35-44.
Vagner et al., 2001, "Irresistible IRES. Attracting the translation machinery to internal ribosome entry sites." EMBO Reports 2:893.
Volarevic et al., 2000, "Proliferation, but not growth blocked by conditional deletion of 40S ribosomal protein S6." Science 288:2045-2047.
Wang et al., 1993, "A DNA aptamer which binds to and inhibits thrombin exhibits a new structural motif for DNA." Biochem. 32(8):1899-1904.
Wells et al., 1998, "Circularization of mRNA by eukaryotic translation initiation factors." Mol. Cell. 2:135-140.
Westmark & Malter, 2001, "Extracellular-regulated kinase controls beta-amyloid precursor protein mRNA decay" Brain Res Mol. Brain. Res 90(2):193-201.
Wilkund et al., 2002, "Inhibition of translation by UAUUUAU and UAUUUUUAU motifs of the AU-rich RNA instability element in the HPV-1 late 3' untranslated region." J. Biol. Chem. 277:40462.
Winstall et al., 1995, "Rapid mRNA degradation mediated by the c-fos 3' AU-rich element and that mediated by the granulocyte-macrophage colony-stimulating factor 3' AU-rich element occur through similar polysome-associated mechanisms" Mol. Cell. Biol. 15:3796-3804.
Worthington et al., 2002, "RNA binding properties of the AU-rich element-binding recombinant Nup475/TIS11/tristetraprolin protein." J. Biol. Chem. 277: 48558-48564.

(56) References Cited

OTHER PUBLICATIONS

Xu et al., 1997, "Modulation of the fate of cytoplasmic mRNA by AU-rich elements: key sequence features controlling mRNA deadenylation and decay." Mol. Cell. Biol. 17:4611-4621.
Yamazaki et al., 2003, "HIF-1 dependent VEGF reporter gene assay by a stable transformant of CHO cells." Bio & Pharm Bulletin. 26(4): 417-420.
Ye et al., 1997, "Ultrabithorax and Antennapedia 5' untranslated regions promote developmentally regulated internal translation initiation" Mol. Cell. Biol. 17:1714-1721.
Zaidi & Malter, 1995, "Nucleolin and heterogeneous nuclear ribonucleoprotein C proteins specifically interact with the 3'-untranslated region of amyloid protein precursor mRNA." J. Biol. Chem. 271(29):17292-17298.
Zhang et al., 1995, "Identification and characterization of a sequence motif involved in nonsense-mediated mRNA decay" Mol. Cell. Biol. 15:2231-2244.
Zhang et al., 1996, "An enhanced green fluorescent protein allows sensitive detection of gene transfer in mammalian cells." BBRC 227:707-711.
Zhang et al., 1997, "Gene expression profiles in normal and cancer cells." Science 276:1268-1272.
Zhu et al., 2001, "Binding of the La autoantigen to the 5' untranslated region of a chimeric human translation elongation factor 1A reporter mRNA inhibits translation in vitro," Biochim. Biophys Acta 1521(1-3):19-29.
Zubiaga et al., 1995, "The nonamer UUAUUUAUU is the key AU-rich sequence motif that mediates mRNA degradation," Mol. Cell. Biol. 15(4):2219-2230.
Requirement for Restriction/Election, dated Jan. 11, 2007 of U.S. Appl. No. 10/851,074, filed May 24, 2004.
Amendment and Response to Restriction/Election dated May 11, 2007 of U.S. Appl. No. 10/851,074, filed May 24, 2004.
Non Final Rejection dated Sep. 7, 2007 of U.S. Appl. No. 10/851,074, filed May 24, 2004.
Amendment and Response to Non-Final Rejection dated Mar. 4, 2008 of U.S. Appl. No. 10/851,074, filed May 24, 2004.
Non Final Rejection dated Jul. 10, 2008 of of U.S. Appl. No. 10/851,074, filed May 24, 2004.
Non Final Rejection dated Oct. 23, 2008 of of U.S. Appl. No. 10/851,074, filed May 24, 2004.
Amendment and Response to Non-Final Rejection dated Apr. 22, 2009 of U.S. Appl. No. 10/851,074, filed May 24, 2004.
Written Opinion of the International Searching Authority dated Jul. 14, 2008 in the PCT Application No. PCT/US04/01643 filed Jan. 21, 2004.
International Search Report dated Jul. 14, 2008 in the PCT Application No. PCT/US04/01643 filed Jan. 21, 2004.
International Search Report dated Jul. 13, 2005 in the PCT Application No. PCT/US04/26309 filed Aug. 16, 2004.
International Preliminary Report on Patentability, dated Jan. 23, 2007 in the PCT Application No. PCT/US04/26309 filed Aug. 16, 2004.
Written Opinion of the International Searching Authority dated Jul. 13, 2005 in the PCT Application No. PCT/US04/26309 filed Aug. 16, 2004.
International Preliminary Report on Patentability, dated Nov. 19, 2007 in the PCT Application No. PCT/US04/020751 filed Jun. 28, 2004.
Written Opinion of the International Searching Authority dated Jul. Nov. 6, 2007 in the PCT Application No. PCT/US04/020751 filed Jun. 28, 2004.
Supplemental European Search Report, dated Nov. 19, 2008, issued in EP 04809465.0 (EP1761638.
International Search Report dated Jul. 30, 2005 in the PCT Application No. PCT/US04/038496 filed Nov. 17, 2004.
Written Opinion, dated May 17, 2006 in the PCT Application No. PCT/US04/038496 filed Nov. 17, 2004.
Preliminary Amendment filed Oct. 23, 2006 in U.S. Appl. No. 10/543,033.
Restriction Requirement mailed May 16, 2008 in U.S. Appl. No. 10/543,033.
Response to Restriction Requirement filed Nov. 17, 2008 in U.S. Appl. No. 10/543,033.
Office Action mailed Feb. 20, 2009 in U.S. Appl. No. 10/543,033.
Response to Pre-Exam Formalities Notice, dated Sep. 15, 2006 of U.S. Appl. No. 10/579,500, filed Mar. 29, 2007.
Restriction/Election Requirement, dated Jan. 26, 2009 of U.S. Appl. No. 10/579,500, filed Mar. 29, 2007.
Cohen et al., 1996, "Interleukin 6 induces the expression of vascular endothelial growth factor." J. Biol Chem. 271(12):736-741.
Zhang et al., 2000, "Wild-type p53 suppresses angiogenesis in human leiomyosarcoma and synovial sarcoma by transcriptional suppression of vascular endothelial growth factor expression." Cancer Res 60:3655-3661.
Supplemental Partial European Search Report, dated Nov. 5, 2009, issued in EP 04704085.2 (EP 1604011).
Response to Non-Final Rejection filed Jul. 17, 2009 in U.S. Appl. No. 10/543,033.
Final Rejection, dated Aug. 4, 2009, in U.S. Appl. No. 10/851,074.
Child et al., 1999, "Cell-type dependent and -independent control of HER-2/neu translation." Int J. Biochem & Cell Biol. 31:201-213.
Hoover et al., 1997, "Pim-1 protein expression is regulated by its 5'-untranslated region and translation initiation factor eIF-4E", Cell Growth Differ., 8: 1371-1380.
Horvath et al., "Multiple elements in the 5' untranslated region down-regulate c-sis messenger RNA translation", Cell Growth & Diff., 6: 1103-1110.
Kowalski and Mager, 1998, "A human endogenous retrovirus suppresses translation of an associated fusion transcript, PLA2L", J. Virol., 72(7):6164-8.
Mehta et al., 2006, "Depresssion of the HER-2 uORF is mediated by a novel post-transcriptional control mechanism in cancer cells." Genes & Dev. 20:939-953.
Pettetier & Soneberg, 1988, "Internal initiation of translation of eukaryotic mRNA directed by a sequence derived from poliovirus RNA." Nature 334:320-325.
Pontrelli et al., 2004, "Translational control of apolipoprotein B mRNA: regulation via cis elements in the 5' and 3' untranslated regions", Biochemistry, 43(21):6734-44.
Sachs & Geballe, 2006, "Downstream control of upstream open reading frames." Genes & Dev. 20:915-921.
Communication from the Examining Division, dated Jan. 29, 2010, issued in EP 04704085.2 (EP 1604011).
Response to Restriction/Election Requirement, dated Jun. 26, 2009, in U.S. Appl. No. 10/579,500.
Restriction/Election Requirement, dated Aug. 6, 2009, in U.S. Appl. No. 10/579,500.
Response to Restriction/Election Requirement, dated Sep. 4, 2009, in U.S. Appl. No. 10/579,500.
Non-Final Rejection, dated Jan. 5, 2010, in U.S. Appl. No. 10/579,500.
Final Rejection, dated Aug. 24, 2009, in U.S. Appl. No. 10/851,074.
Response to Final Rejection and Request for Continued Examination, dated Nov. 24, 2009, in U.S. Appl. No. 10/851,074.
Non-Final Rejection, dated Jun. 24, 2010, in U.S. Appl. No. 10/851,074.
Lal et al., 2004, "Concurrent Versus Individual Binding of HuR and AUF1 to Common Labile Target mRNA's" EMBO J. 23:3092-3102.
Millard et al., 2000, "A U-Rich Element in the 5' Untranslated Region if necessary for the Translation of p27 mRNA" Molec & Cell. Biol. 20(16):5947-5959.
Morris et al., 2000, "Upstream Open Reading Frames as Regulators of mRNA translation," Molec & Cell. Biol. 20(23):8635-8642.
Pesole et al., 2001, "Structural and Functional Features of Eukaryotic mRNA Untranslated Regions." Gene 276:73-81.
International Search Report, dated Jun. 2, 2005, in the PCT Application No. PCT/US04/038496.
International Preliminary Report on Patentability, dated Jul. 17, 2008, in the PCT Application No. PCT/US04/038496.
Response to Non-final rejection, dated Jul. 17, 2009, in U.S. Appl. No. 10/543,033.
Final Rejection, dated Jan. 13, 2010, in U.S. Appl. No. 10/543,033.

(56) References Cited

OTHER PUBLICATIONS

Amendment after Final, dated Jul. 13, 2010, in U.S. Appl. No. 10/543,033.
Non-Final Rejection, dated Feb. 4, 2011 in U.S. Appl. No. 10/543,033.
Non-Final Rejection, dated Jan. 25, 2011 in U.S. Appl. No. 10/851,074.
Response to Office Action, dated Jun. 27, 2011 in U.S. Appl. No. 10/851,074.
Adams et al., 1998, "Localized infusion of IGF-1 results in skeletal muscle hypertrophy in rats." J Appl Physiol, 84:1716-1722.
Barton et al., 2002, "Muscle-specific expression of insulin-like growth factor I counters muscle decline in mdx mice", J. Cell Biol., 157:137-148.
Barton-Davis, 1998, "Viral mediated expression of insulin-like growth factor I blocks the aging-related loss of skeletal muscle function", PNAS, 95:15603-15607.
Bogdanovich et al., 2004, "Therapeutics for Duchenne muscular dystrophy: current approaches and future directions", J Mol Med., 82(2):102-15.
Burkin and Kaufman, 1999, "The $\alpha 7\beta 1$ integrin in muscle development and disease", Cell Tissue Res., 296:183-190.
Chakkalakal et al., 2005, "Molecular, cellular, and pharmacological therapies for Duchenne/Becker muscular dystrophies", FASEB J., 19(8):880-91.
Coleman et al., 1995, "Myogenic Vector Expression of Insulin-like Growth Factor I Stimulates Muscle Cell Differentiation and Myofiber Hypertrophy in Transgenic Mice", J. Biol. Chem., 270:12109-12116.
Davies and Nowak, 2006, "Molecular Mechanisms of Muscular Dystrophies: Old and New Players", Nature, 7:762-773 (Supplementary Information Included).
Engvall et al., 2003, "The new frontier in muscular dystrophy research: booster genes", FASEB J., 17: 1579-1584.
Gramolini et al., 2001, "Distinct regions in the 3' untranslated region are responsible for targeting and stabilizing utrophin transcripts in skeletal muscle cells", J Cell Biol, 154:1173-1183.
Gramolini, 2001, "Increased expression of utrophin in a slow vs. a fast muscle involves posttranscriptional events", Am J Physiol Cell Physiol., 281(4):C1300-9.
Kambadur et al., 1997, "Mutations in myostatin (GDF8) in double-muscled Belgian Blue and Piedmontese cattle", Genome Res., 7(9):910-6.
Karin et al., 2006, "Role for IKK2 in muscle: waste not, want not", J Clin Invest., 116: 2866-2868.
Krag et al., 2004, "Heregulin ameliorates the dystrophic phenotype in *mdx* mice", PNAS, 101: 13856-13860.
Nowak and Davies, 2004, "Duchenne Muscular Dystrophy and dystrophin: pathogenesis and opportunities for treatment", EMBO Reports, 5:872-876.
Ohlendieck and Campbell, 1991, "Dystrophin-associated proteins are greatly reduced in skeletal muscle from mdx mice", J Cell Biol, 115:1685-1694.
Patel et al, 2005, "Molecular mechanisms involving IGF-1 and myostatin to induce muscle hypertrophy as a therapeutic strategy for Duchenne Muscular Dystrophy", Acta Myol., 24(3):230-41.
Tobin et al., 2005, "Myostatin, a negative regulator of muscle mass: implications for muscle degenerative diseases", Curr Opin Pharmacol., 5(3):328-32.
Vachon et al.,1997, "Integrins (alpha7beta1) in muscle function and survival. Disrupted expression in merosin-deficient congenital muscular dystrophy", J Clin Invest., 100(7):1870-81.
Veyrune et al., 1996, "A localisation signal in the 3' untranslated region of c-myc mRNA targets c-myc mRNA and beta-globin reporter sequences to the perinuclear cytoplasm and cytoskeletal-bound polysomes", J Cell Sci, 109:1185-1194.
Avila et al., 2007 "Trichostatin A increases SMN expression and survival in a mouse model of spinal muscular atrophy", J Clin Invest.; 117(3):659-71.

Bertini et al., 2005, "134th ENMC International Workshop: Outcome Measures and Treatment of Spinal Muscular Atrophy, Feb. 11-13, 2005, Naarden, The Netherlands", Neuromuscul Disord. 15(11):802-16.
Boda et al., 2004, "Survival motor neuron SMN1 and SMN2 gene promoters: identical sequences and differential expression in neurons and non-neuronal cells", Eur J Hum Genet.; 12(9):729-37.
Brahe et al., 2005, "Phenylbutyrate increases SMN gene expression in spinal muscular atrophy patients", Eur J Hum Genet.; 13(2):256-9.
Echaniz-Laguna et al., 1999, "The promoters of the survival motor neuron gene (SMN) and its copy (SMNc) share common regulatory elements", Am J Hum Genet; 64(5):1365-70.
Germain-Desprez et al., 2001, "The SMN genes are subject to transcriptional regulation during cellular differentiation", Gene, 279:109-117.
Iannaconne et al., 2002 "Outcome Measures for Pediatric Spinal Muscular Atrophy", Arch Neurol. 59:1445-1450.
Iannaconne et al., 2003, "Reliability of 4 Outcome Measures in Pediatric Spinal Muscular Atrophy", Arch Neurol; 60:1130-1136.
Jarecki et al., 2005 "Diverse small-molecule modulators of SMN expression found by high-throughput compound screening: early leads towards a therapeutic for spinal muscular atrophy", Hum Mol Genet.; 14(14):2003-18.
Kolb et al., 2006, "A novel cell immunoassay to measure survival of motor neurons protein in blood cells", BMC Neurology, 6:6.
Lunn et al., 2004, "Indoprofen upregulates the survival motor neuron protein through a cyclooxygenase-independent mechanism", Chem Biol.; 11(11):1489-93.
Merlini et al., 2003, "Role of gabapentin in spinal muscular atrophy: results of a multicenter, randomized Italian study", J Child Neurol.; 18(8):537-41.
Monani et al.. 1999, Promoter analysis of the human centromeric and telomeric survival motor neuron genes (SMNC and SMNT), Biochim Biophys Acta; 1445(3):330-6.
Sumner., 2006, "Therapeutics development for spinal muscular atrophy", NeuroRx.; 3(2):235-45.
Wan, 2005, "The survival of motor neurons protein determines the capacity for snRNP assembly: biochemical deficiency in spinal muscular atrophy", Molec & Cell Biol, 25(13): 5543-5551.
Wolstencroft et al., 2005, "A non-sequence-specific requirement for SMN protein activity: the role of aminoglycosides in inducing elevated SMN protein levels", Hum Mol Genet, 14(9):1199-1210.
Zhang et al., 2001, "An in vivo reporter system for measuring increased inclusion of exon 7 in SMN2 mRNA: potential therapy of SMA", Gene Ther., (20):1532-1538.
Gubitz et al., 2004 "The SMN complex", Exp Cell Res.; 296:51-6.
Paushkin et al.., 2002 "The SMN complex, an assemblyosome of ribonucleoproteins" Curr Opin Cell Biol., 14:305-12.
Sumner et al., 2006, "SMN mRNA and protein levels in peripheral blood: biomarkers for SMA clinical trials", Neurology, 66:1067-1073.
Yong et al., 2004, "Why do cells need an assembly machine for RNA-protein complexes?" Trends Cell Biol.; 15(5):226-32.
Hudziak et al., 2000, "Antiproliferative effects of steric blocking phosphordiamidate morpholino antisense agents directed against c-myc." Antisense & Nucleic Acid Drug Development 10(3):163-176.
McTiernan et al., 1999, "Characterization of proximal transcription regulatory elements in the rat phospholamban promoter." J. Molecular & Cellular Cardiology. 31(12): 2137-2153.
Wang et al., 2003, "Human SP-A 3'-UTR variants mediate differential gene expression in basal levels and in response to dexamethasone." Am. J. Physiology. Lung Cell. and Molec Physio. 283(5):L738-E748.
Zwicky et al., 2003, "Exploring the Role of 5' Alternative Splicing and of the 3'-Untranslated region of Cathepsin B MRNA" Biological Chemistry 384(7): 1007-1018.
European Search Report, dated Nov. 17, 2011 issued in EP 2 400 038.
U.S. Appl. No. 12/143,705, filed Jun. 20, 2008, Friesen et al.
U.S. Appl. No. 12/143,697, filed Jun. 20, 2008, Friesen et al.
U.S. Appl. No. 12/144,577, filed Jun. 3, 2008, Friesen et al.
European Search Report, dated May 18, 2011 issued in EP Application No. 10189802.1.

(56) References Cited

OTHER PUBLICATIONS

Amendment, dated Aug. 2, 2011 in U.S. Appl. No. 12/144,577.
Final Rejection, dated Nov. 28, 2011 in U.S. Appl. No. 12/144,577.
Amendment, dated Aug. 2, 2011 in U.S. Appl. No. 12/143,705.
Final Rejection, dated Nov. 28, 2011 in U.S. Appl. No. 12/143,705.
Amendment, dated Aug. 4, 2011 in U.S. Appl. No. 10/543,033.
Final Rejection, dated Oct. 13, 2011 in U.S. Appl. No. 10/895,393.
Han et al. Interactive effects of the tumor necrosis factor promoter and 3'-untranslated regions. J Immunol. Mar. 15, 1991;146(6):1843-8.
Hyder et al., 1996, Cancer Research, 56 3954-3960.
Levy et al., 1996 "Hypoxia-inducible Protein Binding to Vascular Endothelial Growth Factor mRNA and Its Modulation by the von Hippel-Lindau Protein." J. Biol. Chem., 271(41): 25492-25497.
Nunokawa et al.. Expression of human inducible nitric oxide synthase is regulated by both promoter and 3'-regions. Biochem Biophys Res Commun. Apr. 17, 1997;233(2):523-6.
Wickstrom E. Oligonucleotide treatment of ras-induced tumors in nude mice. Mol Biotechnol. May 2001;18(1):35-55.
Bakheet et al., "ARED: human AU-rich element-containing mRNA database reveals an unexpectedly diverse functional repertoire of encoded proteins." Nucleic Acids Res. Jan. 1, 2001;29(1):246-54.
Final Office Action dated Jun. 19, 2013, in U.S. Appl. No. 13/646,924.
International Preliminary Report on Patentability dated Oct. 15, 2010 PCTUS0401643.
Lowe et al., "A computer program for selection of oligonucleotide primers for polymerase chain reactions." Nucleic Acids Res. Apr. 11, 1990;18(7):1757-61.
Notice of Allowance dated Jan. 8. 2013, in U.S. Appl. No. 10/543,033.
Notice of Allowance dated Dec. 27, 2012, in U.S. Appl. No. 10/851,074.
Notice of Allowance dated Jan. 24, 2014, in U.S. Appl. No. 13/646,943.
Notice of Allowance dated Jun. 1, 2012, in U.S. Appl. No. 12/143,705.
Notice of Allowance dated Jun. 8, 2012, in U.S. Appl. No. 12/144,577.
Office Action dated Jun. 12, 2014, in U.S. Appl. No. 13/646,924.
Office Action dated Jan. 28, 2013, in U.S. Appl. No. 13/646,924.
Office Action dated May 2, 2013, in U.S. Appl. No. 13/646,943.
Office Action dated May 28, 2014, in U.S. Appl. No. 13/873,543.
Partial Search Report dated Jul. 24, 2012 in EP 12152322.
Project Catalyst Poster—"Identification and characterization of small molecules for the treatment of duchenne muscular dystrophy," previously presented at the Muscular Dystrophy Coordinating Committee on Jun. 25, 2007 in Washington, D.C.
Project Catalyst Poster Abstract—"Identification and characterization of small molecules for the treatment of duchenne muscular dystrophy," previously presented at the Muscular Dystrophy Coordinating Committee on Jun. 25, 2007 in Washington, D.C.
PTC Therapeutics Poster—"Identification and characterization of small molecules for the treatment of duchenne muscular dystrophy," previously presented at the 11th Annual Meeting of the RNA Society on Jun. 20, 2006 in Seattle, Washington.
Restriction Requirement dated Dec. 5, 2013, in U.S. Appl. No. 13/873,543.
Search Report & Opinion dated Nov. 9, 2012 in EP 12152322.
Supplemental Notice of Allowance dated Jan. 25, 2013, in U.S. Appl. No. 10/543,033.
de Wet et al., "Firefly Luciferase Gene: Structure and Expression in Mammalian Cells", *Molecular and Cellular Biology*, 7(2):725-737 (1987).
Forsythe et al., "Activation of Vascular Endothelial Growth Factor Gene Transcription by Hypoxia-Inducible Factor 1", *Molecular and Cellular Biology*, 16(9):4604-4613 (1996).
International Search Report dated Nov. 6, 2007 in PCT/US04/20751.
Tischer et al., "The Human Gene for Vascular Endothelial Growth Factor", *The Journal of Biological Chemistry*, 266(18):11947-11954 (1991).
Banholzer et al., "Rapamycin Destabilizes Interleukin-3 mRNA in Autocrine Tumor Cells by a Mechanism Requiring an Intact 3' Untranslated Region", *Molecular and Cellular Biology* 17(6):3254-3260 (1997).
Lemm et al., "Regulation of c-myc mRNA decay by Translational Pausing in a Coding Region Instability Determinant", *Molecular and Cellular Biology*, 22(12):3959-3969 (2002).
Bhattacharyya et al., "Mining the GEMS—a novel platform technology targeting post-transcriptional control mechanisms", *Drug Discovery Today*, 12(13-14):553-560 (2007).
Fortes et al., "Inhibiting expression of specific genes in mammalian cells with 5' end-mutated U1 small nuclear RNAs targeted to terminal exons of pre-mRNA", *PNAS* 100(14):8264-8269 (2003).
Nishimori et al., "Involvement of the 3'-untranslated region of cyclooxygenase-2 gene in its post-transcriptional regulation through the glucocorticoid receptor", *Life Sciences*, 74(20):2505-2513 (2004).
Supplemental Partial European Search Report issued in EP 04 78 1055 and dated May 30, 2008.
Wang et al., "Human SP-A 3'-UTR variants mediate differential gene expression in basal levels and in response to dexamethasone", *American Journal of Physiology, Lung Cellular and Molecular Physiology*, 284(5):L738-L748 (2003).

* cited by examiner

~0.5 kb

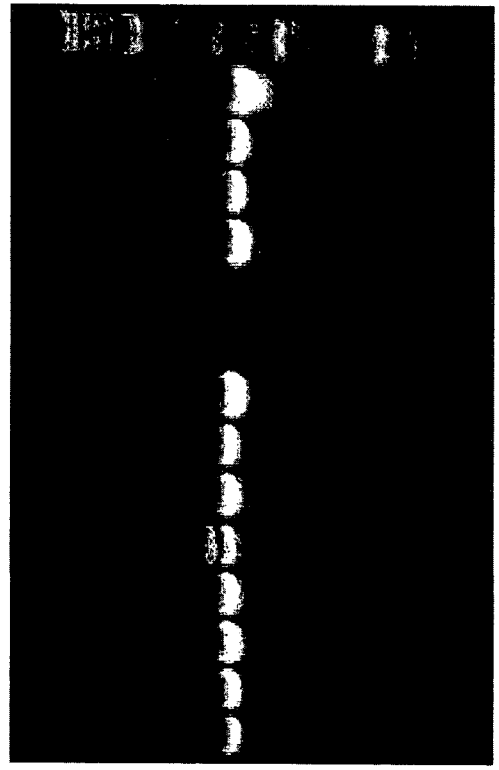

METHODS AND AGENTS FOR SCREENING FOR COMPOUNDS CAPABLE OF MODULATING GENE EXPRESSION

CROSS-REFERENCE TO RELATED APPLICATIONS

This application is a continuation-in-part of International Application PCT/US04/01643, filed Jan. 21, 2004, entitled Methods for Identifying Compounds that Modulate Untranslated Region-Dependent Gene Expression and Methods of Using Same, under 35 U.S.C. §120. International Application PCT/US04/01643, filed Jan. 21, 2004 claims the benefit of and incorporates by reference U.S. Provisional Application No. 60/441,637, filed on Jan. 21, 2003. The entirety of these applications, including the sequence listing, is hereby incorporated by reference.

INCORPORATION OF THE SEQUENCE LISTING

A paper copy of the Sequence Listing and a computer readable form of the sequence listing on diskette, containing the file named "19025.012.SeqList.txt", which is 12,086 bytes in size (measured in MS-DOS), and which was recorded on Jul. 21, 2004, are herein incorporated by reference.

BACKGROUND OF THE INVENTION

Gene expression, defined as the conversion of the nucleotide sequence of a gene into the nucleotide sequence of a stable RNA or into the amino acid sequence of a protein, is very tightly regulated in every living organism. Regulation of gene expression both of mRNA stability and translation is important in cellular responses to development or environmental stimuli such as nutrient levels, cytokines, hormones, and temperature shifts, as well as environmental stresses like hypoxia, hypocalcemia, viral infection, and tissue injury (reviewed in Guhaniyogi & Brewer, 2001, Gene 265(1-2):11-23). Furthermore, alterations in mRNA stability have been causally connected to specific disorders, such as neoplasia, thalassemia, and Alzheimer's disease (reviewed in Guhaniyogi & Brewer, 2001, Gene 265(1-2):11-23 and Translational Control of Gene Expression, Sonenberg, Hershey, and Mathews, eds., 2000, CSHL Press).

Giordano et al., U.S. Pat. No. 6,558,007 (hereafter referred to as "the '007 patent"), assert that they provide a screening assay using a 5' mRNA UTR biased cDNA library or a 3' mRNA UTR biased cDNA library. The '007 patent further asserts that they provide a method of identifying a regulatory UTR sequence using their 5' or 3' mRNA UTR biased cDNA libraries. The '007 patent does not provide assays that mimic the in vivo state of a gene controlled by the presence of more than one UTR, for example, genes which are flanked by a 5' UTR and a 3' UTR. Moreover, the approach of the '007 patent requires the libraries described therein.

Pesole et al. assert that the 5'- and 3'-UTRs of eukaryotic mRNAs are known to play a crucial role in post-transcriptional regulation of gene expression. Pesole et al., (2002) *Nucleic Acids Research*, 3(1):335-340, which is hereby incorporated by reference in its entirety. They develop and describe several databases with nucleic acid sequences from UTRs. Many of their database entries are enriched with specialized information including the presence of sequence patterns demonstrated by experimental evidence to play a functional role in gene regulation. Pesole et al. do not provide assays to obtain such experimental evidence, nor do they suggest that such experiments mimicked the in vivo state of the UTR database entry. Moreover, the methodology of Pesole et al. is based on sequence analysis and prior experimental evidence. Pesole et al. do not provide experimental screening methods for developing agents to modulate the 5'- and 3'-UTRs of eukaryotic mRNAs that are known to play a crucial role in post-transcriptional regulation of gene expression nor do they suggest a methodology to find novel 5'- and 3'-UTRs of eukaryotic mRNAs that play a crucial role in post-transcriptional regulation of gene expression. In addition, the approach of Pesole et al. requires the databases described therein.

Trotta et al. assert that a the interaction of the La antigen with mdm2 5' UTR enhances mdm2 mRNA translation. Trotta et al., (2003) *Cancer Cell* 3:145-160, which is hereby incorporated by reference in its entirety. They do not suggest methods or agents to screen or identify more UTRs with a similar role in translational regulation of gene expression. Moreover, no agents are provided to screen for compounds that would modulate the regulation of mdm2 mRNA translation.

SUMMARY OF THE INVENTION

The present invention includes a nucleic acid construct comprising a high-level mammalian expression vector, an intron, and a nucleic acid sequence encoding a reporter polypeptide, wherein said nucleic acid sequence encoding a reporter polypeptide is proximally linked to a target untranslated region (UTR).

The present invention also includes a nucleic acid construct comprising a high-level mammalian expression vector and a nucleic acid sequence encoding a reporter polypeptide, wherein said nucleic acid sequence encoding a reporter polypeptide is directly linked to one or more target UTRs.

The present invention also includes a nucleic acid molecule comprising a nucleic acid sequence encoding a reporter polypeptide directly linked to one or more target UTRs.

The present invention also includes a heterologous population of nucleic acid molecules, wherein said heterologous population comprises a reporter nucleic acid sequence, wherein said nucleic acid sequence encoding a reporter polypeptide is directly linked to one or more target UTRs.

The present invention also includes a method of making a nucleic acid construct to screen for a compound comprising: a) cloning a gene and a vector in said nucleic acid construct; b) engineering said nucleic acid construct to prevent an expressed gene product from having a UTR not found in a target gene; and c) directly linking a target UTR to said gene.

The present invention also includes a method of screening for a compound that modulates expression of a polypeptide comprising: a) maintaining a cell, wherein said cell has a nucleic acid molecule and said nucleic acid molecule comprises a gene encoding a reporter polypeptide and said reporter gene is flanked by a target 5' UTR and a target 3' UTR; b) forming a UTR-complex in said cell; c) contacting a compound with said UTR-complex; and d) detecting an effect of said compound on said UTR-complex.

The present invention also includes a method of screening in vivo for a compound that modulates UTR-dependent expression comprising: a) providing a cell having a nucleic acid construct comprising a high-expression, constitutive promoter upstream from a target 5' UTR, said target 5' UTR upstream from a nucleic acid sequence encoding a reporter polypeptide, and said nucleic acid sequence encoding a reporter polypeptide upstream from a target 3' UTR; b) contacting said cell with a compound; c) producing a nucleic acid molecule that contains a nucleic acid sequence encoding a reporter polypeptide and does not contain UTR not found in a target gene; and d) detecting said reporter polypeptide.

The present invention also includes a method of screening in vitro for a compound that modulates UTR-affected expression comprising: a) providing an in vitro translation system; b) contacting said in vitro translation system with a compound and a nucleic acid molecule comprising a target 5' UTR, said target 5' UTR upstream from a nucleic acid sequence encoding a reporter polypeptide and said nucleic acid sequence encoding a reporter polypeptide upstream from a target 3' UTR, wherein said nucleic acid molecule is in an absence of a UTR not found in a target gene; and c) detecting said reporter polypeptide in vitro.

The present invention also includes a method of expressing a nucleic acid molecule in a cell comprising: a) providing a heterologous nucleic acid molecule to a cell, wherein said nucleic acid molecule comprises a nucleic acid sequence encoding a reporter polypeptide flanked by target UTRs in an absence of a UTR not found in a target gene; and b) detecting said reporter polypeptide in vivo.

The present invention also includes a method of screening for a compound that modulates protein expression through a main ORF-independent, UTR-affected mechanism comprising: a) growing a stable cell line having a reporter gene proximally linked to a target UTR; b) comparing said stable cell line in the presence of a compound relative to in an absence of said compound; and c) selecting for said compound that modulates protein expression through a main ORF-independent, UTR-affected mechanism.

The present invention also includes a method of screening for a compound that modulates protein expression through a main ORF-independent, UTR-affected mechanism comprising: a) substituting in a cell a target gene with a reporter gene, wherein proximally linked target UTRs of said target gene remain intact and said cell is a differentiated cell; b) growing said cell line; and c) selecting for said compound that modulates protein expression of said reporter gene through a main ORF-independent, UTR-affected mechanism.

The present invention also includes a method of screening for a compound that modulates protein expression through a UTR-affected mechanism comprising: a) growing a stable cell line having a reporter gene proximally linked to a target UTR, wherein said stable cell line mimics post-transcriptional regulation of a target gene found in vivo; b) growing said stable cell line; and c) selecting for said compound that modulates protein expression of said reporter gene through a UTR-affected mechanism.

The present invention also includes a method of screening for a compound that modulates protein expression through a UTR-affected mechanism comprising: a) growing a stable cell line having a reporter gene proximally linked to more than one target UTR; b) comparing said stable cell line in the presence of a compound relative to in an absence of said compound, wherein said compound does not modulate UTR-dependent expression if only one target UTR is proximally linked to a reporter gene; and c) selecting for said compound that modulates protein expression of said reporter gene through a UTR-affected mechanism.

BRIEF DESCRIPTION OF THE DRAWINGS

FIG. 2C sets forth the results of RT-PCR described in Example 2 to determine the quality of stable clones using using the primers indicated in FIG. 2A.

DESCRIPTION OF THE NUCLEIC ACID SEQUENCES

Figure 1:
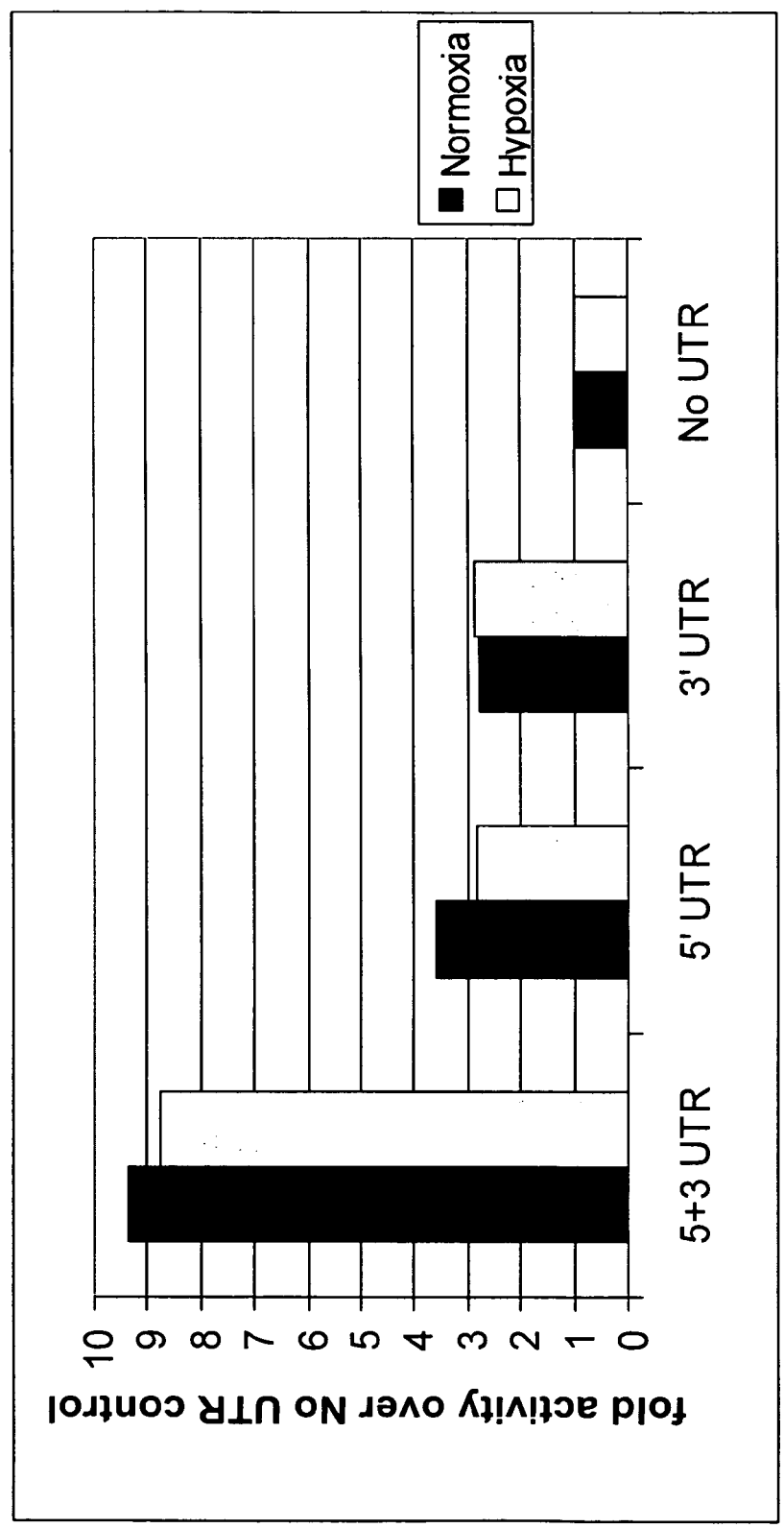
FIG. 1 sets forth the UTR specificity for reporter gene expression when flanked by the HIF 1α 5' and 3' UTR (5+3 UTR). The reporter gene is operably linked to the HIF 1α 5' and 3' UTR (5+3 UTR), the HIF 1α 5' UTR (5' UTR), the HIF 1α 3' UTR (3' UTR), or no HIF 1α UTR (No UTR) under conditions of normoxia and hypoxia.
Figure 2A:
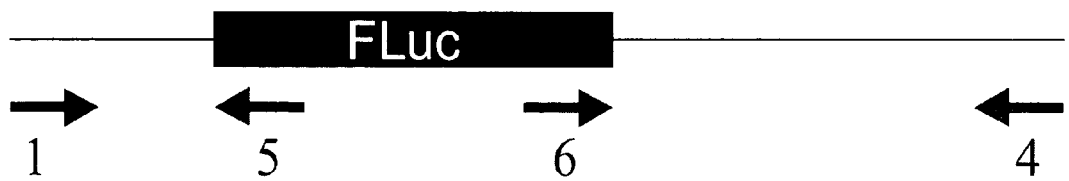
FIG. 2A sets forth a schematic of the construct indicating the locations of primers used.
Figure 2B:
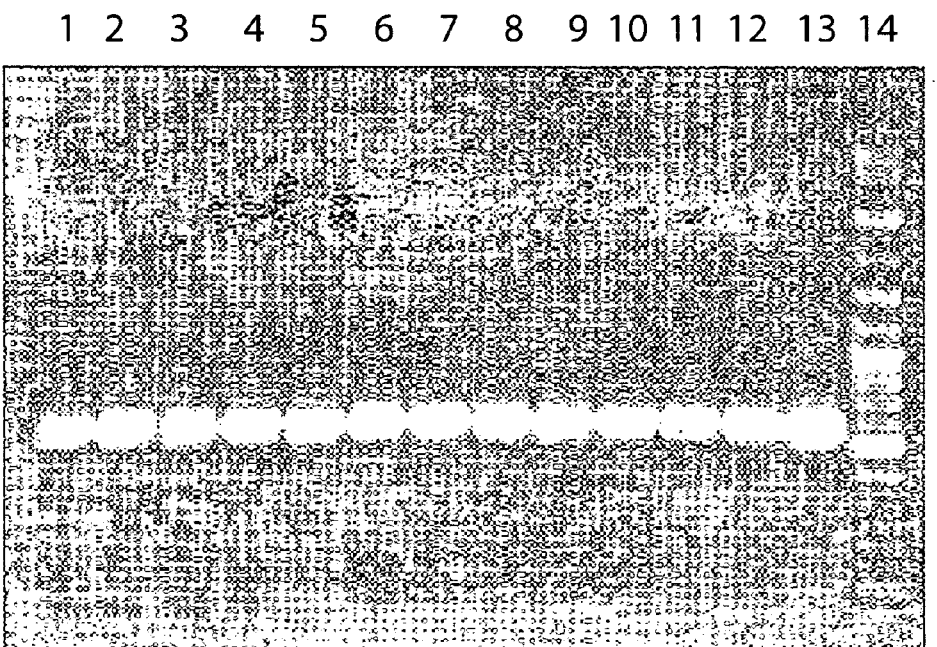
FIG. 2B sets forth the results of RT-PCR described in Example 2 to determine the quality of stable clones using using the primers indicated in FIG. 2A.
Figure 3:
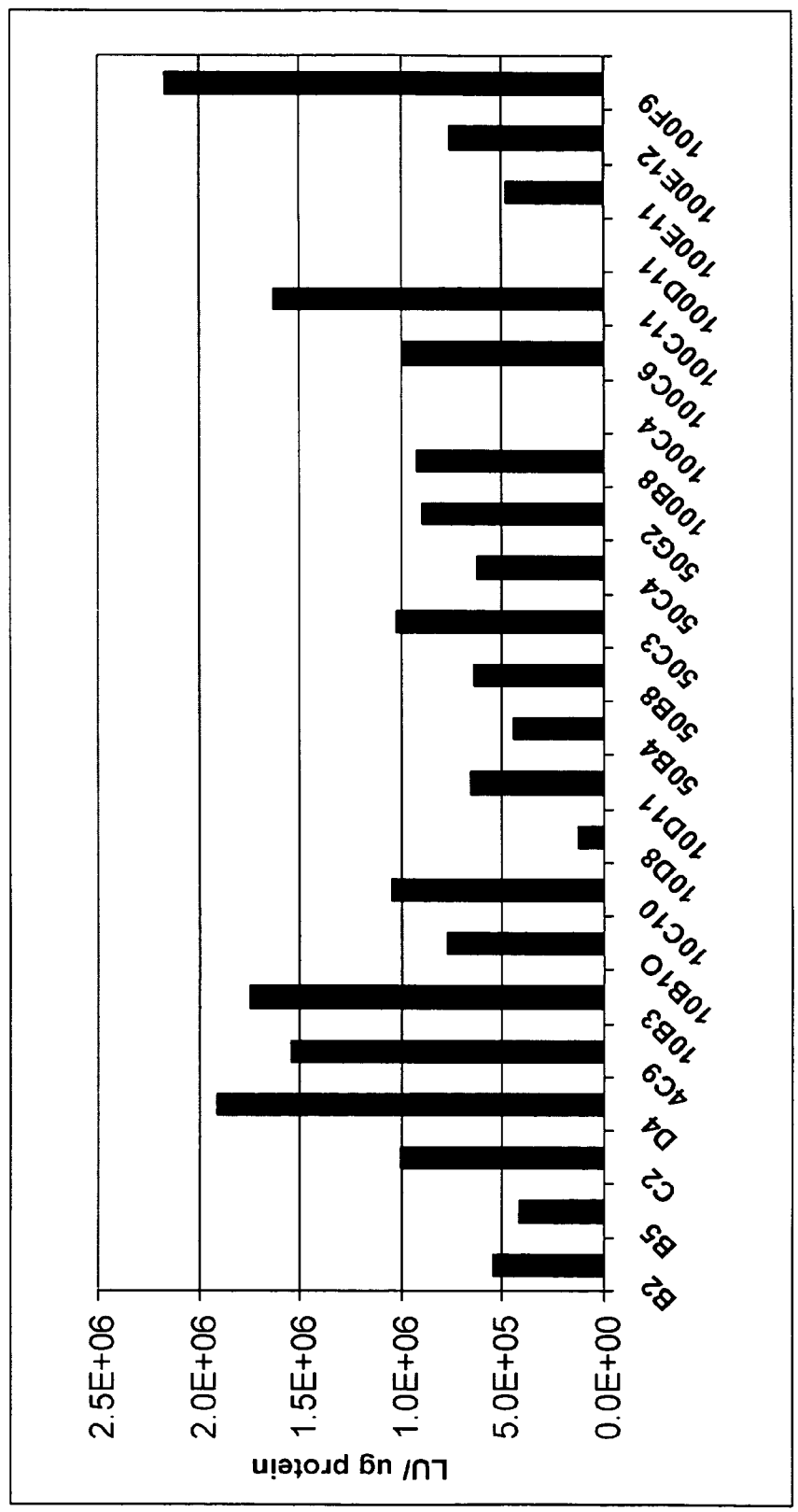
FIG. 3 sets forth the luciferase activity per microgram of total protein for each stable clonal cell line indicated.
Figure 4:
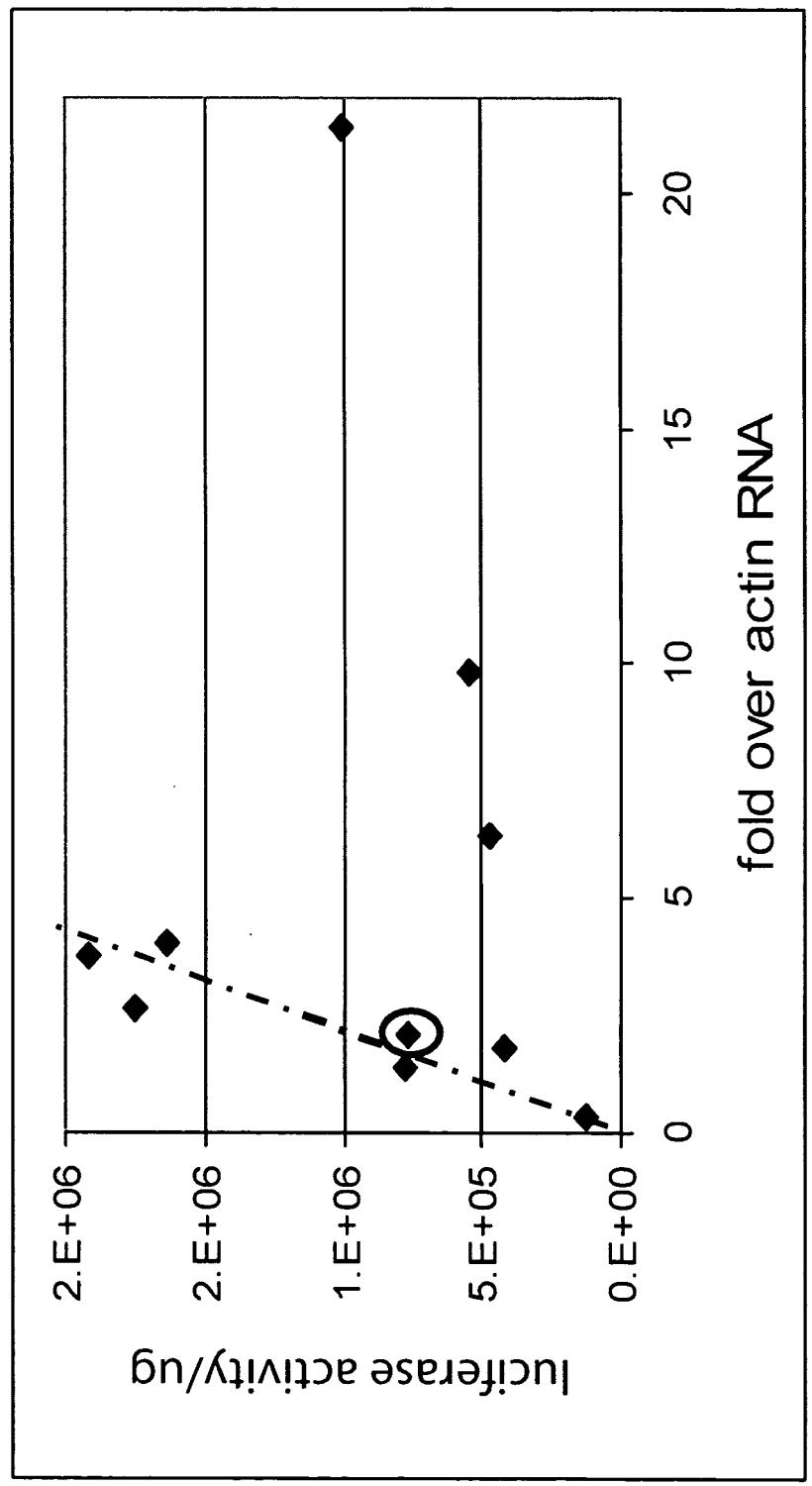
FIG. 4 sets forth sets forth the luciferase activity per microgram of total protein as a function of the fold increase over the level of actin RNA.

SEQ ID NO: 1 sets forth a luciferase 5' reverse primer.
SEQ ID NO: 2 sets forth a luciferase 3' forward primer.
SEQ ID NO: 3 sets forth a FLuc F.
SEQ ID NO: 4 sets forth a FLuc R.
SEQ ID NO: 5 sets forth a FLuc probe.
SEQ ID NO: 6 sets forth a homo sapiens VEGF 5' UTR, derived from Accession No. NM_03376 of AF095785.
SEQ ID NO: 7 sets forth a 3' UTR is derived from Accession No. AF022375, genomic contig where sequences are derived is VEGF-NT_007592.
SEQ ID NO: 8 sets forth a homo sapiens TNF-alpha 5' UTR derived from Accession No. NM_00594.
SEQ ID NO: 9 sets forth a homo sapiens TNF-alpha 3' UTR derived from Accession No. NM_00594.
SEQ ID NO: 10 sets forth an ARE 1 from homo sapiens TNF-alpha 3' UTR derived from Accession No. NM_00594.
SEQ ID NO: 11 sets forth an ARE 1 from homo sapiens TNF-alpha 3' UTR derived from Accession No. NM_00594.
SEQ ID NO: 12 sets forth an ARE 1 from homo sapiens TNF-alpha 3' UTR derived from Accession No. NM_00594.
SEQ ID NO: 13 sets forth a constitutive decay element (hereinafter "CDE") derived from homo sapiens TNF-alpha 3' UTR as discussed in Stoecklin et al., (2003) *Molecular and Cellular Biology*, 23(10):3506-3515, which is hereby incorporated by reference in its entirety.
SEQ ID NO: 14 sets forth a putative second ARE from homo sapiens TNF-alpha 3' UTR derived from Accession No. NM_00594.
SEQ ID NO: 15 sets forth a putative poly(A) signal from homo sapiens TNF-alpha 3' UTR derived from Accession No. NM_00594.
SEQ ID NO: 16 sets forth a homo sapiens MDM2 5' UTR as derived from Accession No. NM_002392.
SEQ ID NO: 17 sets forth a homo sapiens Her-2 5' UTR sequence derived from Accession No. NM_004448.
SEQ ID NO: 18 sets forth a homo sapiens Her-2 5' uORF sequence derived from Accession No. NM_004448.
SEQ ID NO: 19 sets forth a Her-2 3' UTR derived from Accession No. NM_004448.
SEQ ID NO: 20 sets forth a 336 nucleotide region of a VEGF 5' UTR
SEQ ID NO: 21 sets forth a 476 nucleotide region of a VEGF 5' UTR.
SEQ ID NO: 22 sets forth a 73 nucleotide sequence from a Her-2 3' UTR.
SEQ ID NO: 23 sets forth a 81 nucleotide region native to pcDNA™3.1/Hygro (Invitrogen Corp., Carlsbad, Calif.).

SEQ ID NO: 24 sets forth a 134 nucleotide region native to pcDNA™3.1/Hygro (Invitrogen Corp., Carlsbad, Calif.).

DEFINITIONS

As used herein, the term "construct" refers to an artificially manipulated nucleic acid molecule.

As used herein, the term "gene" is a segment of DNA that is capable of producing a polypeptide.

As used herein, the term "heterologous" refers to ingredients or constituents of dissimilar or diverse origin.

As used herein, the term "mammalian cancer cell" or "mammalian tumor cell" refers to a cell derived from a mammal that proliferates inappropriately.

As used herein, the term "main ORF-independent mechanism" refers to a cellular pathway or process, wherein at least one step relates to gene expression and is not dependent on the nucleic acid sequence of the main open reading frame.

As used herein, the term "reporter gene" refers to any gene whose expression can be measured.

As used herein, the term "RNA induced gene silencing, or RNA interference (RNAi)" refers to the mechanism of double-stranded RNA (dsRNA) introduced into a system to reduce protein expression of specific genetic sequence.

As used herein, the term "specifically bind" means that a compound binds to another compound in a manner different from a similar type of compounds, e.g. in terms of affinity, avidity, and the like. In a non-limiting example, more binding occurs in the presence of a competing reagent, such as casein. In another non-limiting example, antibodies that specifically bind a target protein should provide a detection signal at least 2-, 5-, 10-, or 20-fold higher relative to a detection signal provided with other molecules when used in Western blots or other immunochemical assays. In an alternative non-limiting example, a nucleic acid can specifically bind its complementary nucleic acid molecule. In another non-limiting example, a transcription factor can specifically bind a particular nucleic acid sequence.

As used herein, the term "secondary structure" means the alpha-helical, beta-sheet, random coil, beta turn structures and helical nucleic acid structures that occur in proteins, polypeptides, nucleic acids, compounds comprising modified nucleic acids, compounds comprising modified amino acids and other types of compounds as a result of, at least, the compound's composition.

As used herein, the term "non-peptide therapeutic agent" and analogous terms include, but are not limited to organic or inorganic compounds (i.e., including heteroorganic and organometallic compounds but excluding proteins, polypeptides and nucleic acids).

As used herein, the term "uORF" refers to an upstream open reading frame that is in the 5' UTR of the main open reading frame, i.e., that encodes a functional protein, of a mRNA.

As used herein, the term "UTR" refers to the untranslated region of a mRNA.

As used herein, the term "untranslated region-dependent expression" or "UTR-dependent expression" refers to the regulation of gene expression through UTRs at the level of mRNA expression, i.e., after transcription of the gene has begun until the protein or the RNA product(s) encoded by the gene has been degraded or excreted.

As used herein, the term "vector" refers to a nucleic acid molecule used to introduce a nucleic acid sequence in a cell or organism.

DETAILED DESCRIPTION OF THE INVENTION

The present invention includes and utilizes the fact that an untranslated region (UTR) is capable of modulating expression of a gene and that such modulation of expression is capable of being altered or modulated by the addition of compounds. In a preferred embodiment, a UTR is a region of a RNA that is not translated into protein. In a more preferred embodiment, a UTR is a flanking region of the RNA transcript that is not translated into the targeted protein, and can include a 5' UTR that has a short, putative open reading frame. In a most preferred embodiment, the UTR is a 5' UTR, i.e., upstream of the coding region, or a 3' UTR, i.e., downstream of the coding region.

Moreover, the present invention includes and provides agents and methods useful in screening for a compound capable of modulating gene expression and also hybrid molecules.

Nucleic Acid Agents and Constructs

One skilled in the art may refer to general reference texts for detailed descriptions of known techniques discussed herein or equivalent techniques. These texts include Ausubel et al., *Current Protocols in Molecular Biology*, John Wiley and Sons, Inc. (1995); Sambrook et al., *Molecular Cloning, A Laboratory Manual* (2d ed.), Cold Spring Harbor Press, Cold Spring Harbor, N.Y. (1989); Birren et al., *Genome Analysis: A Laboratory Manual*, volumes 1 through 4, Cold Spring Harbor Press, Cold Spring Harbor, N.Y. (1997-1999). These texts can, of course, also be referred to in making or using an aspect of the invention.

UTRs

The present invention includes nucleic acid molecules with UTRs that comprise or consist of a gene expression modulator (GEM), fragments thereof, and complements of each. As used herein, a UTR can be a naturally occurring genomic DNA sequence. In a preferred embodiment, a UTR is a 5' UTR, i.e., upstream of the coding region, or a 3' UTR, i.e., downstream of the coding region.

In one embodiment, a UTR of the present invention comprises or consists of a nucleic acid sequence selected from a group consisting of SEQ ID NOs: 6-22, and including fragments of each, and complements of all. In another embodiment, a nucleic acid molecule of the present invention contains or comprises a nucleic acid sequence that is greater than 85% identical, and more preferably greater than 86, 87, 88, 89, 90, 91, 92, 93, 94, 95, 96, 97, 98, or 99% identical to a UTR of the present invention, a GEM nucleic acid sequence, a complement of either, and a fragment of any of these sequences.

The hybridization conditions typically involve nucleic acid hybridization in about 0.1× to about 10×SSC (diluted from a 20×SSC stock solution containing 3 M sodium chloride and 0.3M sodium citrate, pH 7.0 in distilled water), about 2.5× to about 5×Denhardt's solution (diluted from a 50× stock solution containing 1% (w/v) bovine serum albumin, 1% (w/v) Ficoll® (Amersham Biosciences Inc., Piscataway, N.J.), and 1% (w/v) polyvinylpyrrolidone in distilled water), about 10 mg/ml to about 100 mg/ml salmon sperm DNA, and about 0.02% (w/v) to about 0.1% (w/v) SDS, with an incubation at about 20° C. to about 70° C. for several hours to overnight.

In a preferred aspect, the moderate stringency hybridization conditions are provided by 6×SSC, 5×Denhardt's solution, 100 mg/ml salmon sperm DNA, and 0.1% (w/v) SDS, with an incubation at 55° C. for several hours. The moderate stringency wash conditions are about 0.02% (w/v) SDS, with an incubation at about 55° C. overnight. In a more preferred aspect, the high stringency hybridization conditions are about 2×SSC, about 3×Denhardt's solution, and about 10 mg/ml salmon sperm DNA. The high stringency wash conditions are about 0.05% (w/v) SDS, with an incubation at about 65° C. overnight.

The percent identity is preferably determined using the "Best Fit" or "Gap" program of the Sequence Analysis Software Package™ (Version 10; Genetics Computer Group, Inc., University of Wisconsin Biotechnology Center, Madison, Wis.). "Gap" utilizes the algorithm of Needleman and Wunsch to find the alignment of two sequences that maximizes the number of matches and minimizes the number of gaps. "BestFit" performs an optimal alignment of the best segment of similarity between two sequences and inserts gaps to maximize the number of matches using the local homology algorithm of Smith and Waterman. The percent identity calculations may also be performed using the Megalign program of the LASERGENE bioinformatics computing suite (default parameters, DNASTAR Inc., Madison, Wis.). The percent identity is most preferably determined using the "Best Fit" program using default parameters.

Any of a variety of methods may be used to obtain one or more of the above-described nucleic acid molecules of the present invention. Automated nucleic acid synthesizers may be employed for this purpose. In lieu of such synthesis, the disclosed nucleic acid molecules may be used to define a pair of primers that can be used with the polymerase chain reaction (PCR) to amplify and obtain any desired nucleic acid molecule or fragment.

Short nucleic acid sequences having the ability to specifically hybridize to complementary nucleic acid sequences may be produced and utilized in the present invention, e.g., as probes to identify the presence of a complementary nucleic acid sequence in a given sample. Alternatively, the short nucleic acid sequences may be used as oligonucleotide primers to amplify or mutate a complementary nucleic acid sequence using PCR technology. These primers may also facilitate the amplification of related complementary nucleic acid sequences (e.g., related sequences from other species).

Use of these probes or primers may greatly facilitate the identification of transgenic cells or organisms that contain the presently disclosed structural nucleic acid sequences. Such probes or primers may also, for example, be used to screen cDNA, mRNA, or genomic DNA libraries for additional nucleic acid sequences related to or sharing homology with the presently disclosed promoters and structural nucleic acid sequences. The probes may also be PCR probes, which are nucleic acid molecules capable of initiating a polymerase activity while in a double-stranded structure with another nucleic acid.

A primer or probe is generally complementary to a portion of a nucleic acid sequence that is to be identified, amplified, or mutated and of sufficient length to form a stable and sequence-specific duplex molecule with its complement. The primer or probe preferably is about 10 to about 200 residues long, more preferably is about 10 to about 100 residues long, even more preferably is about 10 to about 50 residues long, and most preferably is about 14 to about 30 residues long.

The primer or probe may, for example without limitation, be prepared by direct chemical synthesis, by PCR (U.S. Pat. Nos. 4,683,195 and 4,683,202), or by excising the nucleic acid specific fragment from a larger nucleic acid molecule. Various methods for determining the sequence of PCR probes and PCR techniques exist in the art. Computer-generated searches using programs such as Primer3 (www-genome.wi.mit.edu/cgi-bin/primer/primer3.cgi), STSPipeline (www-genome.wi.mit.edu/cgi-bin/www-STS_Pipeline), or GeneUp (Pesole et al., *BioTechniques* 25:112-123, 1998), for example, can be used to identify potential PCR primers.

Furthermore, sequence comparisons can be done to find nucleic acid molecules of the present invention based on secondary structure homology. Several methods and programs are available to predict and compare secondary structures of nucleic acid molecules, for example, GeneBee (available on the world wide web at genebee.msu.su/services/rna2_reduced.html); the Vienna RNA Package (available on the world wide web at tbi.univie.ac.at/~ivo/RNAI); Sstruct-View (available on the world wide web at the Stanford Medical Informatics website, under: projects/helix/sstructview/home.html and described in "RNA Secondary Structure as a Reusable Interface to Biological Information Resources." 1997. *Gene* vol. 190GC59-70). For example, comparisons of secondary structure are preformed in Le et al., A common RNA structural motif involved in the internal initiation of translation of cellular mRNAs. 1997. *Nuc. Acid. Res.* vol. 25(2):362-369.

UTR-Complexes

The present invention also includes a UTR that is complexed. A UTR-complex includes a complex of two or more identical UTRs, one or more different UTRs, a pair of UTRs from the same gene, one or more UTRs and one or more proteins, one or more UTRs and one or more nucleic acids, one or more UTRs and one or more nucleic acid molecules. By way of non-limiting examples, a UTR-complex can be a complex of a UTR and a small interfering RNAs (siRNA), a UTR and a RNA/DNA sense strand, or a UTR and a RNA/DNA antisense strand.

A UTR-complex of the present invention can refer to a non-covalent or covalent attachment to a UTR. In a preferred embodiment, a GEM or UTR of a nucleic acid molecule modulates attachment of complex constituents to the nucleic acid molecule that has a UTR. In a more preferred embodiment, a UTR-complex varies depending on the nucleic acid sequence of the UTR within the nucleic acid molecule. In a most preferred embodiment, the nucleic acid sequence of the UTR that affects a UTR-complex indicates the presence of a GEM. In a preferred embodiment, the UTR, a GEM, or a fragment of either, modulates the formation of a UTR-complex. In an alternate embodiment, the UTR, or a fragment thereof, modulates the disassociation, the stability, or the constituents of the UTR-complex. In a preferred embodiment, the non-covalent or covalent attachment is a transient attachment. In a more preferred embodiment, the constituents of a UTR-complex vary during processing. In a most preferred embodiment, the constituents of the UTR-complex vary depending on the nucleic acid sequence of the UTR within the nucleic acid molecule, which is in the presence of cellular proteins that can be cell-type specific.

A UTR-complex of the present invention can include the non-covalent or covalent attachment of one or more ribonucleoproteins to a nucleic acid molecule that contains a UTR. In a preferred embodiment, a GEM of the present invention or a UTR of a nucleic acid molecule of the present invention modulates the attachment of the nucleic acid molecule and one or more ribonucleoproteins.

By way of non-limiting examples, UTR-complexes are provided in Pesole et al. and Trotta et al., cited and incorporated by reference above, as well as on the world wide web, including at the ftp site: bighost.ba.itb.cnr.it/pub/Embnet/Database/UTR/ (as available on Jul. 20, 2004), which is hereby incorporated by reference in its entirety. Furthermore, a GEM or UTR of the present invention can interact with a protein from the large family of AU-rich containing mRNAs associated with Hu-Antigen R (HuR)-mediated regulation (including IL-3, c-fos, c-myc, GM-CSF, AT-R1, Cox-2, IL-8 or TNF-α as cited in WO 03/087815), the RNA recognition motif (RRM) superfamily, the small nuclear RNPs (snRNP), hnRNP proteins, mRNA proteins, exon junction complex (EJC) proteins, cytoplasmic exon junction complex (cEJC)

proteins, U snRNA proteins, nuclear pore complex proteins, dead-box family proteins, splicing factors, ribosomal proteins, and translation-specific proteins that are non-ribosomal, non-regulatory ribosomal protein, and chromatin-associated protein. For specific examples see Dreyfuss, et al. (2002) *Nature Reviews. Molecular Cell Biology* 3:195-205, hereby incorporated in its entirety. See also on the world wide web at the ftp site: ftp.ebi.ac.uk/pub/databases/UTR/ (as available on Jul. 21, 2004), which is hereby incorporated by reference in its entirety. In the present invention, splicing factors include, but are not limited to, serine-argenine (SR) proteins. In the present invention, translation-specific proteins that are non-ribosomal include, without limitation, exon-junction complex proteins, poly-A binding proteins, and cap-binding proteins.

Other examples of UTR-complexes include a TNF-α mRNA complexed with the tristetraprolin protein (TTP; see Lai et al., (1999) *Molecular and Cellular Biology*, 19(6): 4311-4323, hereby incorporated by reference in its entirety) and TIA-1 bound to AREs in the 3' UTRs. The TIA-1 recognition results in more TIAs binding to the first TIA-1. This TIA complex recognizes the 40 S ribosome subunit which is bound to the 5' UTR. Therefore, preventing the TIA-1 from binding to the AREs prevents translation of the encoded protein upstream of the bound ARE in the 3' UTR. See Kedersha and Anderson, (2002) *Biochemical Society Transactions*, 30(6):963-969, hereby incorporated by reference in its entirety.

Constructs of the Present Invention

The present invention includes and provides nucleic acid constructs. It is understood that any of the constructs and other nucleic acid agents of the present invention can be either DNA or RNA. In a preferred embodiment, a construct can be a nucleic acid molecule having a UTR, a coding sequence, or both. In another embodiment, a construct is composed of at least one UTR of the present invention, a sequence encoding a reporter polypeptide, and a vector. Moreover, any of the nucleic acid molecules of the present invention can be used in combination with a method of the present invention.

Vectors

Exogenous genetic material may be introduced into a host cell by use of a vector or construct designed for such purpose. Any of the nucleic acid sequences of the present invention can be incorporated into a vector or construct of the present invention. A vector or construct of the present invention includes, without limitation, linear or closed circular plasmids. A vector system may be a single vector or plasmid or two or more vectors or plasmids that together contain the total DNA to be introduced into the genome of the host. In a preferred embodiment, a vector contains a promoter functional in mammalian cells or bacteria or both. Methods for preparing vectors or constructs are well known in the art.

Vectors suitable for replication in mammalian cells may include viral replicons, or sequences that insure integration of the appropriate sequences encoding HCV epitopes into the host genome. For example, another vector used to express foreign DNA is vaccinia virus. Such heterologous DNA is generally inserted into a gene that is non-essential to the virus, for example, the thymidine kinase gene (tk), which also provides a selectable marker. Expression of the HCV polypeptide then occurs in cells or animals that are infected with the live recombinant vaccinia virus.

In general, plasmid vectors containing replicon and control sequences that are derived from species compatible with the host cell are used in connection with bacterial hosts. The vector ordinarily carries a replication site, as well as marking sequences that are capable of providing phenotypic selection in transformed cells. For example, *E. coli* is typically transformed using a construct with a backbone derived from a vector, such as pBR322, which contains genes for ampicillin and tetracycline resistance and thus provides easy approach for identifying transformed cells. The pBR322 plasmid, or other microbial plasmid or phage, also generally contains, or is modified to contain, promoters that can be used by the microbial organism for expression of the selectable marker genes.

In a preferred embodiment of the present invention, an expression vector can be a high-level mammalian expression vector designed to randomly integrate into the genome, for example, pCMR1. A high-level expression vector will have about 100 to about 1000 copies per cell, about 100 to about 500 copies per cell, about 500 to about 1000 copies per cell, or about 250 to about 1000 copies per cell. In one embodiment, a high-level mammalian expression vector is derived from the family of pUC vectors. In a preferred embodiment of the present invention, an expression vector can be a high-level mammalian expression vector designed to site-specifically integrate into the genome of cells. For example, pMCP1 can site-specifically integrate into the genome of cells genetically engineered to contain the FRT site-specific recombination site via the Flp recombinase (see, e.g., Craig, 1988, Ann. Rev. Genet. 22: 77-105; and Sauer, 1994, Curr. Opin. Biotechnol. 5: 521-527).

Promoters

A construct can include a promoter, e.g., a recombinant vector typically comprises, in a 5' to 3' orientation: a promoter to direct the transcription of a nucleic acid molecule of interest.

In a preferred aspect of the present invention, a construct can include a mammalian promoter and can be used to express a nucleic acid molecule of choice. As used herein, a "mammalian promoter" refers to a promoter functional in a mammalian cell, derived from a mammalian cell, or both. A number of promoters that are active in mammalian cells have been described in the literature. A promoter can be selected on the basis of the cell type into which the vector will be inserted.

A preferred promoter of the present invention is an endogenous promoter. A particularly preferred promoter is upstream from the target gene that has its expression modulated by a GEM. Other promoter sequences can be utilized in a construct or other nucleic acid molecules, suitable promoters include, but are not limited to, those described herein.

Suitable promoters for mammalian cells are known in the art and include viral promoters, such as those from Simian Virus 40 (SV40), Rous sarcoma virus (RSV), adenovirus (ADV), cytomegalovirus (CMV), and bovine papilloma virus (BPV) as well as the parvovirus B19p6 promoter and mammalian cell-derived promoters. A number of viral-based expression systems can be used to express a reporter gene in mammalian host cells. For example, if an adenovirus is used as an expression vector, sequences encoding a reporter gene can be ligated into an adenovirus transcription/translation complex comprising the late promoter and tripartite leader sequence.

Other examples of preferred promoters include tissue-specific promoters and inducible promoters. Other preferred promoters include the hematopoietic stem cell-specific, e.g., CD34, glucose-6-phosphotase, interleukin-1 alpha, CD11c integrin gene, GM-CSF, interleukin-5R alpha, interleukin-2, c-fos, h-ras and DMD gene promoters. Other promoters include the herpes thymidine kinase promoter, and the regulatory sequences of the metallothionein gene.

Inducible promoters suitable for use with bacteria hosts include the β-lactamase and lactose promoter systems, the arabinose promoter system, alkaline phosphatase, a tryptophan (trp) promoter system and hybrid promoters such as the tac promoter. However, other known bacterial inducible promoters are suitable. Promoters for use in bacterial systems also generally contain a Shine-Dalgarno sequence operably linked to the DNA encoding the polypeptide of interest.

A promoter can also be selected on the basis of their regulatory features, e.g., enhancement of transcriptional activity, inducibility, tissue specificity, and developmental stage-specificity. A promoter can work in vitro, for example the T7-promoter. Particularly preferred promoters can also be used to express a nucleic acid molecule of the present invention in a nonhuman mammal. Additional promoters that may be utilized are described, for example, in Bernoist and Chambon, *Nature* 290:304-310 (1981); Yamamoto et al., *Cell* 22:787-797 (1980); Wagner et al., *PNAS* 78:1441-1445 (1981); Brinster et al., *Nature* 296:39-42 (1982).

Main ORF

Agents and constructs of the invention can include nucleic acid molecules with a main ORF. As used herein, a "main ORF" is a nucleic acid sequence, including sequence in deoxyribonucleic acid or ribonucleic acid molecules, that codes for a polypeptide. As used herein, the term "main ORF DNA" refers to the open reading frame of a gene, i.e., the region of the gene that is translated into protein. As used herein, the term "ORF" refers to the open reading frame of a mRNA, i.e., the region of the mRNA that is translated into protein. In a preferred embodiment of the present invention, a main ORF can be in a gene with an upstream open reading frame ("uORF") contained in the 5' UTR of the gene. As used herein, the term "uORF" refers to an upstream open reading frame that is in the 5' UTR of the main open reading frame, i.e., that encodes a functional protein, of a mRNA.

As used herein, a "control gene" can be any gene that is not identical to a target gene being used. In a preferred embodiment, a control gene is a gene that does not contain a GEM. In a most preferred embodiment, a control gene is a target gene with GEM sequence removed or altered to be ineffective.

Target Genes

As used herein, the term "target gene" refers to a gene or nucleotide sequence encoding a protein or polypeptide of interest. In a preferred embodiment, target genes are selected for investigation based on 1) role of a target gene in a disease phenotype; 2) post-transcriptional control of a target gene's expression; and 3) commercial considerations, including but not limited to medical need, market size, and competition.

In a highly preferred embodiment, a target gene can be myostatin, utrophin, alpha 7 integrin, insulin like growth factor 1, or phospholamban. In a most preferred embodiment, a target gene can be utrophin isoform A, alpha 7 integrin isoforms X2A, X2DA, X2B, and X2DB (which are muscle specific), insulin like growth factor 1 isoform exon1-Ea expressed in extrahepatic tissues, or insulin like growth factor 1 isoform exon1-MGF expressed specifically in skeletal muscle.

In a preferred embodiment, target genes are selected from the group of target genes with a role in a disease or condition including, but not limited to, skin disease, cancer, inflammatory diseases, asthma, rheumatoid arthritis, multiple sclerosis (MS), Alzheimer's disease, autoimmunity, systemic lupus erythematosus (SLE), Crohn's disease, genetic diseases, diabetes, obesity, neurologic disease, central nervous system (CNS) diseases, Parkinson's disease, pain response abnormality, schizophrenia, Huntington's disease, cardiovascular disease, anti-infective diseases, human immune deficiency (HIV), hepatitis C virus (HCV), hepatitis B virus (HBV), hepatitis A virus (HAV), and cholera.

Particularly preferred target genes can have a role in more than one disease, including, but not limited to, combinations such as cancer and inflammatory diseases; inflammatory diseases and asthma, rheumatoid arthritis, multiple sclerosis, Alzheimer's disease, autoimmunity, SLE, Crohn's disease, or combinations of any or all of these; diabetes and obesity; diabetes and neurologic disease; CNS and Alzheimer's disease, pain response abnormality, Parkinson's disease, Huntington's disease, schizophrenia, anti-infective diseases and inflammatory diseases, cancer, HIV, HCV, HBV, HAV, cholera, or combinations of any or all of these; and combinations of these disease combinations.

In a most preferred embodiment, target genes have specific functions in promoting the disease or condition, such as, but not limited to, enzymes of sugar metabolism, involved in glucose homeostasis control, and involved in satiety and weight control. In a preferred embodiment, target genes do not include bovine growth factor hormone, adenaline repeats, reporter sequences, or epitope tags like myc or HLA.

Reporter Genes

As used herein, a "reporter gene" is any gene whose expression can be measured. In a preferred embodiment, a reporter gene does not have any UTRs. In a more preferred embodiment, a reporter gene is a contiguous open reading frame. In another preferred embodiment, a reporter gene can have a previously determined reference range of detectable expression.

Constructs of the invention can comprise one or more reporter genes fused to one or more UTRs. For example, specific RNA sequences, RNA structural motifs, and/or RNA structural elements that are known or suspected to modulate UTR-dependent expression of a target gene can be fused to the reporter gene. A reporter gene of the present invention encoding a protein, a fragment thereof, or a polypeptide, can also be linked to a propeptide encoding region. A propeptide is an amino acid sequence found at the amino terminus of a proprotein or proenzyme. The resulting polypeptide is known as a propolypeptide or proenzyme (a zymogen in some cases). Propolypeptides are generally inactive and can be converted to mature active polypeptides by catalytic or autocatalytic cleavage of the propeptide from the propolypeptide or proenzyme.

A reporter gene can express a selectable or screenable marker. Selectable markers may also be used to select for organisms or cells that contain exogenous genetic material. Examples of such include, but are not limited to: a neo gene (which codes for kanamycin resistance and can be selected for using kanamycin), GUS, green fluorescent protein (GFP), neomycin phosphotransferase II (nptII), luciferase (LUX), or an antibiotic resistance coding sequence. Screenable markers can be used to monitor expression. Exemplary screenable markers include: a β-glucuronidase or uidA gene (GUS) which encodes an enzyme for which various chromogenic substrates are known; a β-lactamase gene, a gene which encodes an enzyme for which various chromogenic substrates are known (e.g., PADAC, a chromogenic cephalosporin); a luciferase gene; a tyrosinase gene, which encodes an enzyme capable of oxidizing tyrosine to DOPA and dopaquinone which in turn condenses to melanin; and α-galactosidase, which can be used in colormetric assays.

Included within the terms "selectable or screenable marker genes" are also genes that encode a secretable marker whose secretion can be detected as a method of identifying or selecting for transformed cells. Examples include markers that encode a secretable antigen that can be identified by antibody interaction, or even secretable enzymes, which can be detected utilizing their inherent biochemical properties.

Secretable proteins fall into a number of classes, including small, diffusible proteins which are detectable, (e.g., by ELISA), or small active enzymes which are detectable in extracellular solution (e.g., α-amylase, β-lactamase, phosphinothricin transferase). Other possible selectable or screenable marker genes, or both, are apparent to those of skill in the art.

A reporter gene can express a fusion protein. As such, the fusion protein can be a fusion of any reporter gene operably linked to another gene, or fragment thereof. For instance, the expressed fusion protein can provide a "tagged" epitope to facilitate detection of the fusion protein, such as GST, GFP, FLAG, or polyHIS. Such fusions preferably encode between 1 and 50 amino acids, more preferably between 5 and 30 additional amino acids, and even more preferably between 5 and 20 amino acids. In one embodiment, a fusion protein can be a fusion protein that includes in whole or in part of a target protein sequence.

Alternatively, the fusion can provide regulatory, enzymatic, cell signaling, or intercellular transport functions. For example, a sequence encoding a signal peptide can be added to direct a fusion protein to a particular organelle within a eukaryotic cell. Such fusion partners preferably encode between 1 and 1000 additional amino acids, more preferably between 5 and 500 additional amino acids, and even more preferably between 10 and 250 amino acids.

In one embodiment, a reporter gene includes one or more mutations (e.g., one or more substitutions, deletions and/or additions) that do not alter the ability of reporter gene expression to be measured. In a highly preferred embodiment, the reporter gene contains one or more restriction sites that can be used for cloning, such as a BamHI and a Not I site, and the restriction sites do not alter the function of the reporter gene. In a particularly preferred embodiment, a restriction site is downstream from the start codon of the open reading frame that encodes the reporter polypeptide, and another restriction site is upstream from the stop codon of the open reading frame that encodes the reporter polypeptide.

The present invention also provides for a reporter gene flanked by one or more untranslated regions (e.g., the 5' UTR, 3' UTR, or both the 5' UTR and 3' UTR of the target gene). In addition, the present invention provides for a reporter gene flanked by one or more UTRs of a target gene, where the UTR contains one or more mutations (e.g., one or more substitutions, deletions and/or additions). In a preferred embodiment, the reporter gene is flanked by both 5' and 3' UTRs so that compounds that interfere with an interaction between the 5' and 3' UTRs can be identified.

In another preferred embodiment, a stable hairpin secondary structure is inserted into the UTR, preferably the 5' UTR of the target gene. For example, in cases where the 5' UTR possesses IRES activity, the addition of a stable hairpin secondary structure in the 5' UTR can be used to separate cap-dependent from cap-independent translation (see, e.g., Muhlrad et al., 1995, *Mol. Cell. Biol.* 15(4):2145-56, the disclosure of which is incorporated by reference in its entirety). In another embodiment, an intron is inserted into a UTR (preferably, the 5' UTR) or at the 5' end of an ORF of a reporter gene. For example, but not as a limitation, in cases where an RNA possesses instability elements, an intron, e.g., first intron of the human elongation factor one alpha (EF-1 alpha), can be cloned into a UTR (preferably, the 5' UTR) or a 5' end of the ORF to increase expression (see, e.g., Kim et al., 2002, *J Biotechnol* 93(2):183-7, the disclosure of which is incorporated by reference in its entirety). As used herein, an intron can be naturally occurring in a gene having at least two splice sites. In a preferred embodiment, an intron can be naturally occurring in a UTR. In an alternative embodiment, an intron can be naturally occurring in a heterologous gene. In an alternative embodiment, an intron can be an unnatural sequence bordered by 5' and 3' splice sites. In a preferred embodiment, both a stable hairpin secondary structure and an intron are added to the reporter gene construct. In a more preferred embodiment, the stable hairpin secondary structure is cloned into the 5' UTR and the intron is added at the 5' end of the sequence encoding the reporter polypeptide.

The reporter gene can be positioned such that the translation of that reporter gene is dependent upon the mode of translation initiation, such as, but not limited to, cap-dependent translation or cap-independent translation (i.e., translation via an internal ribosome entry site). Alternatively, where the UTR contains an upstream open reading frame, the reporter gene can be positioned such that the reporter protein is translated only in the presence of a compound that shifts the reading frame of the UTR so that the formerly untranslated open reading frame is then translated.

The reporter gene constructs can be monocistronic or multicistronic. A multicistronic reporter gene construct may encode 2, 3, 4, 5, 6, 7, 8, 9, 10 or more, or in the range of 2-5, 5-10 or 10-20 reporter genes. For example, a bicistronic reporter gene construct comprising, in the following order going downstream, a promoter, a first reporter gene, a 5' UTR of a target gene, a second reporter gene and optionally, a 3' UTR of a target gene. In such a reporter construct, the transcription of both reporter genes is capable of being driven by the promoter. In this example construct, the present invention includes the translation of the mRNA from the first reporter gene by a cap-dependent scanning mechanism and the translation of the mRNA from the second reporter gene by a cap-independent mechanism, for example by an IRES. In such a case, the IRES-dependent translation of a mRNA of the second reporter gene can be normalized against the cap-dependent translation of the first reporter gene. In a particularly preferred embodiment of the present invention, a stable hairpin secondary structure is inserted immediately downstream of the stop codon of the first reporter gene to ensure that translation of the second reporter gene cannot occur via cap-dependent translation.

Reporter genes can be expressed in vitro or in vivo. In vivo expression can be in a suitable bacterial or eukaryotic host. Suitable methods for expression are described by Sambrook et al., *Molecular Cloning: A Laboratory Manual*, Second Edition, Cold Spring Harbor Laboratory Press, Cold Spring Harbor, N.Y. (1989); Haymes et al., *Nucleic Acid Hybridization, A Practical Approach*, IRL Press, Washington, D.C. (1985); or similar texts. Fusion protein or peptide molecules of the invention are preferably produced via recombinant approach. These proteins and peptide molecules can be derivatized to contain carbohydrate or other moieties (such as keyhole limpet hemocyanin, etc.).

Linked

As used herein, linked can mean physically linked, operably linked, flanked, or any of these in combination. In a preferred embodiment, the promoter is operably linked and physically linked to a nucleic acid sequence of the present invention.

As used herein, physically linked means that the physically linked nucleic acid sequences are located on the same nucleic acid molecule, for example a promoter can be physically linked to a reporter gene as part of a construct. If a physical linkage is proximal, the linkage can be either direct or indirect. By way of example, a promoter that is proximally linked to a reporter gene as part of a construct can be directly linked to the reporter gene so that there is no gap between the promoter and the reporter gene. In such a case, the promoter is immediately followed by the reporter gene and there are no nucleic acid residues which do not belong to either the promoter or the reporter gene between the two elements of the construct. In an example of a promoter indirectly proximally linked to a reporter gene, nucleic acid residues which are not a part of the promoter or reporter gene exist between the promoter and reporter gene. The gap, where the nucleic acid sequence that is not derived from the promoter or reporter gene, may include for example, without limitation, a fragment, or a portion of a bovine growth hormone gene, in particular the UTR or a fragment thereof; thymidine kinase; lambda; SV40. A gap can be composed of more than approximately three stop codons. A gap can have less than five stop codons in different codon reading frames. Moreover, in one embodiment there can be multiple restriction sites, also referred to as a polylinker, between the promoter and reporter gene. In an alternative embodiment there are not multiple restriction sites, also referred to as a polylinker, between the promoter and reporter gene. In a preferred embodiment, the nucleic acid sequence in the gap is located on the nucleic acid sequence of the vector prior to cloning in the an agent of the present invention.

If the reporter gene is directly linked to a UTR of a target gene, at least one of the terminal nucleic acid residues of the reporter gene can be chemically bonded to a nucleic acid sequence from a UTR of a target gene. A UTR of a target gene (herein referred to as a "target UTR") can be the entire UTR or a fragment thereof. The reporter gene can be proximally linked indirectly to a UTR of a target gene if a terminal nucleic acid residue of the reporter gene is not chemically bonded to a nucleic acid residue from a UTR of a target gene. In a preferred embodiment, if the reporter gene is proximally linked indirectly to a UTR of a target gene, the last nucleic acid residue of the reporter gene can be about 3 residues away from a UTR of a target gene or greater than 5 but less than 20 residues away from a UTR of a target gene. If the reporter gene is directly linked to a UTR of a target gene, but that UTR of a target gene is directly followed by a UTR not in a target gene, the reporter gene is directly linked to the UTR of a target gene. In a most preferred embodiment, the reporter gene is directly linked to a UTR of a target gene as a mature mRNA, such as after a splicing event, and can have been interrupted by a UTR not in a target gene at an earlier stage in the gene expression process.

A preferred embodiment of the present invention also provides for specific nucleic acid molecules containing a reporter gene flanked by one or more UTRs of a target gene. A UTR of a target gene refers to the nucleic acid sequence of any UTR in a target gene. In this preferred embodiment, the one or more UTRs of a target gene can be physically linked, operably linked, or operably and physically linked to the reporter gene. In a more preferred embodiment, a reporter gene is flanked by both a 5' and 3' UTR of a target gene so that compounds that effect an interaction between 5' and 3' UTRs can be identified. The effect can result in an increase or decrease in the free energy of such an interaction.

In a preferred embodiment, the reporter gene is flanked by both 5' and 3' UTRs of one or more target genes so that compounds that interfere with an interaction between the 5' and 3' UTRs can be identified. In a more preferred embodiment, the reporter gene is flanked by a 5' and 3' UTRs of one target gene, and the reporter gene is physically, operably, or physically and operably linked to the UTRs of one target gene. In a most preferred embodiment, a reporter gene is proximally linked, either directly or indirectly, to one or more UTRs of a target gene.

UTRs

Agents and constructs of the invention include nucleic acid molecules with an untranslated region (UTR). In a preferred aspect, a UTR refers to a UTR of an mRNA, i.e. the region of the mRNA that is not translated into protein. In a preferred embodiment, a UTR contains one or more regulatory elements that modulate untranslated region-dependent regulation of gene expression. In a particularly preferred embodiment, a UTR is a 5' UTR, i.e., upstream of the coding region, or a 3' UTR, i.e., downstream of the coding region. In a more preferred embodiment, a UTR contains one or more GEMs.

A UTR of the present invention can be operatively, physically, or operatively and physically linked to a target gene, target RNA, or reporter gene. In a preferred embodiment of the present invention, a UTR of the present invention is physically linked to a reporter gene. The physical, operable, or physical and operable linkage may be upstream, downstream, or internal to the reporter gene. As used herein, operably linked means that the operably linked nucleic acid sequences exhibit their deserved function. For example, a promoter can be operably linked to a reporter gene.

In a preferred embodiment of the present invention, a UTR of the present invention is physically linked upstream of the reporter gene and another UTR is physically linked downstream of the reporter gene. In a particularly preferred embodiment, a 5' UTR of the present invention contains or consists of a GEM and is physically and operatively linked upstream of a reporter gene, and a 3' UTR is physically and operatively linked downstream of the reporter gene. In an alternatively preferred embodiment, a 3' UTR of the present invention contains or consists of a GEM and is physically and operatively linked downstream of a reporter gene, and a 5' UTR is physically and operatively linked upstream of the reporter gene. In an alternatively preferred embodiment, a 5' UTR of the present invention contains or consists of a GEM and is physically and operatively linked upstream of a reporter gene, and a 3' UTR of the present invention contains or consists of a GEM and is physically and operatively linked downstream of the reporter gene. One or more GEMs in a 5' UTR, in a 3' UTR, or both in the 5' and 3' UTRs can act independently or dependently of linked nucleic acid sequence.

In a preferred embodiment of the present invention, a UTR of the present invention is physically linked to reporter gene containing an intron. In a more preferred embodiment of the present invention, a UTR of the present invention containing a GEM is physically linked to a reporter gene containing an intron. In a preferred embodiment of the present invention, a 5' UTR of the present invention is physically linked upstream of a reporter gene and contains an intron internal to the UTR. In a preferred embodiment of the present invention, a UTR of the present invention is physically linked upstream of a reporter gene and a UTR is physically linked downstream of the reporter gene.

A gene can include regions preceding and following a nucleic acid sequence encoding a polypeptide as well as introns between the exons of the coding region. A typical mRNA contains a 5' cap, a 5' untranslated region ("5'UTR") upstream of a start codon, an open reading frame, which is also referred to as a coding sequence that encodes a stable RNA or a functional protein, a 3' untranslated region ("3' UTR") downstream of the termination codon, and a poly(A) tail. A nucleic acid of the present invention can include a UTR containing a GEM, a GEM, a fragment of either, or a complement of any of these. In a preferred embodiment, a cis-dependent RNA-based GEM maps to the 5' UTR, the 3'UTR, or the 5'UTR and 3'UTR.

GEMs

As referred to herein, a GEM is a gene expression modulator that regulates expression of a target gene after transcription. In one aspect, a GEM is not a full-length sequence of a UTR from a target gene (hereafter referred to as "a target UTR"). In a preferred aspect, a GEM is not a full-length 5' UTR or a full-length 3' UTR. A GEM can include the nucleic acid sequence involved in modulation of expression as a result of interaction between UTRs, preferably the interaction between a 5' UTR and a 3' UTR from the same gene, a UTR pair. In one embodiment, a GEM in one target gene can have primary nucleic acid sequence similarity to a GEM in a different target gene. Alternatively, there may not be any primary nucleic acid sequence similarity in GEMs of similar function. In a preferred embodiment, a GEM in one target gene can have a secondary, tertiary, or secondary and tertiary structure similar to a GEM in a different target gene. Examples of GEMs include, but are not limited to, IRES elements, upstream ORFs, and AREs.

In one embodiment, a GEM of the present invention is a nucleic acid sequence in a UTR, which modulates UTR-dependent gene expression after transcription of the gene. A GEM can be a nucleic acid sequence located anywhere in a target gene. Examples of 5' UTR regulatory elements, such as GEMs of the present invention, include the iron response element ("IRE"), internal ribosome entry site ("IRES"), upstream open reading frame ("uORF"), male specific lethal element ("MSL-2"), G-quartet element, and 5'-terminal oligopyrimidine tract ("TOP") (reviewed in Keene & Tenenbaum, 2002, Mol Cell 9:1161 and Translational Control of Gene Expression, Sonenberg, Hershey, and Mathews, eds., 2000, CSHL Press). Examples of 3' UTR regulatory elements, such as GEMs of the present invention, include AU-rich elements ("AREs"), Selenocysteine insertion sequence ("SECIS"), histone stem loop, cytoplasmic polyadenylation elements ("CPEs"), nanos translational control element, amyloid precursor protein element ("APP"), translational regulation element ("TGE"), direct repeat element ("DRE"), bruno element ("BRE"), 15-lipoxygenase differentiation control element (15-LOX-DICE), and G-quartet element (reviewed in Keene & Tenenbaum, 2002, Mol Cell 9:1161). GEMs include nucleic acid sequences in a UTR that modulate other GEM sequences.

By way of example, a GEM in the 5' UTR of a target gene can modulate the GEM-dependent expression of a GEM in the same or another UTR, for example, a GEM in the 3' UTR of the same target gene. In a particularly preferred embodiment, a GEM can consist of the interaction between sequences of the 5' and 3' UTR of the same target gene where the GEM activity requires the presence of both the 5' and 3' UTR whose sequence elements cannot function independently). GEMs of the present invention can be located in any position within a construct and not limited to the 5' UTR or 3' UTR regions of a molecule. A GEM of the present invention can be operatively, physically, or operatively and physically linked to a UTR. In an alternative embodiment of the present invention, a GEM of the present invention is a UTR of the present invention.

In one embodiment of the present invention, a GEM is located between about 1 to about 100 residues upstream from the initiation codon of an open reading frame in a mRNA, between about 150 to about 250 residues upstream from the initiation codon, or between about 300 to about 500 residues upstream from the initiation codon. In a most preferred embodiment, a GEM is within about 30 residues upstream from the initiation codon. In addition to or independent of other GEMs in a nucleic acid molecule, a GEM of the present invention can be located between about 1 to about 100 residues downstream from the stop codon of an open reading frame in a mRNA, between about 150 to about 250 residues downstream from the stop codon, or between about 300 to about 500 residues downstream from the stop codon. In a preferred embodiment, a GEM is within about 30 residues downstream from the stop codon.

Further examples of embodiments of the present invention include a GEM within about 1000 residues upstream from the 5' end of a main ORF, within about 500 residues upstream from the 5' end of a main ORF, or within about 200 residues upstream from the 5' end of a main ORF, or within about 100 residues upstream from the 5' end of a main ORF. A GEM of the present invention can also be located within about 1000 residues downstream from the 3' end of a main ORF, within about 500 residues downstream from the 3' end of a main ORF, or within about 200 residues downstream from the 3' end of a main ORF or within about 100 residues downstream from the 3' end of a main ORF. In a preferred embodiment, a GEM is about 5 residues down stream from the stop codon of a main ORF.

Constructs of the present invention can have more or fewer components than described above. For example, constructs of the present invention can include genetic elements, including but not limited to, 3' transcriptional terminators, 3' polyadenylation signals, other untranslated nucleic acid sequences, transit or targeting sequences, selectable or screenable markers, promoters, enhancers, and operators, as desired. Constructs of the present invention can also contain a promoter-less gene that may utilize an endogenous promoter upon insertion into a host cell chromosome.

Alternatively, sequences encoding nucleic acid molecules of the present invention can be cloned into a vector for the production of an mRNA probe. Such vectors are known in the art, are commercially available, and can be used to synthesize RNA probes in vitro by addition of labeled nucleotides and an appropriate RNA polymerase such as T7, T3, or SP6. These procedures can be conducted using a variety of commercially available kits (for example, Amersham Biosciences Inc., Piscataway, N.J.; and Promega Co, Madison, Wis.).

Modulation of Gene Expression by Nucleic Acid Molecules of the Present Invention Modulation of gene expression can result in more or less gene expression. Many approaches for modulating gene expression using nucleic acid molecules of the present invention are known to one skilled in the art. For example, overexpression of a gene product can be the result from transfection of a construct of the present invention into a mammalian cell. Similarly, down-regulation can be the result from transfection of a construct of the present invention into a mammalian cell. Other non-limiting examples include anti-sense techniques like RNA interference (RNAi), transgenic animals, hybrids, and ribozymes. The following examples are provided by way of illustration, and are not intended to be limiting of the present invention.

Cellular Mechanisms

As used herein, the term "UTR-dependent expression" refers to the regulation of gene expression through a UTR at the level of mRNA expression, i.e., after transcription of the gene has begun until the protein or the RNA product(s) encoded by the gene has been degraded. In a preferred embodiment, the term "UTR-dependent expression" refers to the regulation of mRNA stability or translation. In a more preferred embodiment, the term "UTR-dependent expression" refers to the regulation of gene expression through regulatory elements present in a UTR. Altering the sequence of a GEM within a UTR of target gene can change the amount of UTR-dependent expression observed for that target gene.

As used herein, a "UTR-affected mechanism" is a cellular mechanism that discriminates between UTRs based on their nucleic acid sequence or based on properties that are a function of their sequence such as the secondary, tertiary, or quaternary structure. In an embodiment of the present invention, a UTR-affected mechanism discriminates between UTRs based on a UTR sequence-dependent higher order complex assembly of trans-acting factors. Modulation of the UTR-dependent expression of a target gene can be due to a change in how a UTR-affected mechanism acts on the target gene. For example, a UTR in a target gene can contain an IRES, which affects target gene expression via a UTR-affected mechanism.

In a preferred embodiment, a UTR-affected mechanism can be a main ORF-independent mechanism. As used herein, a "main ORF-independent mechanism" refers to a cellular pathway or process, wherein at least one step relates to gene expression and is not dependent on the nucleic acid sequence of the main open reading frame. In a preferred embodiment, a UTR-affected mechanism is a main ORF-independent, UTR-affected mechanism.

In order to exclude the possibility that a particular compound is functioning solely by modulating the expression of a target gene in a UTR-independent manner, one or more mutations may be introduced into the UTRs operably linked to a reporter gene and the effect on the expression of the reporter gene in a reporter gene-based assay described herein can be determined. For example, a reporter gene construct comprising the 5' UTR of a target gene may be mutated by deleting a fragment of the 5' UTR of the target gene or substituting a fragment of the 5' UTR of the target gene with a fragment of the 5' UTR of another gene and measuring the expression of the reporter gene in the presence and absence of a compound that has been identified in screening assays of the present invention or of an assay well known to the skilled artisan. If the deletion of a fragment of the 5' UTR of the target gene or the substitution of a fragment of the 5' UTR of the target gene with a fragment of the 5' UTR of another gene affects the ability of the compound to modulate the expression of the reporter gene, then the fragment of the 5' UTR deleted or substituted plays a role in the ability of the compound to regulate reporter gene expression and the regulation, at least in part, is UTR-dependent.

Alternatively or in conjunction with the tests described above, the possibility that a particular compound is functioning solely by modulating the expression of a target gene in an UTR-independent manner can be determined by changing the vector utilized as a reporter construct. The UTRs flanked by a reporter gene from the first reporter construct in which an effect on reporter gene expression was detected following exposure to a compound may be inserted into a new reporter construct that has, e.g., different transcriptional regulation elements (e.g., a different promoter) and a different selectable marker. The level of reporter gene expression in the presence of the compound can be compared to the level of reporter gene expression in the absence of the compound or in the presence of a control (e.g., PBS). If there is no change in the level of expression of the reporter gene in the presence of the compound relative to the absence of the compound or in the presence of a control, then the compound probably is functioning in an UTR-independent manner.

By way of further example, additional tests can be used to evaluate that a particular compound functions by modulating the expression of a target gene in an UTR-independent manner. This can be done, for example, by measuring the effect of the compound when the reporter gene is operably linked to UTRs from another target gene. The potency with which the compound effects the level of reporter gene expression operably linked to the original UTRs can be compared to the potency with which the compound effects the level of reporter gene expression operably linked to the control UTRs. If the compound is active only when the original UTRs are operably linked to the reporter gene and shows a significant decrease in activity when the control UTRs are operably linked to the reporter gene, then the compound is a candidate compound that functions in a UTR-independent manner.

Compounds, identified in assays of the present invention, that are capable of modulating UTR-dependent expression of a target gene (for convenience referred to herein as a "lead" compound) can be further tested for UTR-dependent binding to the target RNA (which contains at least one UTR, and preferably at least one element of an UTR, for example a GEM). Furthermore, by assessing the effect of a compound on target gene expression, cis-acting elements, i.e., specific nucleotide sequences, that are involved in UTR-dependent expression may be identified. RNA binding assays, subtraction assays, and expressed protein concentration and activity assays are examples methods to determine UTR-dependent expression of a gene.

Hybrids

In one aspect of the present invention, a hybrid of a compound and a GEM of the present invention is a hybrid formed between two non-identical molecules. In a preferred aspect, a hybrid can be formed between two nucleic acid molecules. For example, a hybrid can be formed between two ribonucleic acid molecules, between a ribonucleic acid molecule and a deoxyribonucleic acid molecule, or between derivatives of either. In alternative embodiment, a hybrid can be formed between a nucleic acid of the present invention and a non-nucleic acid molecule. In a preferred embodiment, a hybrid can be formed between a nucleic acid molecule and a non-nucleic acid molecule, for example, a polypeptide or a non-peptide therapeutic agent.

Ribozymes

In one aspect of the present invention, the activity or expression of a gene is regulated by designing trans-cleaving catalytic RNAs (ribozymes) specifically directed to a nucleic acid molecule of the present invention. In an alternate aspect, the activity or expression of a gene is regulated by designing trans-cleaving catalytic RNAs (ribozymes) specifically directed to a nucleic acid molecule of the present invention.

Ribozymes are RNA molecules possessing endoribonuclease activity. Ribozymes are specifically designed for a particular target, and the target message contains a specific nucleotide sequence. They are engineered to cleave any RNA species site-specifically in the background of cellular RNA. The cleavage event renders the mRNA unstable and prevents protein expression. Importantly, ribozymes can be used to inhibit expression of a gene of unknown function for the purpose of determining its function in an in vitro or in vivo context, by detecting a phenotypic effect.

One commonly used ribozyme motif is the hammerhead, for which the substrate sequence requirements are minimal. Design of the hammerhead ribozyme, and the therapeutic uses of ribozymes, are disclosed in Usman et al., *Current Opin. Strict. Biol.* 6:527-533 (1996). Ribozymes can also be prepared and used as described in Long et al., *FASEB J.* 7:25 (1993); Symons, *Ann. Rev. Biochem.* 61:641 (1992); Perrotta et al., *Biochem.* 31:16-17 (1992); Ojwang et al., *PNAS* 89:10802-10806 (1992); and U.S. Pat. No. 5,254,678.

Ribozyme cleavage of HIV-I RNA, methods of cleaving RNA using ribozymes, methods for increasing the specificity of ribozymes, and the preparation and use of ribozyme fragments in a hammerhead structure are described in U.S. Pat. Nos. 5,144,019; 5,116,742; and 5,225,337 and Koizumi et al., *Nucleic Acid Res.* 17:7059-7071 (1989). Preparation and use of ribozyme fragments in a hairpin structure are described by Chowrira and Burke, *Nucleic Acids Res.* 20:2835 (1992). Ribozymes can also be made by rolling transcription as described in Daubendiek and Kool, *Nat. Biotechnol.* 15(3): 273-277 (1997).

The hybridizing region of the ribozyme may be modified or may be prepared as a branched structure as described in Horn and Urdea, *Nucleic Acids Res.* 17:6959-67 (1989). The basic structure of the ribozymes may also be chemically altered in ways familiar to those skilled in the art, and chemically synthesized ribozymes can be administered as synthetic oligonucleotide derivatives modified by monomeric units. In a therapeutic context, liposome mediated delivery of ribozymes improves cellular uptake, as described in Birikh et al., *Eur. J. Biochem.* 245:1-16 (1997).

Ribozymes of the present invention also include RNA endoribonucleases (hereinafter "Cech-type ribozymes") such as the one which occurs naturally in *Tetrahymena thermophila* (known as the IVS, or L-19 IVS RNA) and which has been extensively described by Thomas Cech and collaborators (Zaug et al., *Science* 224:574-578 (1984); Zaug and Cech, *Science* 231:470-475 (1986); Zaug et al., *Nature,* 324: 429-433 (1986); WO 88/04300; Been and Cech, *Cell* 47:207-216 (1986)). The Cech-type ribozymes have an eight base pair active site which hybridizes to a target RNA sequence whereafter cleavage of the target RNA takes place. The invention encompasses those Cech-type ribozymes which target eight base-pair active site sequences that are present in a target gene.

Ribozymes can be composed of modified oligonucleotides (e.g., for improved stability, targeting, etc.) and should be delivered to cells which express the target gene in vivo. A preferred method of delivery involves using a DNA construct "encoding" the ribozyme under the control of a strong constitutive pol III or pol II promoter, so that transfected cells will produce sufficient quantities of the ribozyme to destroy endogenous messages and inhibit translation. Because ribozymes, unlike antisense molecules, are catalytic, a lower intracellular concentration is required for efficiency.

Using the nucleic acid sequences of the invention and methods known in the art, ribozymes are designed to specifically bind and cut the corresponding mRNA species. Ribozymes thus provide a method to inhibit the expression of any of the proteins encoded by the disclosed nucleic acids or their full-length genes. The nucleid acid sequence of the full-length gene need not be known in order to design and use specific inhibitory ribozymes. In the case of a nucleic acid or cDNA of unknown function, ribozymes corresponding to the specific nucleotide sequence can be tested in vitro for efficacy in cleaving the target transcript. Those ribozymes that effect cleavage in vitro are further tested in vivo. The ribozyme can also be used to generate an animal model for a disease, as described in Birikh et al., *Eur. J. Biochem.* 245:1-16 (1997). An effective ribozyme is used to determine the function of the gene of interest by blocking its expression and detecting a phenotypic change in the cell. Where the gene is found to be a mediator in a disease, an effective ribozyme is designed and delivered in a gene therapy for blocking expression of the gene.

Therapeutic and functional genomic applications of ribozymes begin with knowledge of a portion of the coding sequence of the gene to be inhibited. Thus, for many genes, a partial nucleic acid sequence provides adequate sequence for constructing an effective ribozyme. A target cleavage site is selected in the target sequence, and a ribozyme is constructed based on the 5' and 3' nucleotide sequences that flank the cleavage site. Retroviral vectors are engineered to express monomeric and multimeric hammerhead ribozymes targeting the mRNA of the target coding sequence. These monomeric and multimeric ribozymes are tested in vitro for an ability to cleave the target mRNA. A cell line is stably transduced with the retroviral vectors expressing the ribozymes, and the transduction is confirmed by Northern blot analysis and reverse-transcription polymerase chain reaction (RT-PCR). The cells are screened for inactivation of the target mRNA by such indicators as reduction of expression of disease markers or reduction of the gene product of the target mRNA.

Cells and Organisms

Nucleic acid molecules that may be used in cell transformation or transfection can be any of the nucleic acid molecules of the present invention. Nucleic acid molecules of the present invention can be introduced into a cell or organism. A heterologous nucleic acid molecule can be an RNA molecule produced in a different cell or produced by in vitro transcription (Ambion, Inc., Austin, Tex.) and transfected directly into a cell of interest.

A host cell strain can be chosen for its ability to modulate the expression of the inserted sequences, to process an expressed reporter gene in the desired fashion, or based on the expression levels of endogenous or heterologous target genes. Mammalian cell lines available as hosts for expression are known in the art and include many immortalized cell lines available from the American Type Culture Collection (ATCC, Manassas, Va.), such as HeLa cells, Chinese hamster ovary (CHO) cells, baby hamster kidney (BHK) cells and a number of other cell lines. Non-limiting examples of suitable mammalian host cell lines include those shown below in Table 1.

TABLE 1

Mammalian Host Cell Lines

| Host Cell | Origin | Source |
|---|---|---|
| HepG-2 | Human Liver Hepatoblastoma | ATCC HB 8065 |
| CV-1 | African Green Monkey Kidney | ATCC CCL 70 |
| LLC-MK$_2$ | Rhesus Monkey Kidney | ATCC CCL 7 |
| 3T3 | Mouse Embryo Fibroblasts | ATCC CCL 92 |
| AV12-664 | Syrian Hamster | ATCC CRL 9595 |
| HeLa | Human Cervix Epitheloid | ATCC CCL 2 |
| RPMI8226 | Human Myeloma | ATCC CCL 155 |
| H4IIEC3 | Rat Hepatoma | ATCC CCL 1600 |
| C127I | Mouse Fibroblast | ATCC CCL 1616 |
| 293 | Human Embryonal Kidney | ATCC CRL 1573 |
| HS-Sultan | Human Plasma Cell Plasmocytoma | ATCC CCL 1484 |
| BHK-21 | Baby Hamster Kidney | ATCC CCL 10 |
| CHO-K1 | Chinese Hamster Ovary | ATCC CCL 61 |

In a preferred aspect, cells of the present invention can be cells of an organism. In a more preferred aspect, the organism is a mammal. In a most preferred aspect, the mammal is a human. In another more preferred aspect, the organism is a non-human mammal, preferably a mouse, rat, or a chimpanzee. In one aspect of the present invention, cells can be pluripotent or differentiated.

A nucleic acid of the present invention can be naturally occurring in the cell or can be introduced using techniques such as those described in the art. There are many methods for introducing transforming DNA segments into cells, but not all are suitable for delivering DNA to eukaryotic cells. Suitable methods include any method by which DNA can be introduced into a cell, such as by direct delivery of DNA, by desiccation/inhibition-mediated DNA uptake, by electroporation, by agitation with silicon carbide fibers, by acceleration of DNA coated particles, by chemical transfection, by lipofection or liposome-mediated transfection, by calcium chloride-mediated DNA uptake, etc. For example, without limitation, Lipofectamine® (Invitrogen Co., Carlsbad, Calif.) and Fugene® (Hoffmann-La Roche Inc., Nutley, N.J.) can be used for transfection of nucleic acid molecules, such as constructs and small interfering RNAs (siRNA), into several mammalian cells. Alternatively, in certain embodiments, acceleration methods are preferred and include, for example, microprojectile bombardment and the like. Within the scope of this invention, the transfected nucleic acids of the present invention may be expressed transiently or stably. Such transfected cells can be in a two- or three-dimensional cell culture system or in an organism.

For example, without limitation, the construct may be an autonomously replicating construct, i.e., a construct that exists as an extrachromosomal entity, the replication of which is independent of chromosomal replication, e.g., a plasmid, an extrachromosomal element, a minichromosome, or an artificial chromosome. The construct may contain any approach for assuring self-replication. For autonomous replication, the construct may further comprise an origin of replication enabling the construct to replicate autonomously in the host cell. Alternatively, the construct may be one which, when introduced into the cell, is integrated into the genome and replicated together with the chromosome(s) into which it has been integrated. This integration may be the result of homologous or non-homologous recombination.

Integration of a construct or nucleic acid into the genome by homologous recombination, regardless of the host being considered, relies on the nucleic acid sequence of the construct. Typically, the construct contains nucleic acid sequences for directing integration by homologous recombination into the genome of the host. These nucleic acid sequences enable the construct to be integrated into the host cell genome at a precise location or locations in one or more chromosomes. To increase the likelihood of integration at a precise location, there should be preferably two nucleic acid sequences that individually contain a sufficient number of nucleic acids, preferably 400 residues to 1500 residues, more preferably 800 residues to 1000 residues, which are highly homologous with the corresponding host cell target sequence. This enhances the probability of homologous recombination. These nucleic acid sequences may be any sequence that is homologous with a host cell target sequence and, furthermore, may or may not encode proteins.

Stable expression is preferred for long-term, high-yield production of recombinant proteins. For example, to generate cell lines that stably express a reporter gene, cell lines can be transformed using expression constructs that can contain viral origins of replication and/or endogenous expression elements and a selectable marker gene on the same or on a separate construct. Following the introduction of the construct, cells can be allowed to grow for 1-2 days in an enriched medium before they are switched to a selective medium. The purpose of the selectable marker is to confer resistance to selection, and its presence allows growth and recovery of cells that successfully express the introduced construct. Resistant clones of stably transformed cells can be proliferated using tissue culture techniques appropriate to the cell type. See, for example, *Animal Cell Culture*, R. I. Freshney, ed., 1986.

Any number of selection systems can be used to recover transformed cell lines. These include, but are not limited to, the herpes simplex virus thymidine kinase (Wigler et al., Cell 11:223-32 (1977)) and adenine phosphoribosyltransferase (Lowy et al., *Cell* 22:817-23 (1980)) genes which can be employed in tk⁻ or aprt⁻ cells, respectively. Also, antimetabolite, antibiotic, or herbicide resistance can be used as the basis for selection. For example, dhfr confers resistance to methotrexate (Wigler et al., *Proc. Natl. Acad. Sci.* 77:3567-70 (1980)), npt confers resistance to the aminoglycosides, neomycin and G-418 (Colbere-Garapin et al., *J. Mol. Biol.* 150: 1-14 (1981), and als and pat confer resistance to chlorsulfuron and phosphinotricin acetyltransferase, respectively. Additional selectable genes have been described. For example, trpB allows cells to utilize indole in place of tryptophan, and hisD allows cells to utilize histinol in place of histidine (Hartman & Mulligan, *Proc. Natl. Acad. Sci.* 85:8047-51 (1988)). Visible markers such as anthocyanins, β-glucuronidase and its substrate GUS, and luciferase and its substrate luciferin, can be used to identify transformants and to quantify the amount of transient or stable protein expression attributable to a specific construct system (Rhodes et al., *Methods Mol. Biol.* 55:121-131 (1995)).

Although the presence of marker gene expression suggests that a reporter gene is also present, its presence and expression may need to be confirmed. For example, if a sequence encoding a reporter gene is inserted within a marker gene sequence, transformed cells containing sequences that encode a reporter gene can be identified by the absence of marker gene function. Alternatively, a marker gene can be placed in tandem with a sequence encoding a reporter gene under the control of a single promoter. Expression of the marker gene in response to induction or selection usually indicates expression of a reporter gene.

Alternatively, host cells which contain and express a reporter gene and can be identified by a variety of procedures known to those of skill in the art. These procedures include, but are not limited to, DNA-DNA or DNA-RNA hybridizations and protein bioassay or immunoassay techniques that include membrane, solution, or chip-based technologies for the detection and/or quantification of nucleic acid or protein. For example, the presence of a reporter gene can be detected by DNA-DNA or DNA-RNA hybridization or amplification using probes or fragments or fragments of polynucleotides encoding a reporter gene. Nucleic acid amplification-based assays involve the use of oligonucleotides selected from sequences encoding a reporter gene to detect transformants that contain a reporter gene.

Screening Methods of the Present Invention

Another aspect of the present invention includes screening methods to identify agents and compounds that modulate gene expression and can result in more or less gene expression. Many methods for screening agents and compounds that modulating gene expression are known to one skilled in the art. For example, over-expression of a gene product can be the result from transfection of a construct of the present invention into a mammalian cell. Similarly, down-regulation can be the result from transfection of a construct of the present invention into a mammalian cell. Other non-limiting examples include anti-sense techniques like RNA interference (RNAi), transgenic animals, hybrids, and ribozymes. The following examples are provided by way of illustration, and are not intended to be limiting of the present invention.

Compound

The present invention includes methods for screening compounds capable of modulating gene expression.

Any compound can be screened in an assay of the present invention. In an embodiment, a compound includes a nucleic acid or a non-nucleic acid, such as a polypeptide or a non-peptide therapeutic agent. In a preferred embodiment, a nucleic acid can be a polynucleotide, a polynucleotide analog, a nucleotide, or a nucleotide analog. In a more preferred embodiment, a compound can be an antisense oligonucleotide, which are nucleotide sequences complementary to a specific DNA or RNA sequence of the present invention. Preferably, an antisense oligonucleotide is at least 11 nucleotides in length, but can be at least 12, 15, 20, 25, 30, 35, 40, 45, or 50 or more nucleotides long. Longer sequences also can be used. Antisense oligonucleotides can be deoxyribonucleotides, ribonucleotides, or a combination of both.

Nucleic acid molecules, including antisense oligonucleotide molecules, can be provided in a DNA construct and introduced into a cell. Nucleic acid molecules can be antisense or sense and double- or single-stranded. In a preferred embodiment, nucleic acid molecules can be interfering RNA (RNAi) or microRNA (miRNA). In a preferred embodiment, the dsRNA is 20-25 residues in length, termed small interfering RNAs (siRNA).

Oligonucleotides can be synthesized manually or by an automated synthesizer, by covalently linking the 5' end of one nucleotide with the 3' end of another nucleotide with non-phosphodiester internucleotide linkages such alkylphosphonates, phosphorothioates, phosphorodithioates, alkylphosphonothioates, alkylphosphonates, phosphoramidates, phosphate esters, carbamates, acetamidate, carboxymethyl esters, carbonates, and phosphate triesters. See Brown, 1994 *Meth. Mol. Biol.* vol. 20:1-8; Sonveaux, 1994. *Meth. Mol. Biol.* Vol. 26:1-72; and Uhlmann et al., 1990. *Chem. Rev.* vol. 90:543-583. Salts, esters, and other pharmaceutically acceptable forms of such compounds are also encompassed.

In a preferred embodiment, a compound can be a peptide, polypeptide, polypeptide analog, amino acid, or amino acid analog. Such a compound can be synthesized manually or by an automated synthesizer. Any peptide, polypeptide, polypeptide analog, amino acid, or amino acid analog can be involved in UTR-dependent modulation of gene expression mediated by a GEM. Compounds detected by an assay of the present invention can modulate interactions of a GEM including of a UTR-complex containing a protein or a ribonucleoprotein. Such a compound can increase or decrease the interaction of a GEM and protein or protein complex.

A compound can be a member of a library of compounds. In a specific embodiment, the compound is selected from a combinatorial library of compounds comprising peptoids; random biooligomers; diversomers such as hydantoins, benzodiazepines and dipeptides; vinylogous polypeptides; non-peptidal peptidomimetics; oligocarbamates; peptidyl phosphonates; peptide nucleic acid libraries; antibody libraries; carbohydrate libraries; and small organic molecule libraries. In a preferred embodiment, the small organic molecule libraries are libraries of benzodiazepines, isoprenoids, thiazolidinones, metathiazanones, pyrrolidines, morpholino compounds, or diazepindiones.

In another embodiment, a compound can have a molecular weight less than about 10,000 grams per mole, less than about 5,000 grams per mole, less than about 1,000 grams per mole, less than about 500 grams per mole, less than about 100 grams per mole, and salts, esters, and other pharmaceutically acceptable forms of such compounds.

Compounds can be evaluated comprehensively for cytotoxicity. The cytotoxic effects of the compounds can be studied using cell lines, including for example 293T (kidney), HuH7 (liver), and Hela cells over about 4, 10, 16, 24, 36 or 72-hour periods. In addition, a number of primary cells such as normal fibroblasts and peripheral blood mononuclear cells (PBMCs) can be grown in the presence of compounds at various concentrations for about 4 days. Fresh compound can be added every other day to maintain a constant level of exposure with time. The effect of each compound on cell-proliferation can be determined by CellTiter 96® AQueous One Solution Cell Proliferation Assay (Promega Co, Madison, Wis.) and [$^3$H]-thymidine incorporation. Treatment of some cells with some of the compounds may have cytostatic effects. A selective index (ratios of $CC_{50}$ in cytotoxicity assays to the $EC_{50}$ in ELISA or FACS or the reporter gene assays) for each compound can be calculated for all of the UTR-reporters and protein inhibition assays. Compounds exhibiting substantial selective indices can be of interest and can be analyzed further in the functional assays.

The structure of a compound can be determined by any well-known method such as mass spectroscopy, NMR, vibrational spectroscopy, or X-ray crystallography as part of a method of the present invention.

Compounds can be pharmacologic agents already known in the art or can be compounds previously unknown to have any pharmacological activity. The compounds can be naturally occurring or designed in the laboratory. They can be isolated from microorganisms, animals, or plants, and can be produced recombinantly, or synthesized by chemical methods known in the art. If desired, compounds can be obtained using any of the numerous combinatorial library methods known in the art, including but not limited to, biological libraries, spatially addressable parallel solid phase or solution phase libraries, synthetic library methods requiring deconvolution, the "one-bead one-compound" library method, and synthetic library methods using affinity chromatography selection. Methods for the synthesis of molecular libraries are well known in the art (see, for example, DeWitt et al., Proc. Natl. Acad. Sci. U.S.A. 90, 6909, 1993; Erb et al. Proc. Natl. Acad. Sci. U.S.A. 91, 11422, 1994; Zuckermann et al., J. Med. Chem. 37, 2678, 1994; Cho et al., Science 261, 1303, 1993; Carell et al., Angew. Chem. Int. Ed. Engl. 33, 2059, 1994; Carell et al., Angew. Chem. Int. Ed. Engl. 33, 2061; Gallop et al., J. Med. Chem. 37, 1233, 1994). Libraries of compounds can be presented in solution (see, e.g., Houghten, BioTechniques 13, 412-421, 1992), or on beads (Lam, Nature 354, 82-84, 1991), chips (Fodor, Nature 364, 555-556, 1993), bacteria or spores (Ladner, U.S. Pat. No. 5,223,409), plasmids (Cull et al., Proc. Natl. Acad. Sci. U.S.A. 89, 1865-1869, 1992), or phage (Scott & Smith, Science 249, 386-390, 1990; Devlin, Science 249, 404-406, 1990); Cwirla et al., Proc. Natl. Acad. Sci. 97, 6378-6382, 1990; Felici, J. Mol. Biol. 222, 301-310, 1991; and Ladner, U.S. Pat. No. 5,223,409).

Methods of the present invention for screening compounds can select for compounds capable of modulating gene expression, which are capable of directly binding to a ribonucleic acid molecule transcribed from a target gene. In a preferred embodiment, a compound identified in accordance with the methods of the present invention may be capable of binding to one or more trans-acting factors (such as, but not limited to, proteins) that modulate UTR-dependent expression of a target gene. In another preferred embodiment, a compound identified in accordance with the methods of invention may disrupt an interaction between the 5' UTR and the 3' UTR.

Compounds can be tested using in vitro assays (e.g., cell-free assays) or in vivo assays (e.g., cell-based assays) well known to one of skill in the art or as provided in the present invention. A compound that modulates expression of a target gene can be determined from the methods provided in the present invention. A UTR of the present invention includes UTRs capable of modulating gene expression in the presence, in the absence, or in the presence and absence of a compound. In a preferred embodiment, the effect of a compound on the expression of one or more genes can be determined utilizing assays well known to one of skill in the art or provided by the present invention to assess the specificity of a particular compound's effect on the UTR-dependent expression of a target gene. In a more preferred embodiment, a compound has specificity for a plurality of genes. In another more preferred embodiment, a compound identified utilizing the methods of the present invention is capable of specifically effect the expression of only one gene or, alternatively, a group of genes within the same signaling pathway. Compounds identified in the assays of the present invention can be tested for biological activity using host cells containing or engineered to contain the target RNA element involved in UTR-dependent gene expression coupled to a functional readout system.

Screening Assays

The present invention includes and provides for assays capable of screening for compounds capable of modulating gene expression. In a preferred aspect of the present invention, an assay is an in vitro assay. In another aspect of the present invention, an assay is an in vivo assay. In another preferred aspect of the present invention, an assay measures translation. In a preferred aspect of the present invention, the assay includes a nucleic acid molecule of the present invention or a construct of the present invention. A nucleic acid molecule or construct of the present invention includes, without limitation, a GEM, or a sequence that differs from any of the residues in a GEM in that the nucleic acid sequence has been deleted, substituted, or added in a manner that does not alter the function. The present invention also provides fragments and complements of all the nucleic acid molecules of the present invention.

In one aspect of a preferred, present invention, the activity or expression of a reporter gene is modulated. Modulated means increased or decreased expression during any point before, after, or during translation. In a preferred embodiment, activity or expression of a reporter gene is modulated during translation. For example, inhibition of translation of the reporter gene can modulate expression. In an alternative example, the expression level of a reporter gene is modulated if the steady-state level of the expressed protein decreased even though translation was not inhibited. As a further example, a change in the half-life of a mRNA can modulate expression.

In an alternative embodiment, modulated activity or expression of a reporter gene means increased or decreased expression during any point before, during, or after translation.

In a more preferred aspect, the activity or expression of a reporter gene or a target gene is modulated by greater than 30%, 40%, 50%, 60%, 70%, 80% or 90% in the presence of a compound. In a highly preferred aspect, more of an effect is observed in cancer cells.

Expression of a reporter gene can be detected with, for example, techniques known in the art. Translation of a reporter gene can be detected in vitro or in vivo. In detection assays, either the compound or the reporter gene can comprise a detectable label, such as a fluorescent, radioisotopic or chemiluminescent label or an enzymatic label, such as horseradish peroxidase, alkaline phosphatase, or luciferase.

Using an assay of the present invention, a compound that affects a UTR or multiple UTRs from one target gene can be determined. In a preferred embodiment, a compound that affects the 5' UTR, 3' UTR, or the 5' and 3' UTRs from a single target gene can be detected. In another preferred embodiment, the 5' and 3' UTRs from multiple target genes are each reacted with multiple compounds, and an effect of a compound on a UTR can be detected.

In an assay of the present invention, the result of one or more UTRs being affected by a compound is qualitatively, quantitatively, or qualitatively and quantitatively determined based on the modulation of expression from a reporter gene operatively linked to the UTRs. The modulation of expression from a reporter gene operatively linked to the UTR can be relative to the expression from a reporter gene operatively linked to the UTR in the absence of the compound, in comparison to a different dosage of the same compound, in comparison to another compound, in comparison to the reaction of another UTR/compound effect, or by combining the results of these comparisons.

A compound can be reacted with one or multiple UTRs operatively linked to a reporter gene. If the compound modulates the expression of a reporter gene operatively linked to a UTR, the compound can be determined to be specifically active, nonspecifically active, or inactive with respect to the one or more UTRs being tested. The compound is specifically active if it modulates the expression of a reporter gene operatively linked to some UTRs, but not all UTRs, being tested. The compound is nonspecifically active if it similarly modulates the expression of a reporter gene operatively linked to all of the UTRs being tested. Whether the compound similarly modulates the expression of a reporter gene operatively linked to more than one UTR can be determined statistically. Similar modulation occurs when the effect of the compound modulates the reporter gene expression within an order of magnitude for the UTRs tested. The compound is inactive if it does not modulate the expression from a reporter gene operatively linked to any of the UTRs tested.

One or more UTRs can be tested with one or more compounds. In a preferred embodiment, there can be any number of UTRs tested, for example without limitation, one, ten, hundreds, thousands, tens of thousands, or hundreds of thousands of UTRs or UTR pairs, where UTR pairs refers to a 5' UTR and a 3' UTR from the same target gene. In a preferred embodiment, a single pair of UTRs is reacted with about 2,000—about 5,000 compounds. In a more preferred embodiment, each UTR reacts with each compound at about 3—about 7 concentrations, for example, without limitation, using a 4-point 10-fold dose-response.

Compounds of the present invention can be categorized based on their effect on UTRs from target genes. In a preferred embodiment, compounds can be categorized based on their ability to modulate the expression from a reporter gene operatively linked to a UTR. Categories of compounds can include, for example without limitation, compounds that modulate greater than or equal to 50% of the UTRs tested, compounds that modulate less than 50% modulation of the UTRs tested, compounds that modulate at least one UTR from a target gene at any concentration, compounds that modulate greater than or equal to 25% of the UTRs tested, compounds where the difference in modulation of at least one target UTR is greater than or equal to 25% of any other target UTR at any concentration tested, compounds where the difference in modulation of at least one target UTR is greater than or equal to 25% of any other UTR target for at least one concentration tested, and compounds with oddly-shaped dose-response curves for at least one target UTR tested. Compounds of the present invention can alternatively be classified based on the concentration where the compound is capable of modulating the expression from a reporter gene operatively linked to at least one target UTR.

In a preferred embodiment, most compounds lack UTR selectivity and similarly modulate the expression from a reporter gene operatively linked to at least one target UTR. In a more preferred embodiment, most compounds lack UTR selectivity and similarly modulate the expression from a reporter gene operatively linked to at least one target UTR from at least four different target genes. In a most preferred embodiment, about 10—about 50 compounds out of about 5,000 randomly chosen compounds will have pairwise $IC_{50}$ ratios of 4-fold or more across at least four different target genes.

In a most preferred aspect, the activity or expression of a reporter gene is modulated without altering the activity of a control gene for general, indiscriminate translation activity. As used herein, indiscriminate translation activity refers to modulation in translation levels or activity that is random or unsystematic. One assay for modulation in general, indiscriminate translation activity uses a general translational inhibitor, for example puromycin, which is an inhibitor that causes release of nascent peptide and mRNA from actively translating ribosomes.

High-throughput screening can be done by exposing nucleic acid molecules of the present invention to a library of compounds and detecting gene expression with assays known in the art, including, for example without limitation, those described above. In one embodiment of the present invention, cancer cells, such as MCF-7 cells, expressing a nucleic acid molecule of the present invention are treated with a library of compounds. Percent inhibition of reporter gene activity can be obtained for all of the library compounds and can be analyzed using, for example without limitation, a scattergram generated by SpotFire® (SpotFire, Inc., Somerville, Mass.). The high-throughput screen can be followed by subsequent selectivity screens. In a preferred embodiment, a subsequent selectivity screen can include detection of reporter gene expression in cells expressing, for example, a reporter gene linked to a GEM or flanked by a 5' and 3' UTR of the same gene, either of which can contain a GEM of the present invention. In an alternative preferred embodiment, a subsequent selectivity screen can include detection of reporter gene expression in cells in the presence of a various concentrations of compounds.

Once a compound has been identified to modulate UTR-dependent expression of a target gene and preferably, the structure of the compound has been identified by the methods described in the present invention and well known in the art, the compounds are tested for biological activity in further assays and/or animal models. Further, a lead compound may be used to design congeners or analogs.

A wide variety of labels and conjugation techniques are known by those skilled in the art and can be used in various nucleic acid and amino acid assays. Methods for producing labeled hybridization or PCR probes for detecting sequences related to GEMs of the present invention include oligolabeling, nick translation, end-labeling, or PCR amplification using a labeled nucleotide. Suitable reporter molecules or labels which can be used for ease of detection include radionuclides, enzymes, and fluorescent, chemiluminescent, or chromogenic agents, as well as substrates, cofactors, inhibitors, magnetic particles, and the like.

In Vitro

The present invention includes and provides for assays capable of screening for compounds capable of modulating gene expression. In a preferred aspect of the present invention, an assay is an in vitro assay. In a preferred aspect of the present invention, an in vitro assay that measures translation. In a preferred aspect of the present invention the in vitro assay includes a nucleic acid molecule of the present invention or a construct of the present invention.

In one embodiment, a reporter gene of the present invention can encode a fusion protein or a fusion protein comprising a domain that allows the expressed reporter gene to be bound to a solid support. For example, glutathione-S-transferase fusion proteins can be adsorbed onto glutathione sepharose beads (Sigma Chemical, St. Louis, Mo.) or glutathione derivatized microtiter plates, which are then combined with the compound or the compound and the non-adsorbed expressed reporter gene; the mixture is then incubated under conditions conducive to complex formation (e.g., at physiological conditions for salt and pH). Following incubation, the beads or microtiter plate wells are washed to remove any unbound components. Binding of the interactants can be determined either directly or indirectly, as described above. Alternatively, the complexes can be dissociated from the solid support before binding is determined.

Other techniques for immobilizing an expressed reporter gene or compound on a solid support also can be used in the screening assays of the invention. For example, either an expressed reporter gene or compound can be immobilized utilizing conjugation of biotin and streptavidin. Biotinylated expressed reporter genes or compounds can be prepared from biotin-NHS(N-hydroxysuccinimide) using techniques well known in the art (e.g., biotinylation kit, Pierce Chemicals, Rockford, Ill.) and immobilized in the wells of streptavidin-coated 96 well plates (Pierce Chemicals, Rockford, Ill.). Alternatively, antibodies which specifically bind to an expressed reporter gene or compound, but which do not interfere with a desired binding or catalytic site, can be derivatized to the wells of the plate. Unbound target or protein can be trapped in the wells by antibody conjugation.

Methods for detecting such complexes, in addition to those described above for the GST-immobilized complexes, include immunodetection of complexes using antibodies which specifically bind to an expressed reporter gene or compound, enzyme-linked assays which rely on detecting an activity of an expressed reporter gene, electrophoretic mobility shift assays (EMSA), and SDS gel electrophoresis under reducing or non-reducing conditions.

In one embodiment, translation of a reporter gene in vitro can be detected following the use of a reticulocyte lysate translation system, for example the TNT® Coupled Reticulocyte Lysate System (Promega Co., Madison, Wis.). In this aspect, for example, without limitation, RNA (100 ng) can be translated at 30° C. in reaction mixtures containing 70% reticulocyte lysate, 20 µM amino acids and RNase inhibitor (0.8 units/µl). After 45 minutes of incubation, 20 µl of Luclite can be added and luminescence can be read on the View-Lux. Different concentrations of compounds can be added to the reaction in a final DMSO concentration of 2% and the $EC_{50}$ values calculated. Puromycin can be used as control for general indiscriminate translation inhibition. In vitro transcripts encoding a reporter gene linked to specific UTRs from target genes, including GAPDH, XIAP, TNF-α, and HIF-1α, can also be used.

To study the influence of cell-type specific factors, capped RNA can be translated in translation extracts prepared from specialized cells or cancer cell lines, for example without limitation, HT1080 cells (a human fibrosarcoma cell line). Briefly, the cells can be washed with PBS and swollen in hypotonic buffer (10 mM Hepes, pH 7.4, 15 mM KCl, 1.5 mM $Mg(OAc)_2$, 2 mM DTT and 0.5 mM Pefabloc (Pentapharm Ltd. Co., Switzerland) for 5 minutes on ice. The cells can be lysed using a Dounce homogenizer (100 strokes), and the extracts can be spun for 10 minutes at 10,000×g. These clarified extracts can then be flash-frozen in liquid nitrogen and stored in aliquots at −70° C. The translation reaction can be capped RNA (50 ng) in a reaction mixture containing 60% clarified translation extract, 15 µM total amino acids, 0.2 mg/ml Creatine phospho-kinase, which are all in 1× translation buffer (15 mM Hepes, pH 7.4, 85 mM KOAc, 1.5 mM Mg(OAc)$_2$, 0.5 mM ATP, 0.075 mM GTP, 18 mM creatine diphosphate and 1.5 mM DTT). After incubation of the translation reaction for 90 min at 37° C., activity of the protein encoded by the reporter gene can be detected. For activity of luciferase, encoded by the luciferase gene serving as the reporter gene, addition of 20 μl of LucLite® (Packard Instrument Co., Inc., Meriden, Conn.) can be used. Capped and uncapped RNAs can be synthesized in vitro using the T7 polymerase transcription kits (Ambion Inc., Austin, Tex.) and can be used in a similar in vitro system to study the influence of cell-type specific factors on translation.

In Vivo

The present invention includes and provides for assays capable of screening for compounds capable of modulating gene expression. In a preferred aspect of the present invention, an assay is an in vivo assay. One preferred aspect of the present invention is an assay that measures translation. In a preferred embodiment of the present invention, an in vivo assay includes a nucleic acid molecule of the present invention or a construct of the present invention and can include the use of a cell or a cell or tissue within an organism. In a more preferred embodiment, an in vivo assay includes a nucleic acid molecule of the present invention present in a cell or a cell or tissue within an organism.

In another embodiment, in vivo translation of a reporter gene can be detected. In a preferred embodiment, a reporter gene is transfected into a cancer cell obtained from a cell line available at the (American Type Culture Collection (ATCC), Manassas, Va.), for example HeLa, MCF-7, and COS-7, BT474. In a more preferred embodiment, a cancer cell has an altered genome relative to a similarly derived normal, primary cell, and the mammalian cancer cell proliferates under conditions where such a primary cell would not.

Screening for compounds that modulate reporter gene expression can be carried out in an intact cell. Any cell that comprises a reporter gene can be used in a cell-based assay system. A reporter gene can be naturally occurring in the cell or can be introduced using techniques such as those described above (see Cells and Organisms). In one embodiment, a cell line is chosen based on its expression levels of a naturally occurring protein, for example without limitation, VEGF, Her2, or survivin. Modulation of reporter gene expression by a compound can be determined in vitro as described above or in vivo as described below.

To detect expression of endogenous or heterologous proteins, a variety of protocols for detecting and measuring the expression of a reporter gene are known in the art. For example, Enzyme-Linked Immunosorbent Assays (ELISAs), western blots using either polyclonal or monoclonal antibodies specific for an expressed reporter gene, Fluorescence-Activated Cell Sorter (FACS), electrophoretic mobility shift assays (EMSA), or radioimmunoassay (RIA) can be performed to quantify the level of specific proteins in lysates or media derived from cells treated with the compounds. In a preferred embodiment, a phenotypic or physiological readout can be used to assess UTR-dependent activity of the target RNA in the presence and absence of the lead compound.

A wide variety of labels and conjugation techniques are known by those skilled in the art and can be used in various nucleic acid and amino acid assays. Methods for producing labeled hybridization or PCR probes for detecting sequences related to polynucleotides having a GEM of the present invention include oligolabeling, nick translation, end-labeling, or PCR amplification using a labeled nucleotide. Alternatively, sequences having a GEM of the present invention can be cloned into a vector for the production of a mRNA probe. Such vectors are known in the art, are commercially available, and can be used to synthesize RNA probes in vitro by addition of labeled nucleotides and an appropriate RNA polymerase such as T7, T3, or SP6. These procedures can be conducted using a variety of commercially available kits (Amersham Biosciences Inc., Piscataway, N.J.; and Promega Co, Madison, Wis.). Suitable reporter molecules or labels which can be used for ease of detection include radionucleotides, enzymes, and fluorescent, chemiluminescent, or chromogenic agents, as well as substrates, cofactors, inhibitors, magnetic particles, and the like.

Therapeutic Uses

The present invention also provides for methods for treating, preventing or ameliorating one or more symptoms of a disease or disorder associated with the aberrant expression of a target gene, said method comprising administering to a subject in need thereof a therapeutically or prophylactically effective amount of a compound, or a pharmaceutically acceptable salt thereof, identified according to the methods described herein. In one embodiment, the target gene is aberrantly overexpressed. In another embodiment, the target gene is expressed at an aberrantly low level. In particular, the invention provides for a method of treating or preventing a disease or disorder or ameliorating a symptom thereof, said method comprising administering to a subject in need thereof an effective amount of a compound, or a pharmaceutically acceptable salt thereof, identified according to the methods described herein, wherein said effective amount increases the expression of a target gene beneficial in the treatment or prevention of said disease or disorder. The invention also provides for a method of treating or preventing a disease or disorder or ameliorating a symptom thereof, said method comprising administering to a subject in need thereof an effective amount of a compound, or a pharmaceutically acceptable salt thereof, identified according to the methods described herein, wherein said effective amount decreases the expression of a target gene whose expression is associated with or has been linked to the onset, development, progression or severity of said disease or disorder. In a specific embodiment, the disease or disorder is a proliferative disorder, an inflammatory disorder, an infectious disease, a genetic disorder, an autoimmune disorder, a cardiovascular disease, or a central nervous system disorder. In an embodiment wherein the disease or disorder is an infectious disease, the infectious disease can be caused by a fungal infection, a bacterial infection, a viral infection, or an infection caused by another type of pathogen.

In addition, the present invention also provides pharmaceutical compositions that can be administered to a patient to achieve a therapeutic effect. Pharmaceutical compositions of the invention can comprise, for example, ribozymes or antisense oligonucleotides, antibodies that specifically bind to a GEM of the present invention, or mimetics, activators, inhibitors of GEM activity, or a nucleic acid molecule of the present invention. The compositions can be administered alone or in combination with at least one other agent, such as stabilizing compound, which can be administered in any sterile, biocompatible pharmaceutical carrier, including, but not limited to, saline, buffered saline, dextrose, and water. The compositions can be administered to a patient alone, or in combination with other agents, drugs or hormones.

In addition to the active ingredients, these pharmaceutical compositions can contain suitable pharmaceutically-acceptable carriers comprising excipients and auxiliaries which facilitate processing of the active compounds into preparations which can be used pharmaceutically. Pharmaceutical compositions of the invention can be administered by any number of routes including, but not limited to, oral, intravenous, intramuscular, intra-arterial, intramedullary, intrathecal, intraventricular, transdermal, subcutaneous, intraperitoneal, intranasal, parenteral, topical, sublingual, or rectal means. Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethylcellulose; gums including arabic and tragacanth; and proteins such as gelatin and collagen. If desired, disintegrating or solubilizing agents can be added, such as the cross-linked polyvinyl pyrrolidone, agar, alginic acid, or a salt thereof, such as sodium alginate.

Pharmaceutical preparations that can be used orally include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds can be dissolved or suspended in suitable liquids, such as fatty oils, liquid, or liquid polyethylene glycol with or without stabilizers.

Pharmaceutical formulations suitable for parenteral administration can be formulated in aqueous solutions, preferably in physiologically compatible buffers such as Hanks' solution, Ringer's solution, or physiologically buffered saline. Aqueous injection suspensions can contain substances that increase the viscosity of the suspension, such as sodium carboxymethyl cellulose, sorbitol, or dextran. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers also can be used for delivery. Optionally, the suspension also can contain suitable stabilizers or agents that increase the solubility of the compounds to allow for the preparation of highly concentrated solutions. For topical or nasal administration, penetrants appropriate to the particular barrier to be permeated are used in the formulation. Such penetrants are generally known in the art.

The pharmaceutical compositions of the present invention can be manufactured in a manner that is known in the art, e.g., by methods of conventional mixing, dissolving, granulating, dragee-making, levigating, emulsifying, encapsulating, entrapping, or lyophilizing processes. The pharmaceutical composition can be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation can be a lyophilized powder which can contain any or all of the following: 1-50 mM histidine, 0.1%-2% sucrose, and 2-7% mannitol, at a pH range of 4.5 to 5.5, that is combined with buffer prior to use. Further details on techniques for formulation and administration can be found in the latest edition of *Remington's Pharmaceutical Sciences* (Maack Publishing Co., Easton, Pa.). After pharmaceutical compositions have been prepared, they can be placed in an appropriate container and labeled for treatment of an indicated condition. Such labeling would include amount, frequency, and method of administration.

Determination of a Therapeutically Effective Dose

A therapeutically effective dose refers to that amount of active ingredient that increases or decreases reporter gene activity relative to reporter gene activity that occurs in the absence of the therapeutically effective dose. For any compound, the therapeutically effective dose can be estimated initially either in cell culture assays or in animal models, usually mice, rabbits, dog, or pigs. The animal model also can be used to determine the appropriate concentration range and route of administration. Such information can then be used to determine useful doses and routes for administration in humans.

Therapeutic efficacy and toxicity, e.g., $ED_{50}$ (the dose therapeutically effective in 50% of the population) and $LD_{50}$ (the dose lethal to 50% of the population), can be determined by standard pharmaceutical procedures in cell cultures or experimental animals. The dose ratio of toxic to therapeutic effects is the therapeutic index, and it can be expressed as the ratio, $LD_{50}/ED_{50}$.

Pharmaceutical compositions that exhibit large therapeutic indices are preferred. The data obtained from cell culture assays and animal studies is used in formulating a range of dosage for human use. The dosage contained in such compositions is preferably within a range of circulating concentrations that include the $ED_{50}$ with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active ingredient or to maintain the desired effect. Factors that can be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions can be administered every 3 to 4 days, every week, or once every two weeks depending on the half-life and clearance rate of the particular formulation.

Normal dosage amounts can vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides.will be specific to particular cells, conditions, locations, etc.

If the reagent is a single-chain antibody, polynucleotides encoding the antibody can be constructed and introduced into a cell either ex vivo or in vivo using well-established techniques including, but not limited to, transferrin-polycation-mediated DNA transfer, transfection with naked or encapsulated nucleic acids, liposome-mediated cellular fusion, intracellular transportation of DNA-coated latex beads, protoplast fusion, viral infection, electroporation, "gene gun," and DEAE- or calcium phosphate-mediated transfection.

Effective in vivo dosages of an antibody are in the range of about 5 µg to about 50 µg/kg, about 50 µg to about 5 mg/kg, about 100 µg to about 500 µg/kg of patient body weight, and about 200 to about 250 µg/kg of patient body weight. For administration of polynucleotides encoding single-chain antibodies, effective in vivo dosages are in the range of about 100 ng to about 200 ng, 500 ng to about 50 mg, about 1 µg to about 2 mg, about 5 µg to about 500 µg, and about 20 µg to about 100 µg of DNA.

If the expression product is mRNA, the reagent is preferably an antisense oligonucleotide or a ribozyme. Polynucleotides that express antisense oligonucleotides or ribozymes can be introduced into cells by a variety of methods, as described above.

Preferably, a reagent reduces expression of a reporter gene or the activity of a reporter gene by at least about 10, preferably about 50, more preferably about 75, 90, or 100% relative to the absence of the reagent. Alternatively, a reagent increases expression of a reporter gene or the activity of a reporter gene by at least about 10, preferably about 50, more preferably about 75, 90, or 100% relative to the absence of the reagent. The effectiveness of the reagent or mechanism chosen to modulate the level of expression of a reporter gene or the activity of a reporter gene can be assessed using methods well known in the art, such as hybridization of nucleotide probes to reporter gene-specific mRNA, quantitative RT-PCR, immunologic detection of an expressed reporter gene, or measurement of activity from an expressed reporter gene.

In any of the embodiments described above, any of the pharmaceutical compositions of the invention can be administered in combination with other appropriate therapeutic agents. Selection of the appropriate agents for use in combination therapy can be made by one of ordinary skill in the art, according to conventional pharmaceutical principles. The combination of therapeutic agents can act synergistically to effect the treatment or prevention of the various disorders described above. Using this approach, one may be able to achieve therapeutic efficacy with lower dosages of each agent, thus reducing the potential for adverse side effects.

Any of the therapeutic methods described above can be applied to any subject in need of such therapy, including, for example, mammals such as dogs, cats, cows, horses, rabbits, monkeys, and most preferably, humans.

Administration of a Therapeutically Effective Dose

A reagent which affects translation, either in vitro or in vivo, can be administered to a human cell to specifically reduce translational activity of a specific gene. In a preferred embodiment, the reagent preferably binds to a 5' UTR of a gene. In an alternate embodiment, the present invention the reagent preferably binds to a GEM of the present invention. In a preferred embodiment, the reagent is a compound. For treatment of human cells ex vivo, an antibody can be added to a preparation of stem cells which have been removed from the body. The cells can then be replaced in the same or another human body, with or without clonal propagation, as is known in the art.

In one embodiment, the reagent is delivered using a liposome. Preferably, the liposome is stable in the animal into which it has been administered for at least about 30 minutes, more preferably for at least about 1 hour, and even more preferably for at least about 24 hours. A liposome comprises a lipid composition that is capable of targeting a reagent, particularly a polynucleotide, to a particular site in an animal, such as a human. Preferably, the lipid composition of the liposome is capable of targeting to a specific organ of an animal, such as the lung, liver, spleen, heart brain, lymph nodes, and skin.

A liposome useful in the present invention comprises a lipid composition that is capable of fusing with the plasma membrane of the targeted cell to deliver its contents to the cell. Preferably, the transfection efficiency of a liposome is about 0.5 µg of DNA per 16 µmole of liposome delivered to about $10^6$ cells, more preferably about 1.0 µg of DNA per 16 µmole of liposome delivered to about $10^6$ cells, and even more preferably about 2.0 µg of DNA per 16 nmol of liposome delivered to about $10^6$ cells. Preferably, a liposome is between about 100 and 500 nm, more preferably between about 150 and 450 nm, and even more preferably between about 200 and 400 nm in diameter.

Suitable liposomes for use in the present invention include those liposomes standardly used in, for example, gene delivery methods known to those of skill in the art. More preferred liposomes include liposomes having a polycationic lipid composition and/or liposomes having a cholesterol backbone conjugated to polyethylene glycol. Optionally, a liposome comprises a compound capable of targeting the liposome to a particular cell type, such as a cell-specific ligand exposed on the outer surface of the liposome.

Complexing a liposome with a reagent such as an antisense oligonucleotide or ribozyme can be achieved using methods that are standard in the art (see, for example, U.S. Pat. No. 5,705,151). Preferably, from about 0.1 µg to about 10 µg of polynucleotide is combined with about 8 nmol of liposomes, more preferably from about 0.5 µg to about 5 µg of polynucleotides are combined with about 8 nmol liposomes, and even more preferably about 1.0 µg of polynucleotides is combined with about 8 nmol liposomes.

In another embodiment, antibodies can be delivered to specific tissues in vivo using receptor-mediated targeted delivery. Receptor-mediated DNA delivery techniques are taught in, for example, Findeis et al. Trends in Biotechnol. 11, 202-05 (1993); Chiou et al., *Gene Therapeutics: Methods And Applications Of Direct Gene Transfer* (J. A. Wolff, ed.) (1994); Wu & Wu, J. Biol. Chem. 263, 621-24 (1988); Wu et al., J. Biol. Chem. 269, 542-46 (1994); Zenke et al., Proc. Natl. Acad. Sci. U.S.A. 87, 3655-59 (1990); Wu et al., J. Biol. Chem. 266, 338-42 (1991).

Diagnostic Methods

Agents of the present invention can also be used in diagnostic assays for detecting diseases and abnormalities or susceptibility to diseases and abnormalities related to the presence of mutations in the nucleic acid sequences that encode a GEM of the present invention. For example, differences can be determined between the cDNA or genomic sequence encoding a GEM in individuals afflicted with a disease and in normal individuals. If a mutation is observed in some or all of the afflicted individuals but not in normal individuals, then the mutation is likely to be the causative agent of the disease.

For example, the direct DNA sequencing method can reveal sequence differences between a reference gene and a gene having mutations. In addition, cloned DNA segments can be employed as probes to detect specific DNA segments. The sensitivity of this method is greatly enhanced when combined with PCR. For example, a sequencing primer can be used with a double-stranded PCR product or a single-stranded template molecule generated by a modified PCR. The sequence determination is performed by conventional procedures using radiolabeled nucleotides or by automatic sequencing procedures using fluorescent tags.

Moreover, for example, genetic testing based on DNA sequence differences can be carried out by detection of alteration in electrophoretic mobility of DNA fragments in gels with or without denaturing agents. Small sequence deletions and insertions can be visualized, for example, by high-resolution gel electrophoresis. DNA fragments of different sequences can be distinguished on denaturing formamide gradient gels in which the mobilities of different DNA fragments are retarded in the gel at different positions according to their specific melting or partial melting temperatures (see, e.g., Myers et al., Science 230, 1242, 1985). Sequence changes at specific locations can also be revealed by nuclease protection assays, such as RNase and S1 protection or the chemical cleavage method (e.g., Cotton et al., Proc. Natl. Acad. Sci. USA 85, 4397-4401, 1985). Thus, the detection of a specific DNA sequence can be performed by methods such as hybridization, RNase protection, chemical cleavage, direct DNA sequencing or the use of restriction enzymes and Southern blotting of genomic DNA. In addition to direct methods such as gel-electrophoresis and DNA sequencing, mutations can also be detected by in situ analysis.

Altered levels of a GEM of the present invention can also be detected in various tissues. For example, one or more genes having a GEM can be detected by assays used to detect levels of particular nucleic acid sequence, such as Southern hybridization, northern hybridization, and PCR. Alternatively, assays can be used to detect levels of a reporter polypeptide regulated by a GEM or of a polypeptide encoded by a gene having a GEM. Such assays are well known to those of skill in the art and include radioimmunoassays, competitive binding assays, western blot analysis, and ELISA assays. A sample from a subject, such as blood or a tissue biopsy derived from a host, may be the material on which these assays are conducted.

Having now generally described the invention, the same will be more readily understood through reference to the following examples that are provided by way of illustration, and are not intended to be limiting of the present invention, unless specified.

Each periodical, patent, and other document or reference cited herein is herein incorporated by reference in its entirety.

EXAMPLES

Example 1

Identification of Compounds that Specifically Inhibit Reporter Gene Expression Post-Transcriptionally A monocistronic reporter construct (pLuc/vegf5'+3'UTR) is under the transcriptional control of the CMV promoter and contains the VEGF 5' UTR driving the luciferase reporter upstream of the VEGF 3'UTR. Stable cell lines are generated by transfecting 293 cells with the pLuc/vegf5'+3'UTR construct. A stable cell line is cultured under hygromycin B selection to create clonal cell lines consistent with protocols well known in the art. After two weeks of selection, clonal cell lines are screened for luciferase activity. The luciferase activity of several clonal cell lines (hereafter "Clones") are compared and normalized against total protein content. Clones are maintained under hygromycin B selection for more than three months with intermittent monitoring of luciferase activity. Clones are stable and maintain a high level of luciferase expression. Many Clones, for example, about twenty, may be compared to each other with respect to luciferase activity. In comparison to Clones B9, D3, and H6, clone B9 exhibits the highest level of luciferase activity. In addition, semi-quantitative PCR analysis is performed, and the results indicate that multiple copies of the reporter are integrated per cell. Particular parameters for Clones are studied prior to selection for use in post-transcriptional, high-throughput screening (HTS). Relevant parameters for HTS include, but are not limited to, cell number, incubation time, DMSO concentration, and volume of substrate.

Chemical libraries in excess of 150,000 compounds are screened by HTS with a Clone containing the monocistronic reporter construct, pLuc/vegf5'+3'UTR. Screens are performed in duplicate with each molecule at a single concentration of about 7.5 µM. Bright-Glow (Promega Co., Madison, Wis.) is used as a substrate to measure firefly luciferase activity. Active compounds are identified by reporting the average percent inhibition of the duplicate compounds followed by rejecting those compounds that did not provide satisfactory reproducibility. The average percent inhibition of compounds that provide satisfactory reproducibility is within a range of about 10%, about 25% or about 35% in the duplicate compounds. Data is analyzed as a normal distribution, which is apparent from graphical and statistical analysis of skewness and kurtosis. Hits are then reported at about a 99% confidence level, usually representing a selection of 3 standard deviations from the mean, or a hit lower limit of observed inhibition about equal to 50%. These selection criteria result in a hit rate of about 1%.

Certain compounds that are identified through the HTS-screening tier by screening with clone B9 modulate hypoxia-inducible endogenous VEGF expression. Endogenous VEGF protein levels are monitored by an ELISA assay (R&D Systems, Minneapolis, Minn.). HeLa cells are used to evaluate hypoxia-inducible expression. HeLa cells demonstrate about a three- to five-fold hypoxia-inducible window as compared to normoxic conditions (about 1000—about 1500 pg/ml under hypoxia compared to about 200—about 400 pg/ml under normoxia). Cells are cultured overnight to 48 hrs under hypoxic conditions (about 1% 02, about 5% $CO_2$, and balanced with nitrogen) in the presence or absence of compounds. The conditioned media is assayed by ELISA. The concentration of VEGF is calculated from the standard ELISA curve of each assay. The assays are performed in duplicate at a compound concentration of about 7.5 µM. A threshold of about 50% inhibition for a compound is selected as a criterion for further investigation. Further evaluation of about 100 to about 150 compounds is conducted from about 700 to about 800 initial HTS hits. The activity of the identified compounds is confirmed by repeating the experiments described above. The identified compounds are then acquired as dry powders and analyzed further. The purity and molecular weight of the identified compounds are confirmed by LC-MS.

A dose-response analysis is performed using the ELISA assay and conditions described above. The conditions for the dose-response ELISA are analogous to those described above. A series of seven different serially-diluted concentrations are analyzed. In parallel, a dose-response cytotoxicity assay is performed under the same conditions as the ELISA to ensure that the inhibition of VEGF expression is not due to cytotoxicity. Dose-response curves are plotted using percentage inhibition versus log of concentration of the compound.

For each compound, the maximal inhibition is set as 100% and the minimal inhibition is set as 0% to generate $EC_{50}$ and $CC_{50}$ values. An identified compound from HTS shows a sigmoidal curve over a compound concentration range from about $10^{-1}$ µM to about $10^4$ µM when plotted as the log of concentration against the percent inhibition of VEGF expression on the y-axis. The same identified compound from HTS shows a convex curve over the same compound concentration range plotted against the percent of cytotoxicity. The ELISA $EC_{50}$ (50% inhibition of VEGF expression) for this particular compound is about 7 nM, while its $CC_{50}$ (50% cytotoxicity) is greater than about 2000 nM. Subsets of compounds that show similar efficacy/cytotoxicity windows are also identified.

The B9 cell line harbors the firefly luciferase reporter driven by the CMV promoter and flanked by the 5' and 3'UTRs of VEGF. Use of the B9 cell line with the HTS identifies compounds that specifically target the function of VEGF UTRs to modulate expression. Cell line B12 harbors the luciferase operably linked to control UTRs to replace the VEGF UTRs. Compounds that inhibit luciferase activity in both the B9 and B12 cell lines are general transcription and/or translation inhibitors or luciferase enzyme inhibitors. Several UTR specific compounds are identified in experiments with HTS identified compounds as described above. The dose-response curves of an identified compound show a sigmoidal curve in B9 cells and a concave curve in B12 cells when the percent luciferase inhibition of each is plotted over a compound concentration range from about $10^{-1}$ nM to about $10^4$ nM on the x-axis. The difference between the two cell lines (B9 and B12) shows that inhibition of VEGF production by this compound is through the VEGF UTRs, i.e., by a post-transcriptional control mechanism. A control is experiment is performed with a general translation inhibitor, puromycin. No difference in inhibition of luciferase expressionis observed with puromycin treatment in these two cell lines.

Example 2

Characteristics of UTR-Specific VEGF Inhibitors

All identified compounds are re-synthesized and shown by LC/MS and combustion analysis to be greater than 95% pure. Subsequently, the re-synthesized compounds are tested in the dose-response VEGF ELISA and luciferase assays are used to initially assess UTR specificity. All identified compounds that retain UTR specificity are defined as bonafide UTR-specific inhibitors of VEGF expression.

High-throughput screening using B9 cells, followed by endogenous VEGF ELISAs identified compounds that specifically inhibit hypoxia inducible VEGF expression for the treatment of ocular neovascular diseases and cancer. Compounds that target multiple angiogenesis factors (including VEGF) for the treatment of cancers are also identifiable. Several targets are used for these purposes, including TNF-$\alpha$, FGF-2, G-CSF, IGF-1, PDGF, and HIF-1$\alpha$.

ELISA assays analyze levels of expression of these factors using commercially available kits from R&D Systems (Minneapolis, Minn.). UTR-specific HTS identified compounds are tested for their ability to inhibit the expression of a subset of these proteins, including FGF-2 and IGF-1 in HeLa cells. Identified compounds that are very potent inhibitors of VEGF production as assayed in HeLa cells have $EC_{50}$ values ranging from low nM to high nM. Treatment with a general translation inhibitor (puromycin) results in similar inhibition for all these cytokines, with $EC_{50}$ values ranging from about 0.2 to about 2 $\mu$M.

Lead compounds are further characterized and optimized. Analogs are synthesized and identified compounds exhibit excellent potency in the VEGF ELISA assay ($EC_{50}$ values ranging from 0.5 nM to 50 nM). In another embodiment, an analog exhibits low nM potency. In an additional embodiment, several analogs are synthesized and a subset of identified compounds are very active ($EC_{50}$ values ranging from 1 nM to 50 nM) in the VEGF ELISA assay. Activity of a very potent analog is improved about 500-fold compared to its parent ($EC_{50}$ of 1 nM vs. 500 nM). Further characterization and optimization for selectivity and pharmaceutical properties (ADMET) of the most active compounds will develop a drug candidate(s) for clinical trials.

Example 3

HIF 1$\alpha$ UTR Modulates Reporter Gene Expression

Transient Transfections:

The HIF-1$\alpha$ reporter constructs pGEMS HIF-1$\alpha$5F3, pGEMS HIF-1$\alpha$5F and pGEMS HIF-1$\alpha$F3 and pGEMS F are each transfected in equal amounts into 293 and MCF7 cells using FuGENE™ 6 (Fugent, LLC) transfection reagent (F. Hoffmann-La Roche Ltd, Basel, Switzerland) according to the manufacturer's instructions. The plasmid phRL-CMV is co-transfected with each reporter to normalize for transfection efficiencies. After 24 hours, transfected cells are washed with PBS, washed again with new media, and placed either under normoxia or hypoxia for another 24 hours. At that time, cells are harvested and assayed for Renilla and Firefly luciferase activities using the Dual-Luciferase reporter assay system (Promega, Inc., Madison, Wis.) according to the manufacturer's instructions.

DNA Transfection and Generation of Stable Cell Line:

To generate a stable cell line, 293 cells are transiently transfected with pGEMS HIF-1$\alpha$5F3 as described above. Forty-eight hours later, cells are trypsinized, counted and seeded (10 ml) in 10 cm petri dishes at a concentration of 5000 cells/ml. The next day, 200 $\mu$g/ml hygromycin B is added to the culture media in order to select for cells in which the transiently transfected plasmid has stably integrated into the genome. Following ten to fourteen days of hygromycin B selection, individual hygromycin-resistant clones are expanded by transferring the cells from the petri dish to a single well in a twenty-four well plate using trypsin-soaked filter discs according to manufacturer's instructions. Individual cell lines are then selected for further studies based on firefly luciferase expression levels.

Luciferase Assay:

Firefly and Renilla luciferase activities or Firefly luciferase activity only are measured using the Dual Luciferase or the Luciferase reporter assay systems (Promega Inc., Madison, Wis.), according to the manufacturer's instructions respectively.

Quality Control of Stable Clones Using RT-PCR:

Total RNA is isolated from each stably transfected clone obtained using Trizol® reagent (Invitrogen Co., Carlsbad, Calif.) according to the manufacturer's instructions. RT-PCR is then used in order to confirm the presence of the correct-sized HIF-1 $\alpha$ UTRs in the firefly reporter mRNAs isolated from the stable clones. Either a HIF-1 $\alpha$ 5' UTR forward primer and a luciferase 5' reverse primer (5' CTGCAACTC-CGATAAATAACGCGCCCAACA 3', SEQ ID NO:1) or a luciferase 3' forward primer (5' CGGGTACCGAAAGGTCT-TACC 3', SEQ ID NO: 2) and the HIF-1 $\alpha$ 3' UTR reverse primer are used to amplify the 5' and 3' ends of the mRNA, respectively, from reverse-transcribed RNA using random hexamers.

Quantitation of Luciferase Reporter RNA Using Real Time RT-PCR:

Luciferase reporter mRNA levels from all stable clones obtained are quantified using TaqMan® Real Time RT-PCR (Applied Biosystems, Foster City, Calif.) according to the manufacturer's instructions. The following firefly luciferase specific primers and probe are used: FLuc F (5' TTCTTCAT-AGTTGACCGCTTGA 3', SEQ ID NO: 3), FLuc R (5' GTCATCGTCGGGAAGACCT 3', SEQ ID NO: 4) and FLuc probe (5' 6FAM-CGATATTGTTACAACAACCCAA- CATCTTCG-TAMRA 3', SEQ ID NO: 5 labeled with 6FAM at the 5' end and TAMRA at the 3' end). The luciferase reporter mRNA levels are normalized to actin mRNA levels using a commercially available actin-specific primers/probe set (Applied Biosystems, Foster City, Calif.).

High Throughput Screening:

High throughput screening ("HTS") for compounds that inhibit untranslated region-dependent expression of HIF-1α is accomplished using stable cell line generated as described above. A 293 cell line contains stably integrated copies of the firefly luciferase gene flanked by both the 5' and 3' UTRs of HIF-1α. The selected stable cell line is then used in a cell-based assay that has been optimized for cell number and percentage DMSO used for HTS.

Screening of compounds is accomplished within a week at a rate of 140 384-well plates per day. Each 384-well plate contains a standard puromycin titration curve that is used as a reference to calculate percent inhibition and the statistical significance of the data points generated in the assay. This curve is set-up in columns 3 and 4 of the 384-well plate and starts at a puromycin concentration of 20 µM that is then serially diluted 2-fold down to 0.078 µM and plated in quadruplicate. Columns 1 and 2 contain 16 standards each of a positive control consisting of cells in 0.5% DMSO and a negative control consisting of cells in 20 µM puromycin. The difference between the two controls is used as the window to calculate the percentage of inhibition of luciferase expression in the presence of a compound. Columns 5 through 24 contain compounds from a library of small molecules.

HIF-1 α stable cells at a ~70% confluency are used for HTS. Briefly, the cells are dislodged from the flask with 4 ml of 0.25% trypsin-EDTA (Gibco BRL, cat no. 25200-056) and diluted to 10 ml with non-selection media. This is repeated for all fourteen flasks and the cells are combined, passed through a filter, counted and diluted to a concentration of $1.3 \times 10^5$ cells/ml. Cells in a volume of 38 µl are added to each well containing 2 µl of compound from a small molecule library to yield a final compound concentration of 7.5 µM (3.75 mg/ml) in 0.5% DMSO. The puromycin standard curve also contains 0.5% DMSO. The compound-treated cells are incubated overnight (approximately 16 hours) under normoxic conditions and 37° C. in 5% $CO_2$. To monitor firefly luciferase activity, SteadyLite HTS (PerkinElmer Life and Analytical Sciences, Inc., Boston, Mass.) is prepared according to manufacturer's instructions and 20 µl are added to each well. Firefly luciferase activity in each well is detected with the ViewLux™ 1430 ultraHTS Microplate Imager (PerkinElmer Life and Analytical Sciences, Inc., Boston, Mass. All data obtained is uploaded into Activity Base for calculations and statistical analyses of the percentages of inhibition of luciferase activity.

Example 4

A Preferred Construct of the Present Invention

A high-level expression vector, pcDNA™3.1/Hygro (Invitrogen Corp., Carlsbad, Calif.), is prepared as follows. In a pcDNA™3.1/Hygro vector, the untranslated regions (UTRs) and restriction sites associated with cloning, expressing, or cloning and expressing a gene of interest or a reporter gene are removed or replaced.

Certain UTRs and restriction sites are native to high-copy mammalian expression vectors. A vector without UTRs and restriction sites is prepared as follows. Deletion mutagenesis is undertaken to remove UTRs and restriction sites from commercially-available vector, pcDNA™3.1/Hygro (Invitrogen Corp., Carlsbad, Calif.). The vector is constructed to remove a region that starts at the putative transcription start site of a UTR found upstream of the cloning site and continues in the 3' direction to the Hind III restriction site at the multiple cloning site of pcDNA™3.1/Hygro (Invitrogen Corp., Carlsbad, Calif.). The nucleic acid sequence removed is SEQ ID NO: 23 (5'-AGAGAACCCA CTGCTTACTG GCTTATCGAA ATTAATACGAC TCACTATAGG GAGACCCAAGC TGGCTAGCGT TTAAACTTA-3'). As such, UTRs that are native to the vector and heterologous to the target gene are removed. In pcDNA™3.1/Hygro (Invitrogen Corp., Carlsbad, Calif.), the UTR removed is from the bovine growth hormone gene. Another nucleic acid sequence that is removed is the UTR formed in the region starting at the Xho I site of pcDNA™3.1/Hygro (Invitrogen Corp., Carlsbad, Calif.) continuing in the 3' direction and ending at the poly(A) tail, which in pcDNA™3.1/Hygro (Invitrogen Corp., Carlsbad, Calif.) corresponding to the poly(A) tail from bovine growth hormone gene. By removing the nucleic acids from the Xho I site to the poly(A) tail, the 3' UTR native to the vector is removed, and the nucleic acid sequence that is removed is SEQ ID NO: 24. (5'-CTCGAGTCTA GAGGGC-CCGT TTAAACCCGCT GATCAGCCTC GACTGTGGCC TTCTAGTTGCC AGCCATCTGTTG TTGTCCCCTC CCCCGTCCCTT CCTTGACCCT GGAAGGTGCC ACTCCCACTG TCCTTTCCT-3').

A target UTR is cloned into the vector using a Hind III site and a BamHI site, which is downstream of the Hind III site. A target 5' UTR is inserted with a start codon upstream of the BamHI site. The reporter gene replaces the sequence between the BamHI site and a Not I site. Between the Not I site and a downstream Xho I site, the target 3' UTR is inserted with a stop codon downstream of the Not I site. The reporter gene is flanking and directly linked to the target 5' UTR and the target 3' UTR.

What is claimed:

1. A method of screening candidate compounds having a molecular weight less than 1,000 grams per mole for a compound having a molecular weight less than 1,000 grams per mole that modulates mature human target mRNA untranslated region (UTR)-regulated translation, comprising:

(a) contacting a compound having a molecular weight less than 1,000 grams per mole with a first human cell engineered to express a first reporter polypeptide translated from a first RNA transcript comprising a first reporter gene coding sequence operably linked to a first full-length 5' UTR and a first full-length 3' UTR, wherein the first 5' UTR and the first 3' UTR are each from the mature human target mRNA and the first 5' UTR is upstream of the first reporter gene coding sequence and the first UTR is downstream of the first reporter gene coding sequence, wherein the first reporter gene coding sequence is not the human target mRNA; and (b) contacting the compound with a second human cell engineered to express a second reporter polypeptide translated from a second RNA transcript comprising the first reporter gene coding sequence operably linked to a second full-length UTR and a second full-length 3' UTR, wherein the second 5' UTR and the second 3' UTR are each from a mRNA different from the mature human target mRNA and the second 5' UTR is upstream of the first reporter gene coding sequence and the second 3' UTR is downstream of the first reporter gene coding sequence; and (c) detecting the level of expression of the first and second reporter polypeptides, wherein: (i) an alteration in the level of expression of the first reporter polypeptide in the presence of the compound relative to the level of expression of the first reporter polypeptide in the absence of the compound, and (ii) no alteration in the level of expression of the second reporter polypeptide in the presence of the compound relative to the level of expression of the second reporter polypeptide in the absence of the compound, indicates that the compound modulates mature human target mRNA UTR-regulated translation.

2. The method of claim 1, wherein the first and second human cells are each from a human cell line.

3. The method of claim 2, wherein each human cell line is a 293 or HeLa cell line.

4. The method of claim 1, wherein the first and second human cells are engineered to stably express the first and second reporter polypeptides, respectively.

5. The method of claim 1, wherein the first and second reporter polypeptides are luciferase.

6. A method of screening candidate compounds having a molecular weight less than 1,000 grams per mole for a compound having a molecular weight less than 1,000 grams per mole that modulates mature human target mRNA untranslated region-regulated translation, comprising:

(a) contacting a compound having a molecular weight less than 1,000 grams per mole with a composition comprising a lysate or translation extract and a first RNA transcript comprising a first reporter gene coding sequence operably linked to a first full-length 5' UTR and a first full-length 3' UTR, wherein the first 5' UTR and the first 3' UTR are each from the mature human target mRNA and the first 5' UTR is upstream of the reporter gene coding sequence and the first 3' UTR is downstream of the first reporter gene coding sequence, wherein the first reporter gene coding sequence is not the human target mRNA; and (b) contacting the compound with a composition comprising a lysate or translation extract and a second RNA transcript comprising the first reporter gene coding sequence operably linked to a second full-length 5'-UTR and a second full-length 3' UTR, wherein the second 5' UTR and the second 3' UTR are each from a mRNA different from the mature human target mRNA, and the second 5' UTR is upstream of the first reporter gene coding sequence and the second 3' UTR is downstream of the first reporter gene coding sequence; and (c) detecting the level of expression of the first and second reporter polypeptides translated from the first and second RNA transcripts, respectively, wherein: (i) an alteration in the level of expression of the first reporter polypeptide in the presence of the compound relative to the level of expression of the first reporter polypeptide in the absence of the compound, and (ii) no alteration in the level of expression of the second reporter polypeptide in the presence of the compound relative to the level of expression of the second reporter polypeptide in the absence of the compound, indicates that the compound modulates mature human target mRNA UTR-regulated.

7. The method of claim 1, wherein the first and second reporter polypeptides are green fluorescent protein, neomycin phosphotransferase II, or an antibiotic resistance sequence.

8. The method of claim 6, wherein the first and second reporter polypeptides are green fluorescent protein, neomycin phosphotransferase II, or an antibiotic resistance sequence.

9. The method of claim 6, wherein the first and second reporter polypeptides are luciferase.

10. A method of screening candidate compounds having a molecular weight less than 1,000 grams per mole for a compound having a molecular weight less than 1,000 grams per mole that inhibits mature human target mRNA untranslated region (UTR)-regulated translation, comprising:

(a) contacting a compound having a molecular weight less than 1,000 grams per mole with a first human cell engineered to express a first reporter polypeptide translated from a first RNA transcript comprising a first reporter gene coding sequence operably linked to a first full-length 5' UTR and a first full-length 3' UTR, wherein the first 5' UTR and the first 3' UTR are each from the mature human target mRNA and the first 5' UTR is upstream of the first reporter gene coding sequence and the first 3' UTR is downstream of the first reporter gene coding sequence, wherein the first reporter gene coding sequence is not the human target mRNA; and (b) contacting the compound with a second human cell engineered to express a second reporter polypeptide translated from a second RNA transcript comprising the first reporter gene coding sequence operably linked to a second full-length 5' UTR and a second full-length 3' UTR, wherein the second 5' UTR and the second 3' UTR are each from a mRNA different from the mature human target mRNA and the second 5' UTR is upstream of the first reporter gene coding sequence and the second 3' UTR is downstream of the first reporter gene coding sequence; and (c) detecting the level of expression of the first and second reporter polypeptides, wherein: (i) a decrease in the level of expression of the first reporter polypeptide in the presence of the compound relative to the level of expression of the first reporter polypeptide in the absence of the compound, and (ii) no alteration in the level of expression of the second reporter polypeptide in the presence of the compound relative to the level of expression of the second reporter polypeptide in the absence of the compound, indicates that the compound inhibits human target mRNA UTR-regulated translation.

11. A method of screening candidate compounds having a molecular weight less than 1,000 grams per mole for a compound having a molecular weight less than 1,000 grams per mole that modulates mature human target mRNA untranslated (UTR)-regulated translation, comprising:

(a) contacting a compound having a molecular weight less than 1.000 grams per mole with a first human cell engineered to express a first reporter polypeptide translated from a first RNA transcript comprising a first reporter gene coding sequence operably linked to a first full-length 5' UTR and a first full-length 3' UTR, wherein the first 5' UTR and the first 3' UTR are each from the mature human target mRNA and the first 5' UTR is upstream of the first reporter gene coding sequence and the first 3' UTR is downstream of the first reporter gene coding sequence, wherein the first reporter gene coding sequence is not the human target mRNA;

(b) contacting the compound with a second human cell engineered to express a second reporter polypeptide translated from a second RNA transcript comprising the first reporter gene coding sequence operably linked to a second full-length 5' UTR and a second full-length 3' UTR, wherein the second 5' UTR and the second 3' UTR are each from a mRNA different from the mature human target mRNA and the second 5' UTR is upstream of the first reporter gene coding sequence and the second 3' UTR is downstream of the first reporter gene coding sequence;

(c) contacting the first and second human cells with puromycin; and (d) detecting the level of expression of the first and second reporter polypeptides in the presence of the compound and detecting the level of expression of the first and second reporter polypeptides in the presence of puromycin, wherein: (i) an alteration in the level of expression of the first reporter polypeptide in the presence of the compound relative to the level of expression of the first reporter polypeptide in the absence of the compound, (ii) no alteration in the level of expression of the second reporter polypeptide in the presence of the compound relative to the level of expression of the second reporter polypeptide in the absence of the compound, and (iii) no alteration in the level of expression of the first reporter polypeptide in the presence of puromycin relative to the level of expression of the second reporter protein in the presence of puromycin indicates that the compound modulates human target mRNA UTR-regulated translation.

12. A method of screening candidate compounds having a molecular weight less than 1,000 grams per mole for a compound having a molecular weight less than 1,000 grams per mole that modulates mature human target mRNA untranslated region (UTR)-regulated translation, comprising:

(a) contacting a compound having a molecular weight less than 1.000 grams per mole with a first composition comprising a lysate or translation extract and a first RNA transcript comprising a first reporter gene coding sequence operably linked to a first full-length 5' UTR and a first full-length 3' UTR, wherein the first 5' UTR and the first 3' UTR are each from the mature human target mRNA and the first 5' UTR is upstream of the reporter gene coding sequence and the first 3' UTR is downstream of the first reporter gene coding sequence, wherein the first reporter gene coding sequence is not the human target mRNA;

(b) contacting the compound with a second composition comprising a lysate or translation extract and a second RNA transcript comprising the first reporter gene coding sequence operably linked to a second full-length 5'-UTR and a second full-length 3' UTR, wherein the second 5' UTR and the second 3' UTR are each from a mRNA different from the mature human target mRNA, and the second 5' UTR is upstream of the first reporter gene coding sequence and the second 3' UTR is downstream of the first reporter gene coding sequence;

(c) contacting the first and second compositions with puromycin; and (d) detecting the level of expression of the first and second reporter polypeptides translated from the first and second RNA transcripts, respectively, in the presence of the compound and detecting the level of expression of the first and second reporter polypeptides translated from the first and second RNA transcripts, respectively, in the presence of puromycin wherein: (i) an alteration in the level of expression of the first reporter polypeptide in the presence of the compound relative to the level of expression of the first reporter polypeptide in the absence of the compound, (ii) no alteration in the level of expression of the second reporter polypeptide in the presence of the compound relative to the level of expression of the second reporter polypeptide in the absence of the compound, and (iii) no alteration in the level of expression of the first reporter polypeptide in the presence of puromycin relative to the level of expression of the second reporter protein in the presence of puromycin indicates that the compound modulates human target mRNA UTR-regulated translation.

13. The method of claim 10 or 11, wherein the first and second human cells are each from a human cell line.

14. The method of claim 13, wherein each human cell line is a 293 or HeLa cell line.

15. The method of claim 10 or 11, wherein the first and second human cells are engineered to stably express the first and second reporter polypeptides.

16. The method of claim 10, 11, or 12, wherein the first and second reporter polypeptides are luciferase.

17. The method of claim 10, 11, or 12, wherein the first and second reporter polypeptides are green fluorescent protein, neomycin phosphotransferase II, or an antibiotic resistance sequence.

* * * * *

SEQUENCE LISTING

```
<160> NUMBER OF SEQ ID NOS: 24

<210> SEQ ID NO 1
<211> LENGTH: 30
<212> TYPE: DNA
<213> ORGANISM: Artificial
<220> FEATURE:
<223> OTHER INFORMATION: Synthetic Construct

<400> SEQUENCE: 1
ctgcaactcc gataaataac gcgcccaaca                                     30
```

<210> SEQ ID NO 2
<211> LENGTH: 21
<212> TYPE: DNA
<213> ORGANISM: Artificial
<220> FEATURE:
<223> OTHER INFORMATION: Synthetic Construct

<400> SEQUENCE: 2
cgggtaccga aaggtcttac c                                              21

<210> SEQ ID NO 3
<211> LENGTH: 22
<212> TYPE: DNA
<213> ORGANISM: Artificial
<220> FEATURE:
<223> OTHER INFORMATION: Synthetic Construct

<400> SEQUENCE: 3
ttcttcatag ttgaccgctt ga                                             22

<210> SEQ ID NO 4
<211> LENGTH: 19
<212> TYPE: DNA
<213> ORGANISM: Artificial
<220> FEATURE:
<223> OTHER INFORMATION: Synthetic Construct

<400> SEQUENCE: 4
gtcatcgtcg ggaagacct                                                 19

<210> SEQ ID NO 5
<211> LENGTH: 30
<212> TYPE: DNA
<213> ORGANISM: Artificial
<220> FEATURE:
<223> OTHER INFORMATION: Synthetic Construct

<400> SEQUENCE: 5
cgatattgtt acaacaaccc aacatcttcg                                     30

<210> SEQ ID NO 6
<211> LENGTH: 1038
<212> TYPE: DNA
<213> ORGANISM: Artificial
<220> FEATURE:
<223> OTHER INFORMATION: Synthetic Construct

<400> SEQUENCE: 6
tcgcggaggc ttggggcagc cgggtagctc ggaggtcgtg gcgctggggg ctagcaccag      60
cgctctgtcg ggaggcgcag cggttaggtg gaccggtcag cggactcacc ggccagggcg     120
ctcggtgctg gaatttgata ttcattgatc cgggttttat ccctcttctt ttttcttaaa     180
catttttttt taaaactgta ttgtttctcg tttaattta ttttgcttg ccattcccca       240 cttgaatcgg gccgacggct tggggagatt gctctacttc cccaaatcac tgtggatttt     300
ggaaaccagc agaaagagga aagaggtagc aagagctcca gagagaagtc gaggaagaga     360
gagacggggt cagagagagc gcgcgggcgt gcgagcagcg aaagcgacag gggcaaagtg     420
agtgacctgc ttttgggggt gaccgccgga gcgcggcgtg agccctcccc cttgggatcc     480
cgcagctgac cagtcgcgct gacggacaga cagacagaca ccgccccag ccccagctac      540 cacctcctcc ccggcggcg gcggacagtg gacgcggcgg cgagccgcgg gcaggggccg      600
gagcccgcgc ccggaggcgg ggtggagggg gtcgggctc gcggcgtcgc actgaaactt      660

```
ttcgtccaac ttctgggctg ttctcgcttc ggaggagccg tggtccgcgc gggggaagcc      720
gagccgagcg gagccgcgag aagtgctagc tcgggccggg aggagccgca gccggaggag      780
ggggaggagg aagaagagaa ggaagaggag aggggccgc agtggcgact cggcgctcgg       840
aagccgggct catggacggg tgaggcggcg gtgtgcgcag acagtgctcc agccgcgcgc      900
gctccccagg ccctggcccg ggcctcgggc cggggaggaa gagtagctcg ccgaggcgcc      960
gaggagagcg ggccgcccca cagcccgagc cggagaggga gcgcgagccg cgccggcccc     1020
ggtcgggcct ccgaaacc                                                   1038
```

<210> SEQ ID NO 7
<211> LENGTH: 1889
<212> TYPE: DNA
<213> ORGANISM: Artificial
<220> FEATURE:
<223> OTHER INFORMATION: Synthetic Construct

<400> SEQUENCE: 7

```
gccgggcagg aggaaggagc ctccctcagg gtttcgggaa ccagatctct ctccaggaaa       60
gactgataca gaacgatcga tacagaaacc acgctgccgc caccacacca tcaccatcga      120
cagaacagtc cttaatccag aaacctgaaa tgaaggaaga ggagactctg cgcagagcac      180
tttgggtccg gagggcgaga ctccggcgga agcattcccg ggcgggtgac ccagcacggt      240
ccctcttgga attggattcg ccattttatt tttcttgctg ctaaatcacc gagcccggaa      300
gattagagag ttttatttct gggattcctg tagacacacc cacccacata catacattta      360
tatatatata tattatatat atataaaaat aaatatctct attttatata tataaaatat      420
atatattctt tttttaaatt aacagtgcta atgttattgg tgtcttcact ggatgtattt      480
gactgctgtg gacttgagtt gggaggggaa tgttcccact cagatcctga cagggaagag      540
gaggagatga gagactctgg catgatcttt ttttgtccc acttggtggg gccagggtcc       600
tctcccctgc ccaagaatgt gcaaggccag ggcatggggg caaatatgac ccagttttgg      660
gaacaccgac aaacccagcc ctggcgctga gcctctctac cccaggtcag acggacagaa      720
agacaaatca caggttccgg gatgaggaca ccggctctga ccaggagttt ggggagcttc      780
aggacattgc tgtgctttgg ggattccctc cacatgctgc acgcgcatct cgcccccagg      840
ggcactgcct ggaagattca ggagcctggg cggccttcgc ttactctcac ctgcttctga      900
gttgcccagg aggccactgg cagatgtccc ggcgaagaga agagacacat tgttggaaga      960
agcagcccat gacagcgccc cttcctggga ctcgccctca tcctcttcct gctcccttc     1020 ctggggtgca gcctaaaagg acctatgtcc tcacaccatt gaaaccacta gttctgtccc     1080
cccaggaaac ctggttgtgt gtgtgtgagt ggttgacctt cctccatccc ctggtccttc     1140
ccttcccttc ccgaggcaca gagagacagg gcaggatcca cgtgcccatt gtggaggcag     1200
agaaaagaga aagtgtttta tacggtac ttatttaata tcccttttta attagaaatt       1260
agaacagtta atttaattaa agagtagggt ttttttcag tattcttggt taatatttaa      1320
tttcaactat ttatgagatg tatctttgc tctctcttgc tctcttattt gtaccggttt       1380
ttgtatataa aattcatgtt tccaatctct ctctccctga tcggtgacag tcactagctt     1440
atcttgaaca gatatttaat tttgctaaca ctcagctctg ccctccccga tcccctggct     1500
ccccagcaca cattccttg aaagagggtt tcaatataca tctacatact atatatatat      1560
tgggcaactt gtatttgtgt gtatatatat atatatatgt ttatgtatat atgtgatcct     1620
```

| gaaaaaataa acatcgctat tctgtttttt atatgttcaa accaaacaag aaaaaataga | 1680 |
| gaattctaca tactaaatct ctctcctttt ttaattttaa tatttgttat catttattta | 1740 |
| ttggtgctac tgtttatccg taataattgt ggggaaaaga tattaacatc acgtctttgt | 1800 |
| ctctagtgca gttttttcgag atattccgta gtacatattt attttttaaac aacgacaaag | 1860 |
| aaatacagat atatcttaaa aaaaaaaaa | 1889 |

<210> SEQ ID NO 8
<211> LENGTH: 179
<212> TYPE: DNA
<213> ORGANISM: Artificial
<220> FEATURE:
<223> OTHER INFORMATION: Synthetic Construct

<400> SEQUENCE: 8

| ctccctcagc aaggacagca gaggaccagc taagagggag agaagcaact acagaccccc | 60 |
| cctgaaaaca accctcagac gccacatccc ctgacaagct gccaggcagg ttctcttcct | 120 |
| ctcacatact gacccacggc tccaccctct ctcccctgga aaggacacca tgagcactg | 179 |

<210> SEQ ID NO 9
<211> LENGTH: 798
<212> TYPE: DNA
<213> ORGANISM: Artificial
<220> FEATURE:
<223> OTHER INFORMATION: Synthetic Construct

<400> SEQUENCE: 9

| ggaggacgaa catccaacct tcccaaacgc ctcccctgcc ccaatccctt tattaccccc | 60 |
| tccttcagac ccctcaacc tcttctggct caaaagaga attgggggct tagggtcgga | 120 |
| acccaagctt agaactttaa gcaacaagac caccacttcg aaacctggga ttcaggaatg | 180 |
| tgtggcctgc acagtgaagt gctggcaacc actaagaatt caaactgggg cctccagaac | 240 |
| tcactggggc ctacagcttt gatccctgac atctggaatc tggagaccag ggagcctttg | 300 |
| gttctggcca gaatgctgca ggacttgaga agaccctcacc tagaaattga cacaagtgga | 360 |
| ccttaggcct tcctctctcc agatgtttcc agacttcctt gagacacgga gcccagccct | 420 |
| ccccatggag ccagctccct ctatttatgt ttgcacttgt gattatttat tatttattta | 480 |
| ttatttattt atttacagat gaatgtattt atttgggaga ccggggtatc ctgggggacc | 540 |
| caatgtagga gctgccttgg ctcagacatg ttttcgtga aaacggagct gaacaatagg | 600 |
| ctgttcccat gtagcccect ggcctctgtg ccttcttttg attatgtttt ttaaaatatt | 660 |
| tatctgatta agttgtctaa acaatgctga tttggtgacc aactgtcact cattgctgag | 720 |
| cctctgctcc ccaggggagt tgtgtctgta atcgccctac tattcagtgg cgagaaataa | 780 |
| agtttgctta gaaaagaa | 798 |

<210> SEQ ID NO 10
<211> LENGTH: 7
<212> TYPE: DNA
<213> ORGANISM: Artificial
<220> FEATURE:
<223> OTHER INFORMATION: Synthetic Construct

<400> SEQUENCE: 10

| tatttat | 7 |

<210> SEQ ID NO 11
<211> LENGTH: 33

<210> SEQ ID NO 11
<211> LENGTH: 33
<212> TYPE: DNA
<213> ORGANISM: Artificial
<220> FEATURE:
<223> OTHER INFORMATION: Synthetic Construct

<400> SEQUENCE: 11
ttatttatta tttatttatt atttatttat tta                              33

<210> SEQ ID NO 12
<211> LENGTH: 8
<212> TYPE: DNA
<213> ORGANISM: Artificial
<220> FEATURE:
<223> OTHER INFORMATION: Synthetic Construct

<400> SEQUENCE: 12 tatttatt                                                          8

<210> SEQ ID NO 13
<211> LENGTH: 48
<212> TYPE: DNA
<213> ORGANISM: Artificial
<220> FEATURE:
<223> OTHER INFORMATION: Synthetic Construct

<400> SEQUENCE: 13
taggagctgc cttggctcag acatgttttc cgtgaaaacg gagctgaa              48

<210> SEQ ID NO 14
<211> LENGTH: 28
<212> TYPE: DNA
<213> ORGANISM: Artificial
<220> FEATURE:
<223> OTHER INFORMATION: Synthetic Construct

<400> SEQUENCE: 14
ttttgattat gttttttaaa atatttat                                    28

<210> SEQ ID NO 15
<211> LENGTH: 6
<212> TYPE: DNA
<213> ORGANISM: Artificial
<220> FEATURE:
<223> OTHER INFORMATION: Synthetic Construct

<400> SEQUENCE: 15 aataaa                                                            6

<210> SEQ ID NO 16
<211> LENGTH: 296
<212> TYPE: DNA
<213> ORGANISM: Artificial
<220> FEATURE:
<223> OTHER INFORMATION: Synthetic Construct

<400> SEQUENCE: 16
cgagcttggc tgcttctggg gcctgtgtgg ccctgtgtgt cggaaagatg gagcaagaag   60
ccgagcccga ggggcggccg cgacccctct gaccgagatc ctgctgcttt cgcagccagg  120
agcaccgtcc ctccccggat tagtgcgtac gagcgcccag tgccctggcc cggagagtgg  180
aatgatcccc gaggcccagg gcgtcgtgct tccgcgcgcc ccgtgaagga aactggggag  240
tcttgaggga cccccgactc caagcgcgaa aaccccggat ggtgaggagc aggcaa      296

<210> SEQ ID NO 17

<211> LENGTH: 150
<212> TYPE: DNA
<213> ORGANISM: Artificial
<220> FEATURE:
<223> OTHER INFORMATION: Synthetic Construct

<400> SEQUENCE: 17

```
aattctcgag ctcgtcgacc ggtcgacgag ctcgagggtc gacgagctcg agggcgcgcg      60
cccggccccc acccctcgca gcaccccgcg cccgcgccc tcccagccgg gtccagccgg     120
agccatgggg ccggagccgc agtgagcacc                                      150
```

<210> SEQ ID NO 18
<211> LENGTH: 21
<212> TYPE: DNA
<213> ORGANISM: Artificial
<220> FEATURE:
<223> OTHER INFORMATION: Synthetic Construct

<400> SEQUENCE: 18

```
atggggccgg agccgcagtg a                                                21
```

<210> SEQ ID NO 19
<211> LENGTH: 612
<212> TYPE: DNA
<213> ORGANISM: Artificial
<220> FEATURE:
<223> OTHER INFORMATION: Synthetic Construct

<400> SEQUENCE: 19

```
accagaaggc caagtccgca gaagccctga tgtgtcctca gggagcaggg aaggcctgac      60
ttctgctggc atcaagaggt gggagggccc tccgaccact tccaggggaa cctgccatgc     120
caggaacctg tcctaaggaa ccttccttcc tgcttgagtt cccagatggc tggaaggggt     180
ccagcctcgt tggaagagga acagcactgg ggagtctttg tggattctga ggccctgccc     240
aatgagactc tagggtccag tggatgccac agcccagctt ggccctttcc ttccagatcc     300
tgggtactga aagccttagg gaagctggcc tgagagggga agcggcccta agggagtgtc     360
taagaacaaa agcgacccat tcagagactg tccctgaaac ctagtactgc ccccatgag      420
gaaggaacag caatggtgtc agtatccagg ctttgtacag agtgcttttc tgtttagttt     480
ttacttttt tgttttgttt ttttaaagac gaaataaaga cccaggggag aatgggtgtt     540
gtatggggag gcaagtgtgg ggggtccttc tccacaccca ctttgtccat ttgcaaatat     600
attttggaaa ac                                                         612
```

<210> SEQ ID NO 20
<211> LENGTH: 336
<212> TYPE: DNA
<213> ORGANISM: Artificial
<220> FEATURE:
<223> OTHER INFORMATION: Synthetic Construct

<400> SEQUENCE: 20

```
tcgcggaggc ttggggcagc cgggtagctc ggaggtcgtg gcgctggggg ctagcaccag      60
cgctctgtcg ggaggcgcag cggttaggtg gaccggtcag cggactcacc ggccagggcg     120
ctcggtgctg gaatttgata ttcattgatc cgggttttat ccctcttctt ttttcttaaa     180
cattttttt taaaactgta ttgtttctcg ttttaattta ttttgcttg ccattcccca       240
cttgaatcgg gccgacggct tggggagatt gctctacttc cccaaatcac tgtggatttt     300
ggaaaccagc agaaagagga aagaggtagc aagagc                               336
```

```
<210> SEQ ID NO 21
<211> LENGTH: 476
<212> TYPE: DNA
<213> ORGANISM: Artificial
<220> FEATURE:
<223> OTHER INFORMATION: Synthetic Construct

<400> SEQUENCE: 21
tcgcggaggc ttggggcagc cgggtagctc ggaggtcgtg gcgctggggg ctagcaccag      60
cgctctgtcg ggaggcgcag cggttaggtg gaccggtcag cggactcacc ggccagggcg     120
ctcggtgctg gaatttgata ttcattgatc cgggttttat ccctcttctt ttttcttaaa     180
catttttttt taaaactgta ttgtttctcg ttttaattta tttttgcttg ccattcccca     240
cttgaatcgg gccgacggct tggggagatt gctctacttc cccaaatcac tgtggatttt     300
ggaaaccagc agaaagagga aagaggtagc aagagctcca gagagaagtc gaggaagaga     360
gagacggggt cagagagagc gcgcgggcgt gcgagcagcg aaagcgacag ggcaaagtg      420 agtgacctgc ttttgggggt gaccgccgga gcgcggcgtg agccctcccc cttggg        476

<210> SEQ ID NO 22
<211> LENGTH: 73
<212> TYPE: DNA
<213> ORGANISM: Artificial
<220> FEATURE:
<223> OTHER INFORMATION: Synthetic Construct

<400> SEQUENCE: 22
cttttctgtt tagtttttac tttttttgtt ttgttttttt aaagacgaaa taaagaccca      60
ggggagaatg ggt                                                         73

<210> SEQ ID NO 23
<211> LENGTH: 81
<212> TYPE: DNA
<213> ORGANISM: Artificial
<220> FEATURE:
<223> OTHER INFORMATION: Synthetic Construct

<400> SEQUENCE: 23
agagaaccca ctgcttactg gcttatcgaa attaatacga ctcactatag ggagacccaa      60
gctggctagc gtttaaactt a                                                81

<210> SEQ ID NO 24
<211> LENGTH: 134
<212> TYPE: DNA
<213> ORGANISM: Artificial
<220> FEATURE:
<223> OTHER INFORMATION: Synthetic Construct

<400> SEQUENCE: 24
ctcgagtcta gagggcccgt ttaaacccgc tgatcagcct cgactgtggc cttctagttg      60
ccagccatct gttgttgtcc cctcccccgt cccttccttg accctggaag gtgccactcc     120
cactgtcctt tcct                                                       134
```